United States Patent
McWeeney et al.

(10) Patent No.: US 11,083,610 B2
(45) Date of Patent: Aug. 10, 2021

(54) EXPANDABLE STENT DELIVERY APPARATUS TO COVER AN ACCESS SITE

(71) Applicant: Covidien LP, Mansfield, MA (US)

(72) Inventors: John O. McWeeney, Brighton, MA (US); Hillary K. Huszar, Redwood City, CA (US); Mark A. Maguire, Hillsborough, CA (US); Shawn C. Daniel, San Jose, CA (US)

(73) Assignee: Covidien LP, Mansfield, MA (US)

( * ) Notice: Subject to any disclaimer, the term of this patent is extended or adjusted under 35 U.S.C. 154(b) by 187 days.

(21) Appl. No.: 16/242,609

(22) Filed: Jan. 8, 2019

(65) Prior Publication Data
US 2020/0214864 A1  Jul. 9, 2020

(51) Int. Cl.
*A61F 2/966* (2013.01)
*A61F 2/91* (2013.01)
*A61F 2/07* (2013.01)
*A61F 2/82* (2013.01)

(52) U.S. Cl.
CPC ............... *A61F 2/966* (2013.01); *A61F 2/07* (2013.01); *A61F 2/91* (2013.01); *A61F 2002/823* (2013.01); *A61F 2250/0039* (2013.01)

(58) Field of Classification Search
CPC ............... A61F 2/07; A61F 2/91; A61F 2/966
See application file for complete search history.

(56) References Cited

U.S. PATENT DOCUMENTS

| | | | |
|---|---|---|---|
| 2003/0212431 A1* | 11/2003 | Brady | A61F 2/844 606/200 |
| 2006/0212105 A1* | 9/2006 | Dorn | A61F 2/95 623/1.11 |
| 2010/0249895 A1 | 9/2010 | Ramos Clamote et al. | |
| 2012/0172929 A1 | 7/2012 | Shalev | |
| 2012/0253387 A1 | 10/2012 | Teichman et al. | |
| 2015/0081000 A1* | 3/2015 | Hossainy | A61F 2/90 623/1.2 |
| 2018/0311058 A1 | 11/2018 | Mannion et al. | |
| 2020/0114060 A1* | 4/2020 | Vartanian | A61L 31/048 |

OTHER PUBLICATIONS

Extended European Search Report—P6639EP00—Application No. 20150597-1113—dated May 19, 2020.

* cited by examiner

*Primary Examiner* — Tuan V Nguyen
(74) *Attorney, Agent, or Firm* — Holland & Hart LLP

(57) ABSTRACT

Methods, apparatuses and systems are described for expandable stent delivery apparatus to cover an access site. The method may include delivering the stent through an access site and deploying a distal portion of the stent from within an outer sheath. In some cases, the method may further include pushing a proximal portion of the stent from the outer sheath such that upon fully exiting the outer sheath, the proximal portion extends proximally to at least partially cover the access site with the stent. The system for delivering the stent into the body lumen may include a stent, a stent delivery apparatus, and an outer sheath. The system may further include an internal pusher configured to push a proximal portion of the stent from the outer sheath and axially compress the stent such that upon fully exiting the outer sheath, the proximal portion extends proximally to cover the access site.

15 Claims, 38 Drawing Sheets

EXPANDABLE STENT DELIVERY APPARATUS TO COVER AN ACCESS SITE

BACKGROUND

Diseases and disorders of the gallbladder, pancreas, and bile ducts (i.e., pancreaticobiliary system) are associated with significant morbidity, mortality, and impaired quality of life. Obstructions, tumors, injuries, leakages, inflammation, infection, and lesions can occur in these structures, which can eventually lead to conditions such as biliary colic, cholecystitis, choledocholithiasis, cholelithiasis, pancreatitis, pancreatic duct stone formations, and chronic abdominal pain. Diseases of the pancreaticobiliary system may also be associated with nutritional disorders, such as malnutrition, obesity, and high cholesterol.

To treat a biliary obstruction, a clinician may perform a stent delivery procedure to place a stent across the obstruction. In general, a stent delivery procedure may include placing an endoscope into the gastrointestinal tract and accessing the bile duct with a catheter. A guidewire may then be deployed through the catheter and into the bile duct. Once the guidewire is in place, a stent or other treatment device may be advanced over the guidewire into the bile duct. After the stent is placed in the bile duct, the clinician may withdraw the stent delivery system.

SUMMARY

The described features generally relate to improved methods, systems, and devices for an expandable stent delivery apparatus to cover an access site. The method may include delivering the stent within the body lumen, deploying a distal portion of the stent from within an outer sheath, and pushing a proximal portion of the stent from the outer sheath such that the proximal portion of the stent compresses within the body lumen and bounces back to at least partially cover the access site. The system for delivering the stent into the body lumen may include a stent, a stent delivery apparatus configured to deliver the stent through an access site, and an outer sheath configured to constrain the stent in a collapsed configuration. The system may further include an internal pusher configured to push the proximal portion of the stent from the outer sheath such that upon fully exiting the outer sheath, the proximal portion extends in a proximal direction to fully expand the stent within the body lumen.

A method for delivering a stent into a body lumen is described. The method may include delivering a stent through an access site in a wall of the body lumen, deploying a distal portion of the stent from within an outer sheath, and pushing a proximal portion of the stent from the outer sheath such that upon fully exiting the outer sheath, the proximal portion extends proximally to at least partially cover the access site with the stent.

In some cases, deploying the distal portion of the stent from the outer sheath may further include retracting the outer sheath toward the access site such that the distal portion of the stent expands within the body lumen. In some cases, pushing the proximal portion of the stent from the outer sheath may further include advancing an internal pusher in a distal direction, wherein the internal pusher is at least partially disposed within the outer sheath and coupled with the proximal portion of the stent. In some cases, pushing the proximal portion of the stent from the outer sheath may further include advancing the internal pusher until the proximal portion of the stent fully exits the outer sheath. In some cases, advancing the internal pusher in the distal direction may further include aligning a distal end of the internal pusher with the distal end of the outer sheath.

The method may further include maintaining the outer sheath in a locked position while advancing the internal pusher. The method may further include anchoring the distal portion of the stent against a stricture within the body lumen such that the distal portion remains in a fixed position. The method may further include compressing the stent to a compressed state by advancing the proximal portion of the stent towards the distal portion of the stent. The method may further include expanding the proximal portion of the stent from the compressed state to an expanded state.

The method may further include retracting the outer sheath toward the access site while maintaining the proximal portion of the stent within the outer sheath. In some cases, retracting the outer sheath toward the access site may further include aligning a distal end of the outer sheath with the wall of the body lumen of the access site. The method may further include retracting the outer sheath past a stent anchor before pushing the proximal portion of the stent from the outer sheath. The method may further include compressing the distal portion of the stent against a stricture within the body lumen based at least in part on deploying the distal portion of the stent from the outer sheath.

The method may further include removing the outer sheath from the body lumen through the access site. The method may further include expanding the stent within the body lumen. The method may further include advancing a stent delivery apparatus through the access site before delivering the stent and removing the stent delivery apparatus through the access site after expanding the stent. In some cases, the stent delivery apparatus comprises a guidewire, wherein a tubular member is disposed around the guidewire, and the method further includes advancing the guidewire through the access site before delivering the stent.

A system for delivering a stent into a body lumen is described. The system may include a stent, a stent delivery apparatus configured to deliver the stent through an access site in a wall of the body lumen, an outer sheath configured to constrain the stent in a collapsed configuration, and an internal pusher configured to push a proximal portion of the stent from the outer sheath and axially compress the stent within the body lumen such that upon fully exiting the outer sheath, the proximal portion extends proximally to at least partially cover the access site with the stent.

In some examples, the internal pusher is coupled with the proximal portion of the stent a distal end of the internal pusher abuts a proximal end of the proximal portion of the stent. In some examples, the outer sheath comprises a lumen configured to slideably move the internal pusher with respect to the outer sheath. In some examples, the internal pusher is at least partially disposed within the outer sheath.

The system may further include a tubular member being configured to advance through the access site in the wall of the body lumen. In some examples, the stent is disposed onto the tubular member such that the tubular member is inside the stent along a distal portion of the stent and outside of the stent along a proximal portion of the stent. In some examples, the stent is disposed onto the tubular member such that the tubular member is inside the stent along an entire portion of the stent.

The system may further include a stent anchor coupled with the tubular member and configured to mark a location to retract the outer sheath before pushing the proximal portion of the stent from the outer sheath. The system may further include a first handle coupled with a proximal end of the tubular member and configured to retract the tubular member in a proximal direction, a second handle coupled with a proximal end of the outer sheath and configured to retract the outer sheath in the proximal direction, and a third handle coupled with a proximal end of the internal pusher and configured to retract the internal pusher in the proximal direction. The system may further include a stationary member coupled to the outer sheath and configured to maintain the outer sheath in a locked position while advancing the internal pusher. In some examples, the stent comprises nitinol, alloy derivatives, or both such that the stent compresses within the body lumen. The system may further include a guidewire slidably disposed within the tubular member Certain embodiments of the present disclosure may include some, all, or none of the above advantages or features. One or more other technical advantages or features may be readily apparent to those skilled in the art from the figures, descriptions, and claims included herein. Moreover, while specific advantages or features have been enumerated above, various embodiments may include all, some, or none of the enumerated advantages or features.

Further scope of the applicability of the described methods and systems will become apparent from the following detailed description, claims, and drawings. The detailed description and specific examples are given by way of illustration only, since various changes and modifications within the spirit and scope of the description will become apparent to those skilled in the art.

BRIEF DESCRIPTION OF THE DRAWINGS

In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Figure 1:
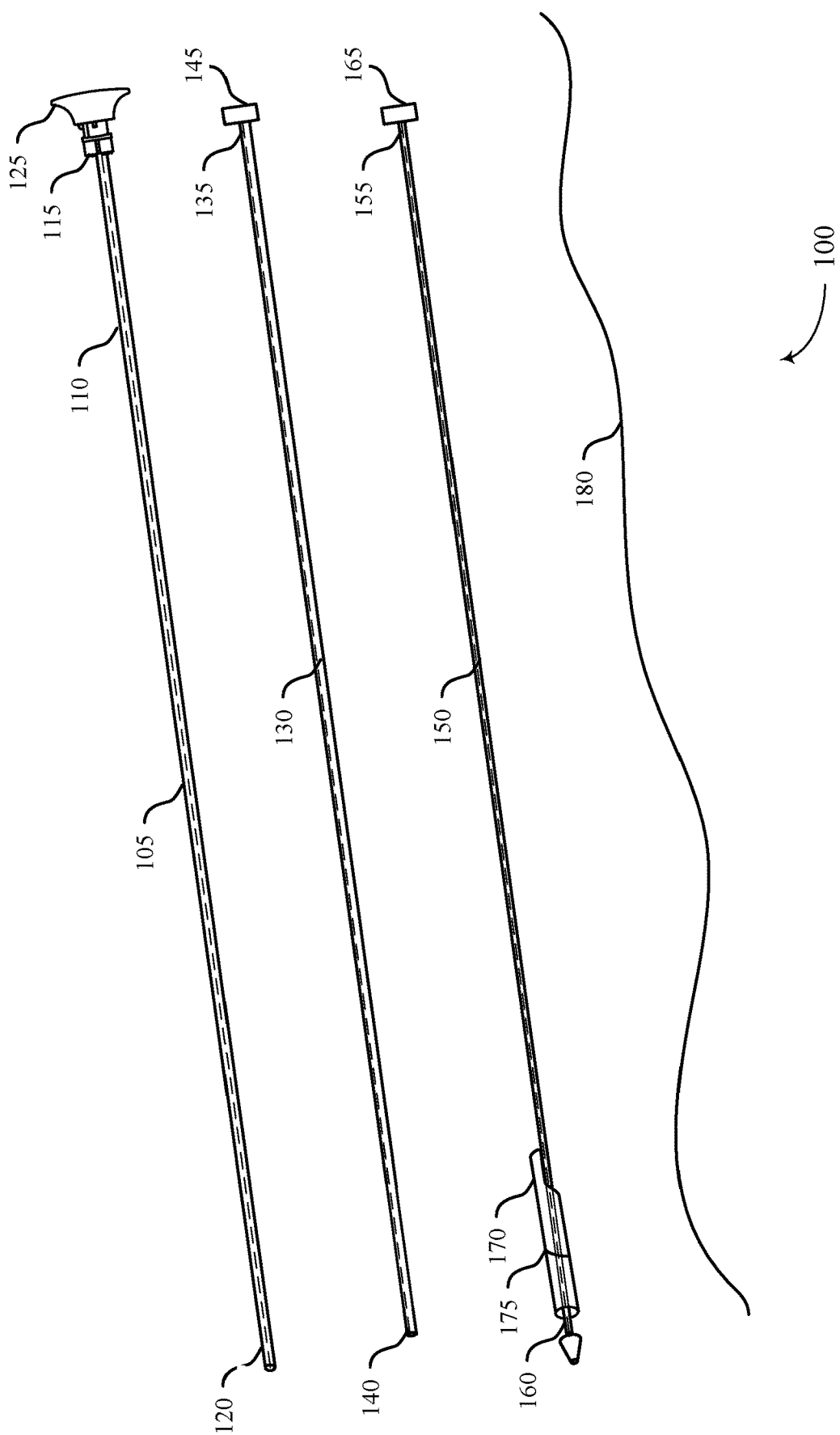
FIG. 1 illustrates an exploded view of a system for providing access to a body lumen in accordance with aspects of the present disclosure.

The present disclosure is generally directed to delivering a stent within a body lumen and covering the access site through which the stent was delivered. In certain procedures described herein, to place a stent within a body lumen, the luminal wall is pierced, and a stent delivery system is advanced through the hole (i.e., access site or access hole) and positioned at the target site (e.g., across an obstruction). The stent is then deployed from the stent delivery system, and the stent delivery system is withdrawn back out of the lumen through the same hole. If the hole is not covered, fluid from the lumen may leak out into the surrounding tissue and organs, which may potentially cause serious discomfort or other medical complications.

In some cases, a proximal portion of the stent may be deployed distal to the access hole. In that case, the delivery system may be retracted thereby pulling the proximal portion of the stent at least partially over the access hole. The stent may be retracted to cover at least a portion of the access hole by pulling on a guidewire lumen. In other examples, the stent may be retracted towards the access hole by pulling on a coupling ring attached to the stent. In some cases, the proximal and distal portions of the stent may be constrained to the guidewire lumen by a constrainment member. The constrainment member may be a filament tied around the stent, a wire wrapped around the stent, a wire frame partially wrapped around the stent, a splittable sheath, or some combination of these elements. In some examples, the remaining distal portion of the stent may be deployed to fully expand the stent within the body lumen by pulling the constrainment member in a proximal direction.

In some examples, the proximal portion of the stent may be constrained to the guidewire lumen via the constrainment member prior to pulling the proximal portion of the stent behind the access hole. After the proximal portion of the stent at least partially covers the access hole, the proximal portion of the stent may be deployed by pulling the constrainment member in a proximal direction thereby releasing the constrainment member from around the proximal portion of the stent.

In other examples, a distal portion of the stent may be deployed distal to the access hole. After the stent is placed within the body lumen, an outer sheath may be retracted to deploy the distal portion of the stent within the body lumen. The outer sheath may be retracted toward the access hole while maintaining the proximal portion of the stent within the outer sheath. To deploy the proximal portion of the stent within the body lumen, an internal pusher may be advanced through the outer sheath to push the proximal portion of the stent form the outer sheath. The proximal portion of the stent may compress against the deployed distal portion of the stent within the body lumen. In that case, the proximal portion of the stent may expand in a proximal direction by bouncing back after the proximal portion of the stent fully exits the outer sheath. The proximal portion of the stent may at least partially cover the access site upon expanding within the body lumen.

In some examples, the proximal portion of the stent may be repositioned to cover the access hole prior to retracting the stent towards the access hole. For example, the proximal portion of the stent, when deployed, may initially be positioned towards the access site such that the proximal portion may catch on the wall of the body lumen or access hole upon proximal retraction. To prevent this, the proximal portion of the stent may be repositioned within the body lumen to rotate the proximal portion of the stent away from the access hole. The proximal portion of the stent may be rotated away from the access hole by attaching the stent to one or more positioning members disposed along the guidewire lumen. As the guidewire lumen is retracted towards the access hole, the positioning members may rotate about the guidewire lumen thereby rotating the stent attached to the positioning members. In some cases, a stationary portion of the guidewire lumen may be attached to a rotatable portion of the guidewire lumen via a coupler. In that case, the stent may be attached to the rotatable portion of the guidewire lumen such that when the stent is retracted towards the access hole, the rotatable portion of the guidewire lumen rotates the proximal portion of the stent away from the access hole.

In some cases, the proximal portion of the stent may be repositioned within the body lumen by including one or more positioning members within the outer sheath. For example, the outer sheath may include an extrusion stripe, one or more wires, or a spline abutted by one or more laser cuts. The proximal portion of the stent may be positioned 180 degrees opposite the portion of the outer sheath that includes the positioning members. The positioning members may have a higher stiffness than the portions of the outer sheath without the positioning members. For example, the portions with the positioning members may align to the lesser curvature of the bile duct (e.g., will adopt the path of least resistance in bending). If the proximal portion of the stent positioned opposite of the positionings members, the proximal portion of the stent may expand along the outer radius of the curvature of the bile duct after the outer sheath is retracted.

Embodiments of the present disclosure are now described in detail with reference to the drawings. As used herein, the term "clinician" refers to a doctor, surgeon, nurse, or any other care provider and may include support personnel. The term "proximal" will refer to the portion of the device or component thereof that is closer to the clinician and the term "distal" will refer to the portion of the device or component thereof that is farther from the clinician.

FIG. 1 illustrates an exploded view of a system 100 for providing access to a body lumen and delivering a stent in accordance with aspects of the present disclosure. The system 100 generally includes an outer sheath 105, a lumen member 130, a guidewire lumen 150, a stent 170, and a guidewire 180. The system 100 can be provided as individual components, selectively combined components, or all together as a kit of components. The outer sheath 105 may be inserted into a handle assembly (not pictured) until the outer sheath hub 125 abuts against the proximal end of the handle assembly. Once assembled, the outer sheath 105 extends through the handle assembly to the target body lumen.

During a luminal access and stent delivery procedure, the outer sheath 105 may access the target lumen by piercing a wall of the lumen, for example. In some examples, a sharpened stylet may be used in conjunction with the outer sheath 105 to facilitate piercing the luminal wall. For example, the sharpened stylet may be advanced through the outer sheath 105 until it protrudes from the outer sheath 105 to pierce tissue. Once the outer sheath 105 has accessed the lumen, the guidewire 180 may be advanced through the outer sheath 105 and into the lumen. After correct placement of the guidewire 180 inside the body lumen, the guidewire lumen 150 may be advanced over the guidewire 180 and into the body lumen. The guidewire lumen 150 may be operatively coupled with the expandable stent 170. As such, the guidewire lumen 150 and stent 170 may be advanced over the guidewire 180 and into the body lumen. The guidewire lumen 150 may be proximally retracted to position the stent 170 to cover the access site of the body lumen. As discussed in more detail below, the stent 170 may be attached to the guidewire lumen 150 via a primary constrainment member 175.

The system 100 may be used to access and provide treatment to one or more body lumens within the gastrointestinal system or pancreaticobiliary system, for example. It may be appreciated that the system 100 may also be used to provide access or treatment to other organs or luminal systems within the body such as the arterial system, the bronchial system, the urinary system, or any other luminal system were maneuverability and accuracy is desirable.

In some examples described herein, the handle assembly is coupled with an endoscope and the outer sheath 105 is guided via endoscopic ultrasound (EUS) to provide access to one or more body lumens or organs associated with the pancreaticobiliary system for the purpose of providing treatment. For example, the system 100 may be configured to provide access to at least the common biliary duct to facilitate subsequent procedures to treat narrowed areas or blockages within the bile duct, including palliative drainage procedures. In accordance with various embodiments, the system 100 may be used to perform an Endoscopic Ultrasound Guided Biliary Drainage (EUS-BD) procedure. In a particular embodiment, a palliative drainage procedure may be performed in antegrade fashion in conjunction with the access system 100.

The outer sheath 105 of the system 100 has an elongate tubular body and an internal lumen 110 extending from its proximal end 115 to the distal end 120. In general, the outer sheath 105 is configured to access a body lumen (e.g., by piercing a luminal wall) and to provide a conduit through which one or more devices (e.g., a guidewire 180) may pass to facilitate subsequent treatment of the body lumen or associate organs. As described with reference to several embodiments, the outer sheath 105 may include features that facilitate the direction-controlled delivery of a guidewire 180 within the body lumen for subsequent delivery of a stent 170, a biopsy device, a medicinal delivery element, or any number of other treatment or diagnostic devices.

The lumen member 130 is generally an elongate, tubular member with proximal end 135 and distal end 140 and is dimensioned to be advanced through the internal lumen 110 of the outer sheath 105. The lumen member 130 may also include a hub 145 coupled with the proximal end 135 of the lumen member 130 to facilitate longitudinal manipulation of the lumen member 130 with respect to the outer sheath 105. In certain embodiments, the lumen member 130 includes one or more internal lumens extending from the proximal end 135 to the distal end 140. As described below, the lumen member 130 is configured to house the guidewire lumen 150 and one or more tethers associated with the primary constrainment member 175. In some cases, the lumen member 130 is configured to house the guidewire lumen 150 and the one or more tethers are positioned between an outside surface of the lumen member 130 and an inside surface of the outer sheath 105.

The guide wire lumen 150 is generally an elongate, tubular member with proximal end 155 and distal end 160 and is dimensioned to slidably advance through the internal lumen of the lumen member 130 and over the guidewire 180. The guidewire lumen 150 may also include a hub 165 coupled with the proximal end 155 of the guidewire lumen 150 to facilitate longitudinal or rotational manipulation of the guidewire lumen 150 with respect to the outer sheath 105. In certain embodiments, the distal end 160 of the guidewire lumen 150 includes a tip or bulged portion. In some cases, the distal end 160 may include an ablation element coupled to the tip or bulged portion. As described below, the stent 170 may be coupled to the guidewire lumen 150. For example, the stent 170 may be in a side-saddle configuration, where the guidewire lumen 150 does not extend through the lumen of the stent 170, but rather where the guidewire lumen 150 is positioned outside of the stent 170. In some examples, the stent 170 may be concentric with the guidewire lumen 150. As such, the guidewire lumen 150 may extend through the lumen of the stent 170. The stent 170 may be coupled to the guidewire lumen 150 in a combination of the side-saddle or concentric configurations (e.g., partially side-saddle and partially concentric).

As discussed in more detail below, the stent 170 may be releasably coupled with the guidewire lumen 150 by a primary constrainment member 175. In some examples, the primary constrainment member 175 may be an example of a filament tied around the stent 170, a wire wrapped around the stem 170, a wire frame at least partially wrapped around the stent 170, a splittable sheath, or a combination thereof.

The guidewire 180 is generally a flexible elongate member configured to slidably advance through the internal lumen of the guidewire lumen 150. The guidewire 180 may be uniform in size and stiffness along its entire length, or alternatively, may include sections of differing stiffness.

Figure 2A:
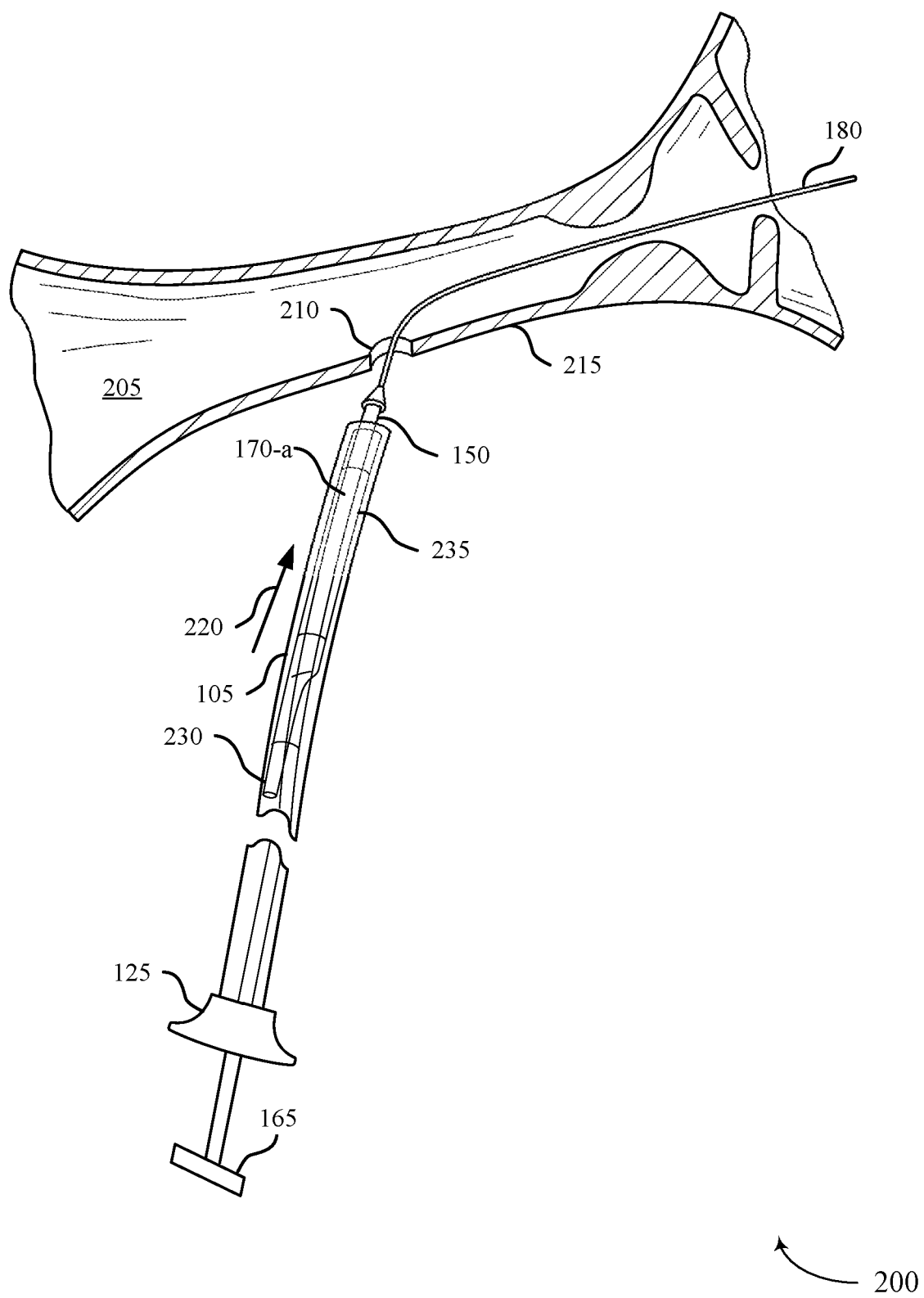
FIG. 2A illustrates a stent delivery system in accordance with aspects of the present disclosure.

FIG. 2A illustrates a stent delivery system 200 in accordance with aspects of the present disclosure. The stent delivery system 200 may be configured to place a stent 170-a within a body lumen 205 to restore luminal flow across narrowed areas or blockages within the body lumen 205. The stent delivery system 200 may be sized or otherwise adapted to place a stent 170-a within any body lumen 205, such as those associated with the pancreaticobiliary system, the arterial system, the bronchial system, the urinary system, or any other luminal system that may require stent treatment. The stent delivery system 200 may generally include the outer sheath 105, the guidewire lumen 150, and the guidewire 180, which may be examples of the corresponding components described with reference to FIG. 1. The guidewire 180 may be part of the stent delivery system 200 or may be a separate component. The stent delivery system 200 can be provided as individual components, selectively combined components, or all together as a kit of components.

The guidewire lumen 150 may generally be a tubular structure that is sized to deploy the stent 170-a within the body lumen 205. The guidewire lumen 150 may access the human body through the working channel of an endoscope, for example, as described with reference to FIG. 1. As will be appreciated, the guidewire lumen 150 may be made from any number of biocompatible materials or combinations of materials suitable for medical sheaths, catheters, and the like.

In general, a stent 170-*a* is a frame or scaffolding structure sized for placement within a body lumen 205 and configured to provide structural support to the inner surface of the body lumen 205. A stent 170-*a* may be used to restore patency across narrowed or blocked areas within the body lumen 205 due to inflammation, tumors, plaque buildup, or any other obstructive feature. Although references to the pancreaticobiliary system are provided herein, it should be appreciated that the stents described herein may be used in any body lumen 205. Furthermore, as discussed in more detail below, the stent 170-*a* may be disposed around the guidewire lumen 150. As such, the stent 170-*a* may be positioned over the access site 210 by retracting the guidewire lumen 150.

The stent 170-*a* may be made from any number of materials, combinations of materials, and constructions. In some examples, the stent 170-*a* is a self-expanding stent. The stent 170-*a* may be a braided stent made from a plurality of wires joined together in a cross-hatch configuration. However, it should be appreciated that the stent 170-*a* may be made from other stent constructions or combinations of stent constructions. In other examples, the stent 170-*a* is a laser-cut stent formed from a single metallic tube with regions cut away for increased flexibility. In yet other examples, the stent 170-*a* is a wire-form stent formed by one or more helically wrapped wires. It may be appreciated that the different stent constructions may exhibit particular characteristics such as radial expansive force, flexibility, reduced foreshortening, or migration resistance that may render a certain construction advantageous for a particular use.

The individual wires or frame of the stent 170-*a* may be made from any number of metallic materials including, but not limited to, titanium, nitinol, or stainless steel. It should be appreciated that other metallic or non-metallic materials may be used to construct the stent 170-*a* that provides suitable flexibility, stiffness, and biocompatibility. The stent 170-*a* may include a polymeric or fabric sleeve that covers some or all of the surface of the stent 170-*a*. Such a sleeve may protect the inner surface of the body lumen 205 from the bare metal of the stent 170-*a* and may prevent tissue ingrowth. In some examples, the stent 170-*a* is a drug-eluting stent.

Referring still to FIG. 2A, to place the stew delivery system 200 within the body lumen 205, an access site 210 is formed through the wall 215 of the body lumen 205, and the guidewire 180 is then advanced through the access site 210 and into the body lumen 205. Once the guidewire 180 is in place, the guidewire lumen 150 is advanced distally, as indicated by arrow 220, over the guidewire 180, through the access site 210, and into the body lumen 205.

In some cases, the stent 170-*a* may be partially disposed around the guidewire lumen 150. For example, the guidewire lumen 150 may be outside the stent 170-*a* along a proximal portion 230 of the stent 170-*a*, and the guidewire lumen 150 may be inside the stent 170-*a* along a distal portion 235 of the stent 170-*a*. This configuration may be referred to as a partial side-saddle configuration.

Figure 2B:
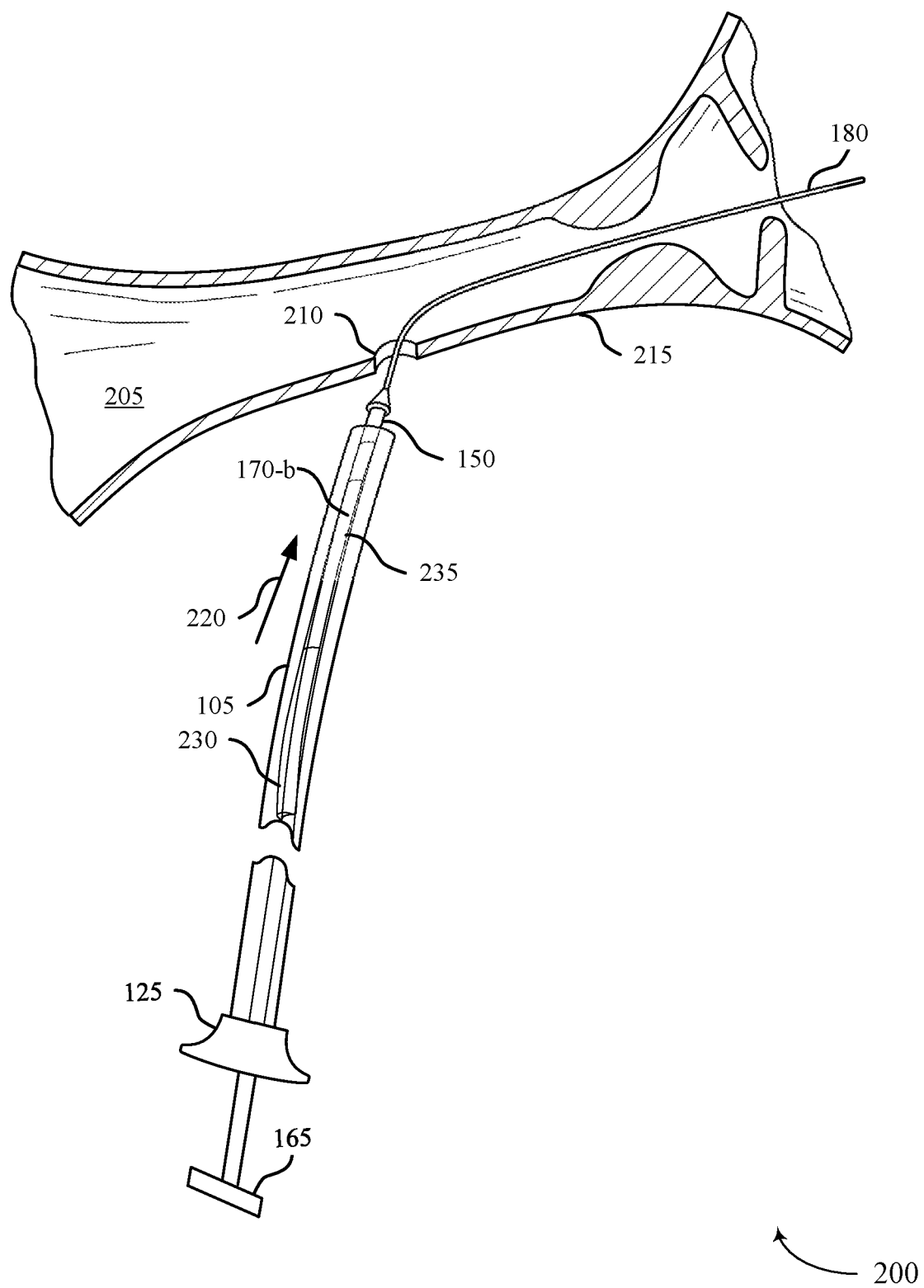
FIG. 2B illustrates a stent delivery system in accordance with aspects of the present disclosure.

FIG. 2B illustrates a stent delivery system 200 in accordance with aspects of the present disclosure. The stent delivery system 200 may be configured to place a stent 170-*b* within a body lumen 205 to restore luminal flow across narrowed areas or blockages within the body lumen 205 and may generally include the components as described with reference to FIG. 2A.

In the example illustrated in FIG. 2B, the stent 170-*b* may be fully disposed around the guidewire lumen 150. For example, the stent 170-*b* may be fully disposed around the guidewire lumen 150 such that the guidewire lumen 150 is outside the stent 170-*b* along the proximal portion 230 and the distal portion 235 of the stent 170-*b*. This configuration may be referred to as a complete side-saddle configuration, where the guidewire lumen 150 does not extend through the lumen of the stent 170-*b*.

Figure 2C:
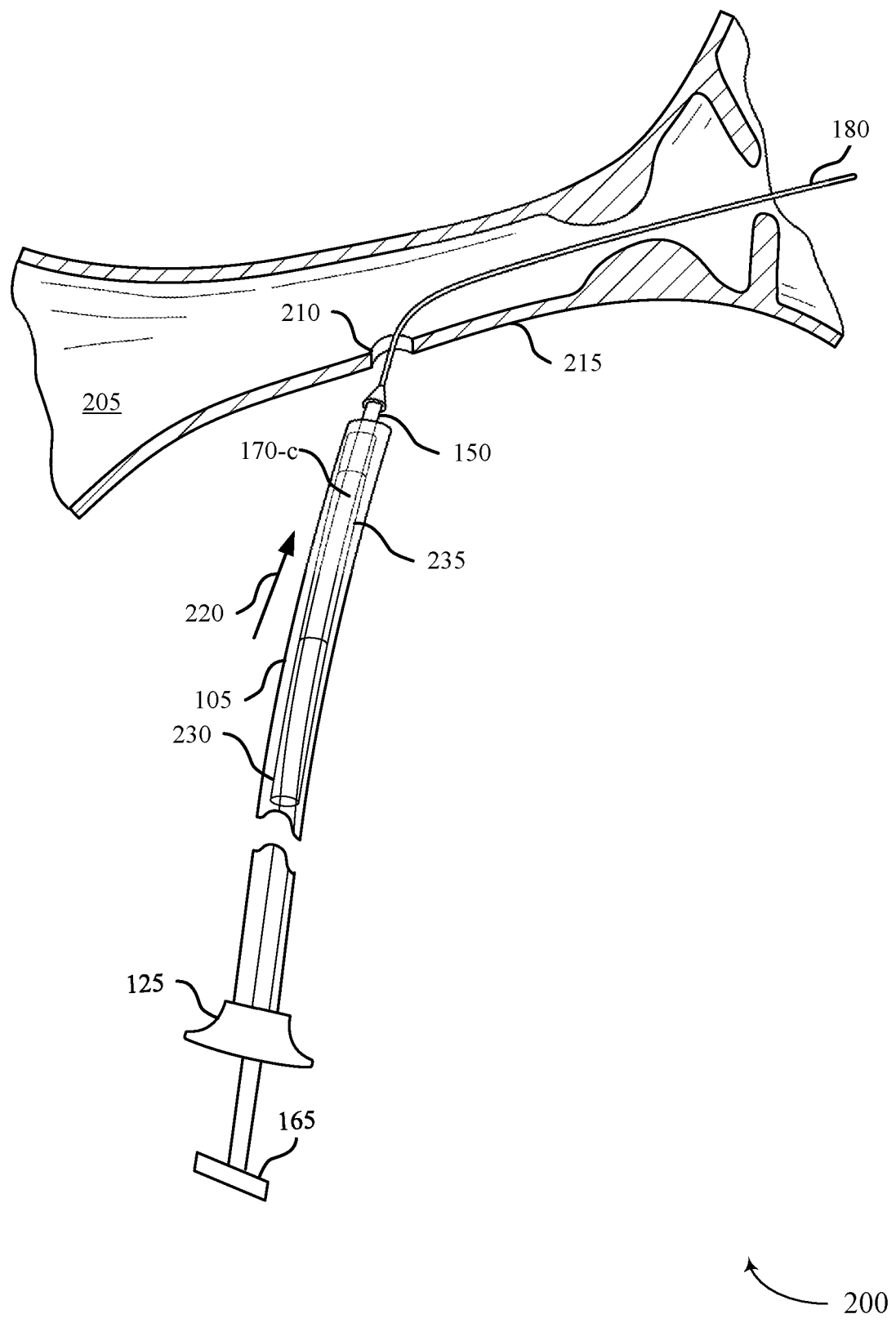
FIG. 2C illustrates a stent delivery system in accordance with aspects of the present disclosure.

FIG. 2C illustrates a stent delivery system 200 in accordance with aspects of the present disclosure. The stent delivery system 200 may be configured to place a stent 170-*c* within a body lumen 205 to restore luminal flow across narrowed areas or blockages within the body lumen 205 and may generally include the components as described with reference to FIG. 2A.

In the example illustrated in FIG. 2C, the stent 170-*c* may be fully disposed around the guidewire lumen 150. In that case, the guidewire lumen 150 may be inside the stent 170-*c* along the proximal portion 230 and the distal portion 235 of the stent 170-*c*. This configuration may be referred to as concentric, where the stent 170-*c* may be concentric with the guide wire lumen 150 and extend through the lumen of the stent 170-*c*.

Figure 2D:
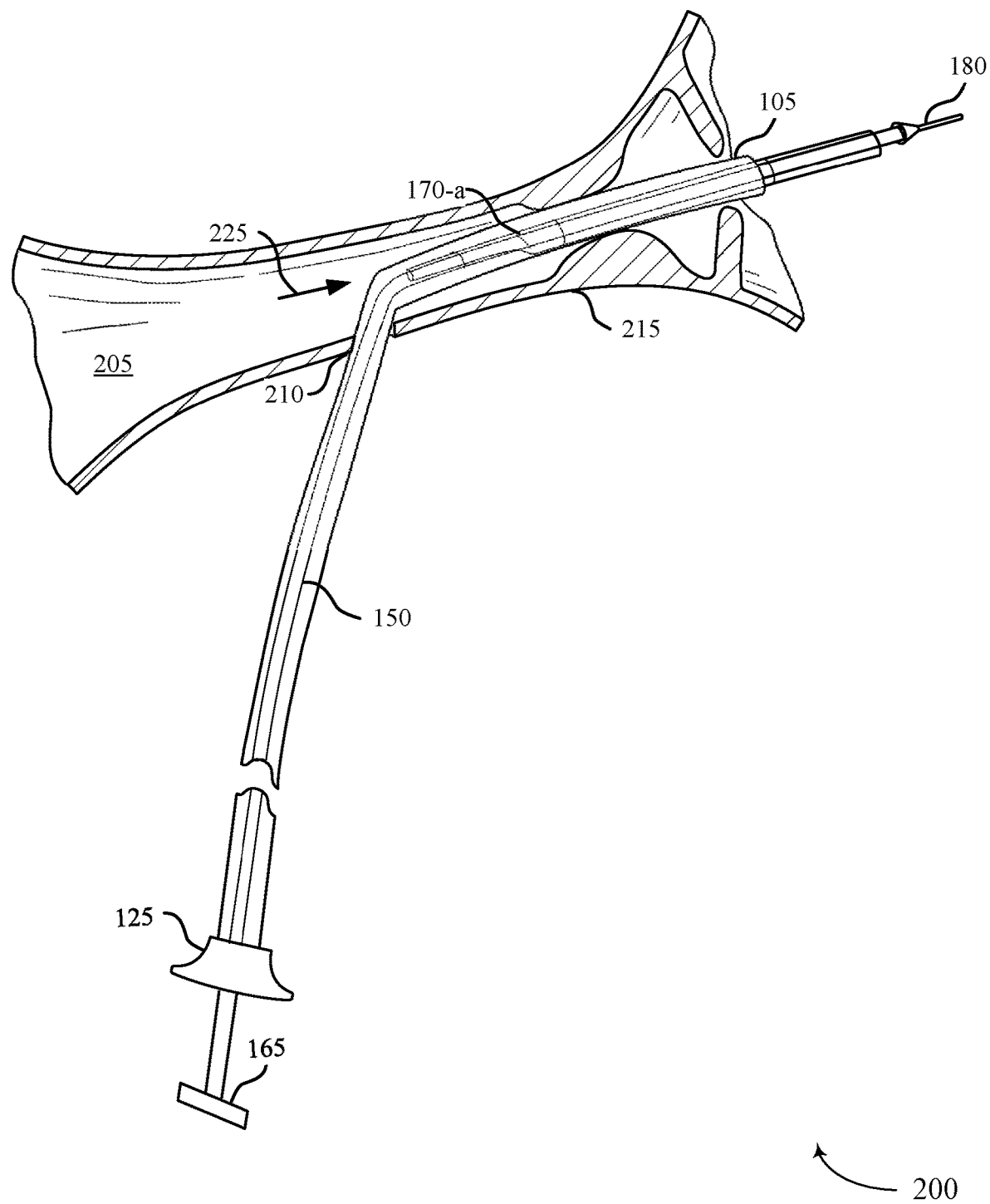
FIG. 2D illustrates a stent delivery system within a body lumen in accordance with aspects of the present disclosure.

FIG. 2D illustrates a stent delivery system 200 within the body lumen 205 in accordance with aspects of the present disclosure. Once in the body lumen 205, the outer sheath 105, the guidewire lumen 150, and the lumen member (not shown) may be advanced distally, as indicated by arrow 225. For example, the outer sheath 105 may be advanced distally by pushing the outer sheath hub 125 in a distal direction, and the guidewire lumen 150 may be advanced distally by pushing the hub 165 in a distal direction. In some cases, the outer sheath 105 and the guidewire lumen 150 may be advanced distally such that the outer sheath 105 and the guidewire lumen 150 extend through the papilla and into the duodenum. The outer sheath 105 may be disposed around the guidewire lumen 150. As such, the stent 170-*a* may be disposed between the guidewire lumen 150 and an inner surface of the outer sheath 105. In some cases, the access site 210 may be uncovered by the stent 170-*a*.

Figure 2E:
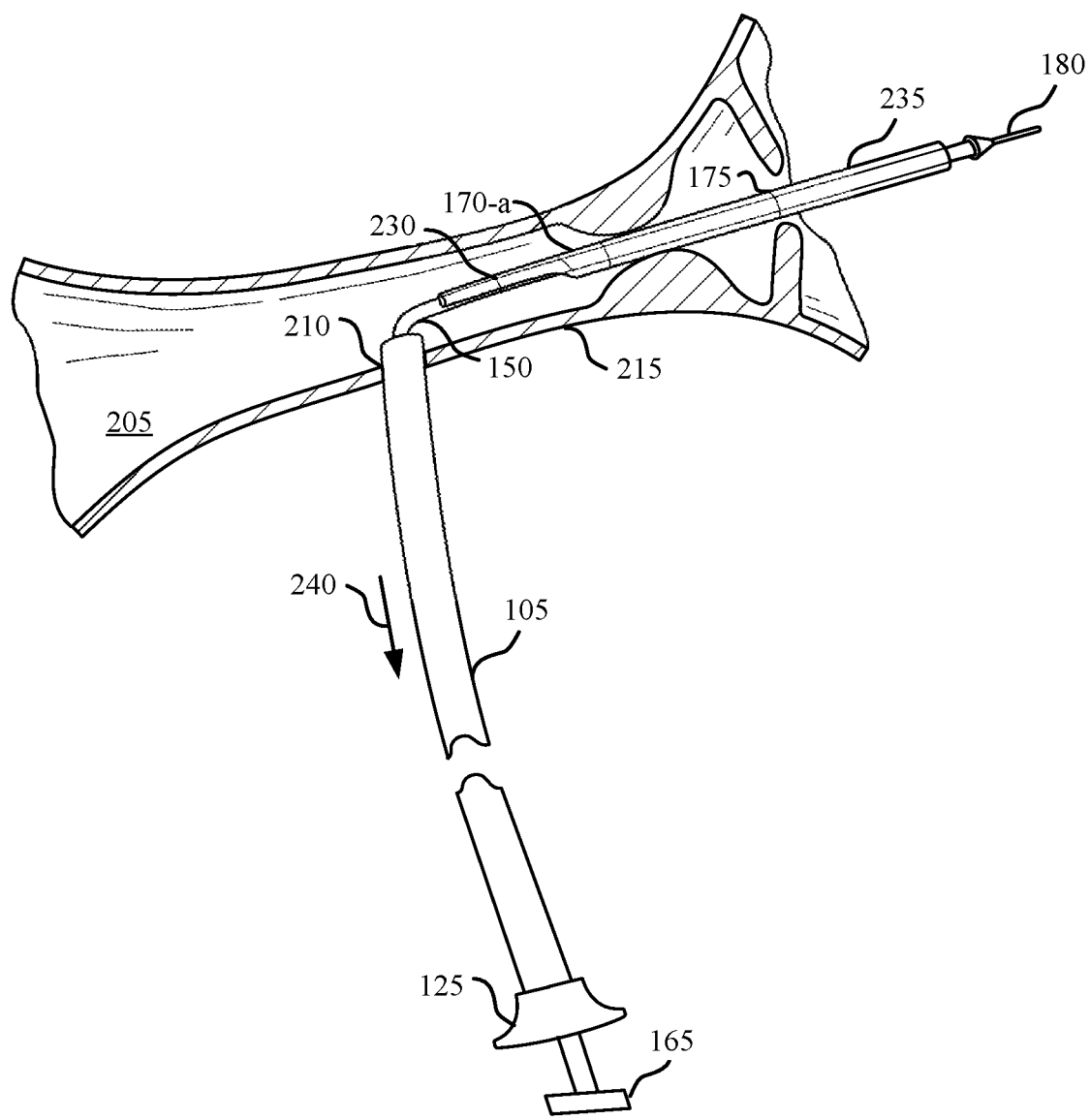
FIG. 2E illustrates a stent delivery system with an outer sheath removed in accordance with aspects of the present disclosure.

FIG. 2E illustrates a stent delivery system 200 with the outer sheath 105 removed in accordance with aspects of the present disclosure. As the outer sheath 105 is withdrawn proximally, as indicated by arrow 240, the lumen member (not shown) may remain stationary, and the stent 170-*a* may be exposed within the body lumen 205. The outer sheath 105 may be withdrawn proximally by pulling the outer sheath hub 125 in a proximal direction. In some cases, the outer sheath 105 may be re-advanced distally to cover the stent 170-*a* if repositioning is required. Once the desired anatomical position of the stent 170-*a* has been achieved within the body lumen 205, the outer sheath 105 may be retracted.

As discussed in more detail below, the stent 170-*a* may be releasably coupled with the guidewire lumen 150 by a primary constrainment member 175. In some examples described below in more detail, the primary constrainment member 175 may be an example of a filament tied around the stent 170-*a*, a wire wrapped around the stent 170-*a*, a wire frame at least partially wrapped around the stent 170-*a*, a splittable sheath, or a combination thereof.

Figure 2F:
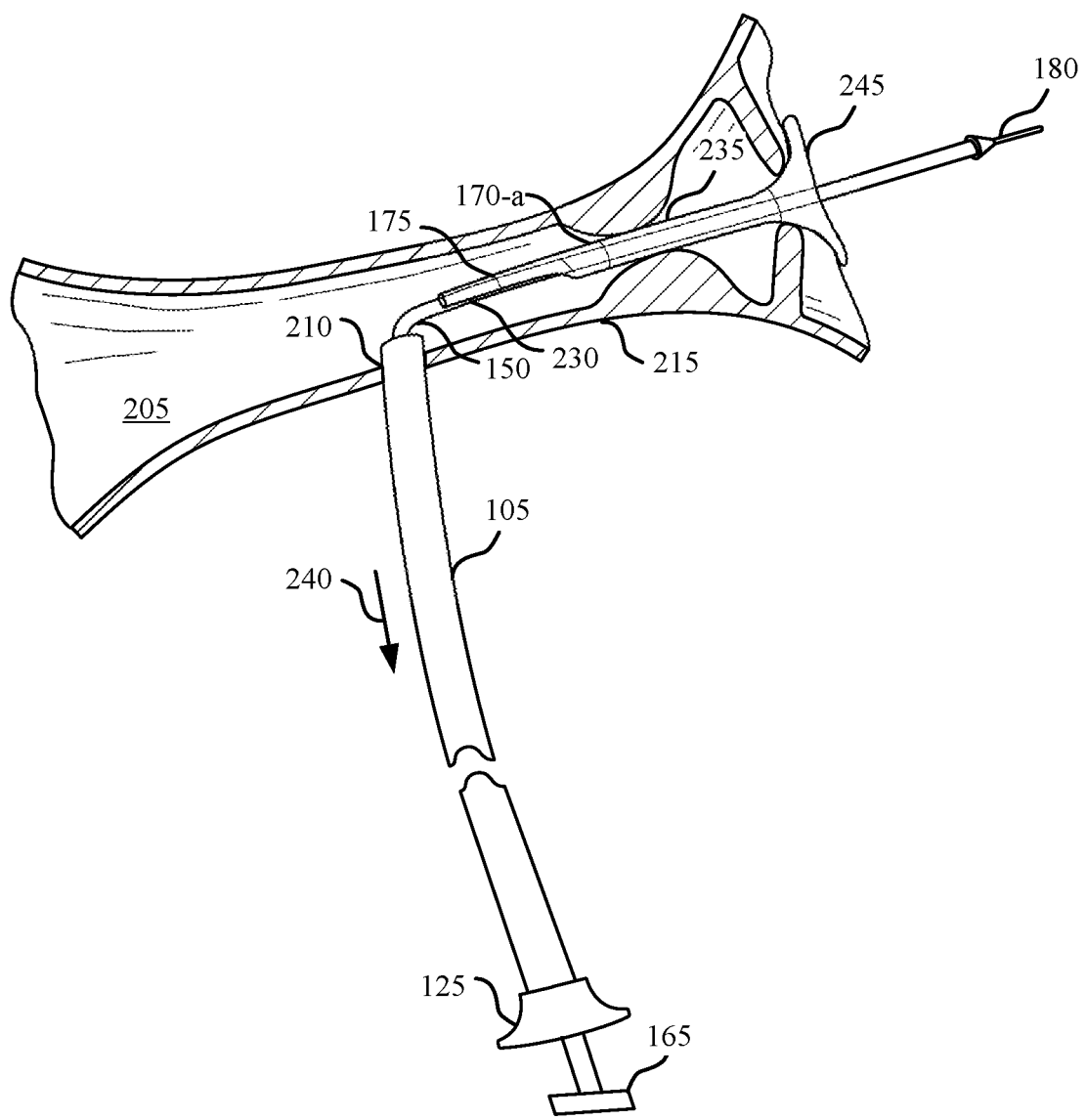
FIG. 2F illustrates a stent delivery system with a flanged portion of the stent deployed in accordance with aspects of the present disclosure.

FIG. 2F illustrates a stent delivery system 200 with a flanged portion 245 of the stent 170-*a* deployed in accordance with aspects of the present disclosure. As the outer sheath 105 is withdrawn proximally, as indicated by arrow 240, the stent 170-*a* may be exposed within the body lumen 205. In some cases, the stent 170-*a* may be advanced such that at least a portion of the stent 170-a extends through the papilla and into the duodenum. As the outer sheath 105 is removed through the access site 210, the distal portion 235 of the stent 170-a expands to expose the flanged portion 245.

As the stent 170-a is pulled in a proximal direction, the flanged portion 245 of the stent 170-a contacts the papilla. In that case, the flanged portion 245 prevents the stent 170-a from being further withdrawn in a proximal direction. The clinician may be able to feel the resistance of the flanged portion 245 against the papilla and may therefore infer the location of the stent 170-a. Additionally or alternatively, the collapsing of the flanged portion 245 as it is pulled against the papilla may be viewed under fluoroscopy or similar imaging techniques to infer the location of the stent 170-a. In some cases, the stent 170-a may be repositioned within the body lumen 205 based on a distance measurement determined by pulling the stent 170-a until the flanged portion 245 contacts the papilla. For example, if the flanged portion 245 of the stent 170-a contacts the papilla and the measured distance indicates that the access site 210 may be exposed to the body lumen 205 without the stent 170-a covering the access site 210, the stent 170-a may be repositioned. The measured distance may include a distance measured between the proximal portion 230 of the stent 170-a and the access site 210.

Figure 2G:
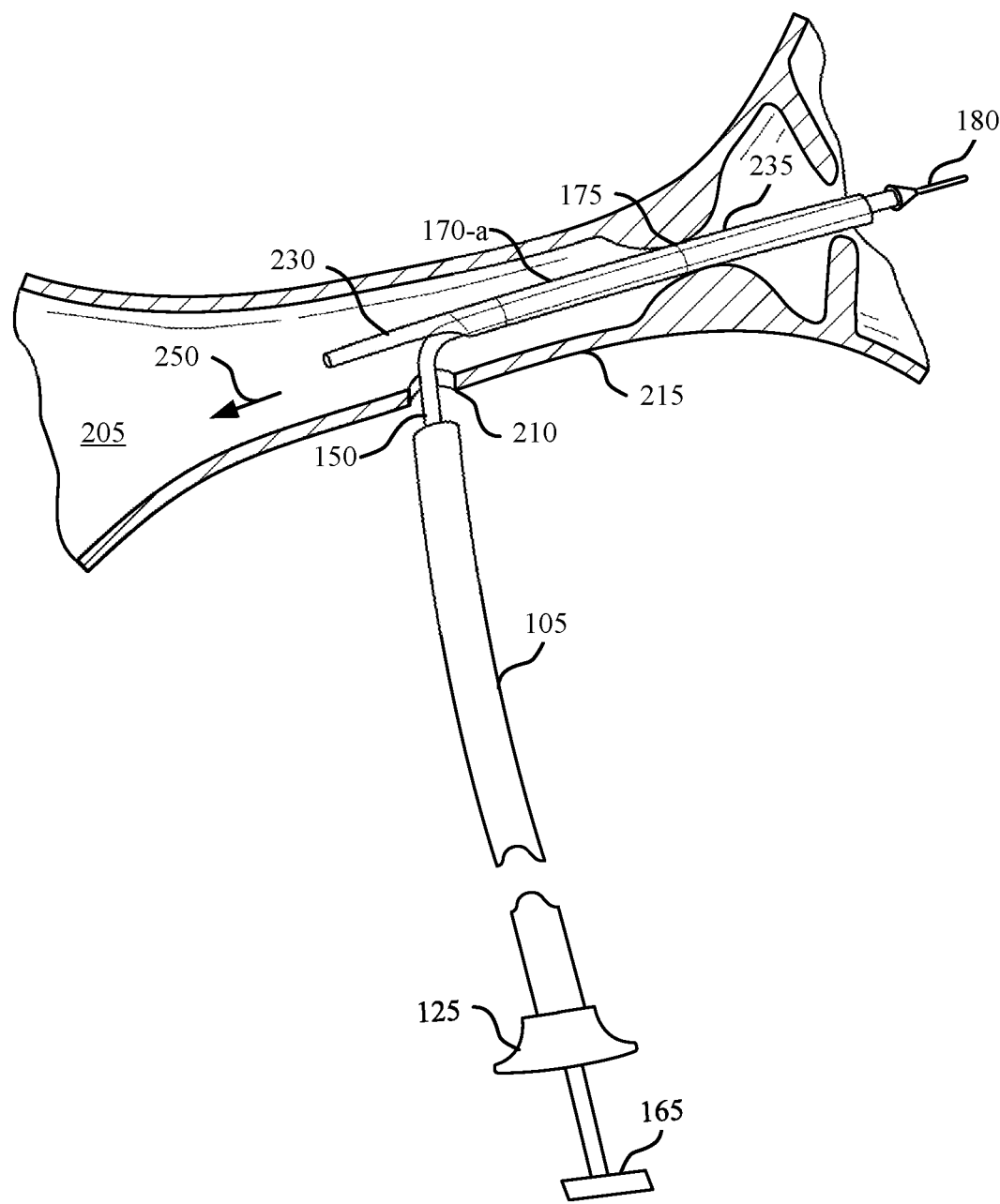
FIG. 2G illustrates a stent delivery system with the stent retracted towards the access site in accordance with aspects of the present disclosure.

FIG. 2G illustrates a stent delivery system 200 with the stein 170-a retracted towards the access site 210 in accordance with aspects of the present disclosure. Once the outer sheath 105 is removed through the access site 210, the stent 170-a may be pulled towards the access site 210 in a proximal direction, as indicated by arrow 250. For example, the stent 170-a may be pulled toward the access site 210 until the proximal portion 230 of the stent 170-a at least partially covers the access site 210. As discussed in more detail below, the stent 170-a may be retracted towards the access site 210 by pulling the guidewire lumen 150 in a proximal direction. For example, the stent 170-a may be pulled towards the access site 210 by pulling the hub 165 of the guidewire lumen 150 in a proximal direction. In some cases, the stent 170-a may be pulled towards the access site 210 by pulling the hub 165 of the guidewire lumen 150, the lumen member, and the outer sheath hub 125 of the outer sheath 105. Furthermore, the stent 170-a may be repositioned within the body lumen 205 to at least partially cover the access site 210.

Figure 2H:
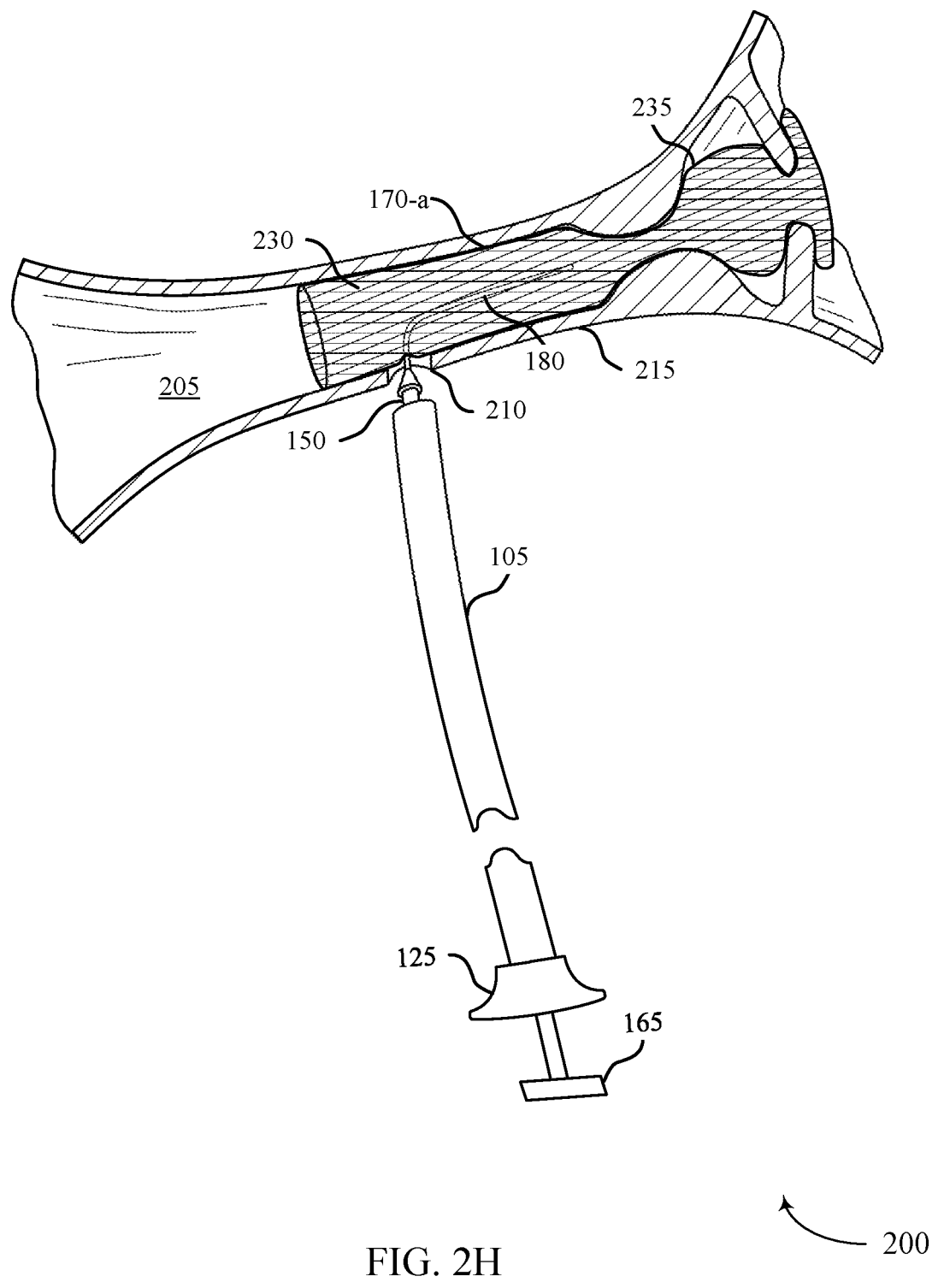
FIG. 2H illustrates a stent delivery system with the stent fully deployed in accordance with aspects of the present disclosure.

FIG. 2H illustrates a stent delivery system 200 with the stent 170-a fully deployed in accordance with aspects of the present disclosure. To deploy the stent 170-a within the body lumen 205, the primary constrainment member may be released. As discussed in more detail below, the stent 170-a may be deployed by pulling the primary constrainment member in a proximal direction, pulling one or more tethers coupled with the primary constrainment member, or both. In the case of a self-expanding stent, the stent 170-a expands to contact the inner surface of the body lumen 205. Once the stent 170-a expands within the body lumen 205, the guidewire lumen 150 and the guidewire 180 are withdrawn through the access site 210. In some cases, the guidewire lumen 150 and the guidewire 180 may extend through a hole in a wall of the stent 170-a. In such cases, the guidewire lumen 150 and the guidewire 180 may be withdrawn through the hole in the wall of the stent 170-a.

Figure 3A:
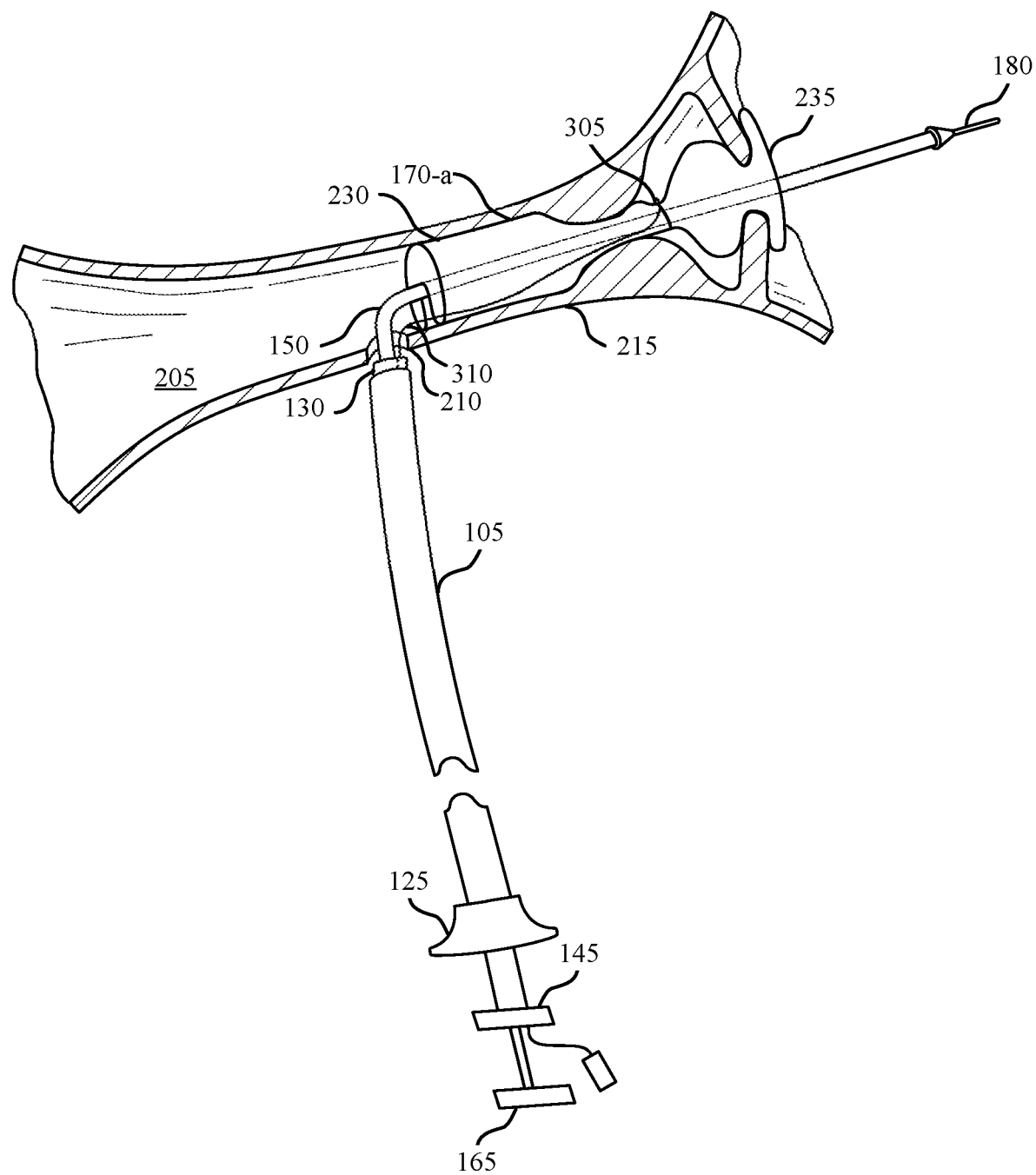
FIG. 3A illustrates a stent delivery system with a filament tied around a stent in accordance with aspects of the present disclosure.

FIG. 3A illustrates a stent delivery system 300 with a filament tied around a stent 170-a in accordance with aspects of the present disclosure. As the outer sheath 105 is removed from the access site 210, the stent 170-a may be exposed within the body lumen 205. For example, the outer sheath 105 may be removed from the access site 210 by withdrawing the outer sheath 105 via the outer sheath hub 125. In some cases, the stent 170-a may be partially disposed around the guidewire lumen 150. This configuration may be referred to as a partial side-saddle configuration.

The stent 170-a may be releasably coupled with the guidewire lumen 150 by a primary constrainment member 305. In some examples, the primary constrainment member 305 may be an example of a filament tied around the stent 170-a. For example, the primary constrainment member 305 may comprise a single wrap tied around the stent 170-a at the proximal portion 230. A tether 310 may be attached to the primary constrainment member 305 and extend through the access site 210. In some cases, the tether 310 may be an extension of the primary constrainment member 305 (e.g., comprising the same material as the primary constrainment member 305 and seamlessly connected to primary constrainment member 305). In other examples, the tether 310 may be attached to the primary constrainment member 305.

The primary constrainment member 305 may be knotted around the proximal portion 230 of the stent 170-a at varying distances from the proximal end of the stent 170-a. For example, the distance between the knot of the primary constrainment member 305 and the proximal end of the stent 170-a may be between a range of 0 to 40 mm. In some examples, the distance between the knot of the primary constrainment member 305 and the proximal end of the stent 170-a may be between a range of 15 to 30 mm. The distance between the knot of the primary constrainment member 305 and the distal end of the lumen member 130 may be between a range of 0 to 40 mm. In some examples, the distance between the knot of the primary constrainment member 305 and the distal end of the lumen member 130 may be between a range of 20 to 30 mm.

In some cases, the guidewire lumen 150 may be outside the stent 170-a along the proximal portion 230 of the stent 170-a (e.g., proximal to the knot), and the guidewire lumen 150 may be inside the stent 170-a along a distal portion 235 of the stent 170-a (e.g., distal to the knot). That is, the stent 170-a may be positioned on the guidewire lumen 150 in a partial side-saddle configuration. In some cases, the knot may be positioned along the proximal portion 230 of the stent 170-a or along the distal portion 235 of the stent 170-a. In some cases, once the outer sheath 105 is withdrawn proximally to expose the stent 170-a, the proximal portion 230 of the stent 170-a may expand. That is, the proximal portion 230 of the stent 170-a may be unconstrained by the primary constrainment member 305. In such cases, the expanded state of the proximal portion 230 of the stent 170-a may be referred to as a cuff.

The primary constrainment member 305 may be knotted around the stent 170-a and the guidewire lumen 150 such that the primary constrainment member 305 is releasable when pulled in a proximal direction. For example, the primary constrainment member 305 may include a loop anchored to the guidewire lumen 150 such that a pulling force of the primary constrainment member 305 is directed along a longitudinal axis of the stent 170-a. Once the primary constrainment member 305 is knotted, the primary constrainment member 305 may be routed in a proximal direction into a first lumen of the lumen member 130. In some cases, the guidewire lumen 150 may be routed through a second lumen of the lumen member 130.

The primary constrainment member 305 may be fabricated from a single filament or multi-filament material. Exemplary materials of the primary constrainment member 305 include, but are not limited to, polyamide, polyester, polypropylene, poly-vinylidene di-fluoride or derivatives thereof. The outer diameter of the filament material may be within a range of 0.05 to 0.025 inches. In some examples, the outer diameter of the filament material within a range of 0.012 to 0.020 inches. The tensile strength of the primary constrainment member 305 (e.g., the tether 310), may be greater than 8 pound-force. In some examples, the tensile strength of the primary constrainment member 305 (e.g., the tether 310), may be greater than 10 pound-force.

In some examples, the primary constrainment member 305 may comprise wire wrapped around the stem 170-*a*. For example, the primary constrainment member 305 be a nitinol or other super-elastic wire filament. In this case, the single filament may be a single or double filament wrap to constrain the stent 170-*a* to the guidewire lumen 150 at a central point. The diameter of the nitinol filament may be within a range of 0.0050 to 0.020 inches. In some examples, the diameter of the nitinol filament may be within a range of 0.0070 to 0.014 inches. The nitinol filament may be coated with a lubricous material such as polytetrafluoroethylene (PTFE), parylene-N or MDX silicone.

Figure 3B:
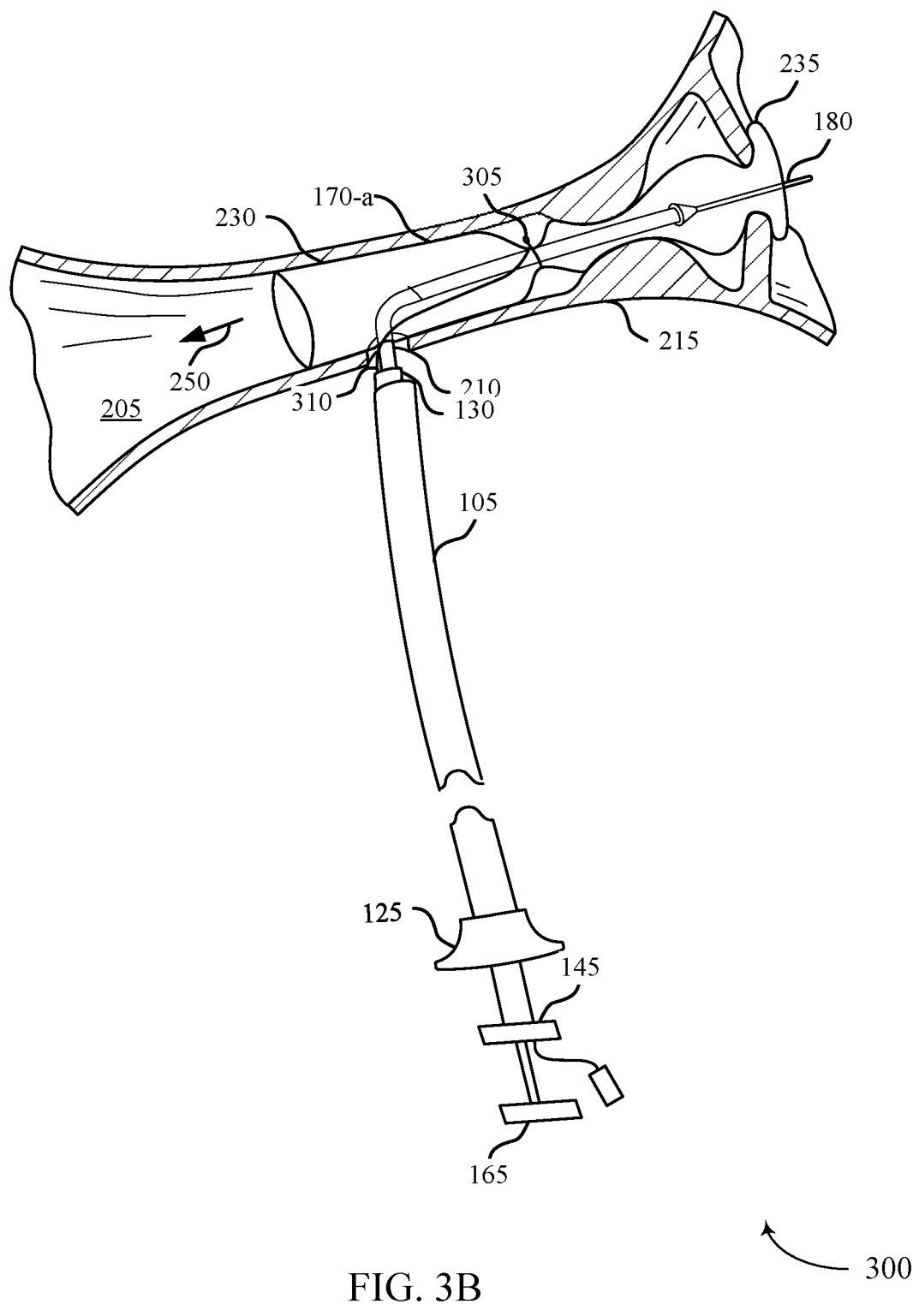
FIG. 3B illustrates a stent delivery system with the stent retracted towards the access site in accordance with aspects of the present disclosure.

FIG. 3B illustrates a stent delivery system 300 with the stent 170-*a* retracted towards the access site 210 in accordance with aspects of the present disclosure. Once the outer sheath 105 is removed through the access site 210, the stent 170-*a* may be pulled toward the access site 210 in a proximal direction, as indicated by arrow 250. For example, the stent 170-*a* may be pulled toward the access site 210 until the proximal portion 230 of the stent 170-*a* at least partially covers the access site 210. The proximal portion 230 of the stent 170-*a* may be tied such that the primary constrainment member 305 prevents the proximal portion 230 from catching on the wall 215 of the body lumen as the stent 170-*a* is retracted. The stent 170-*a* may be retracted towards the access site 210 by pulling the guidewire lumen 150 in a proximal direction. For example, stent 170-*a* may be retracted by pulling the hub 165 of the guidewire lumen 150. As discussed in more detail below, the stent 170-*a* may be repositioned within the body lumen 205 to at least partially cover the access site 210.

Figure 3C:
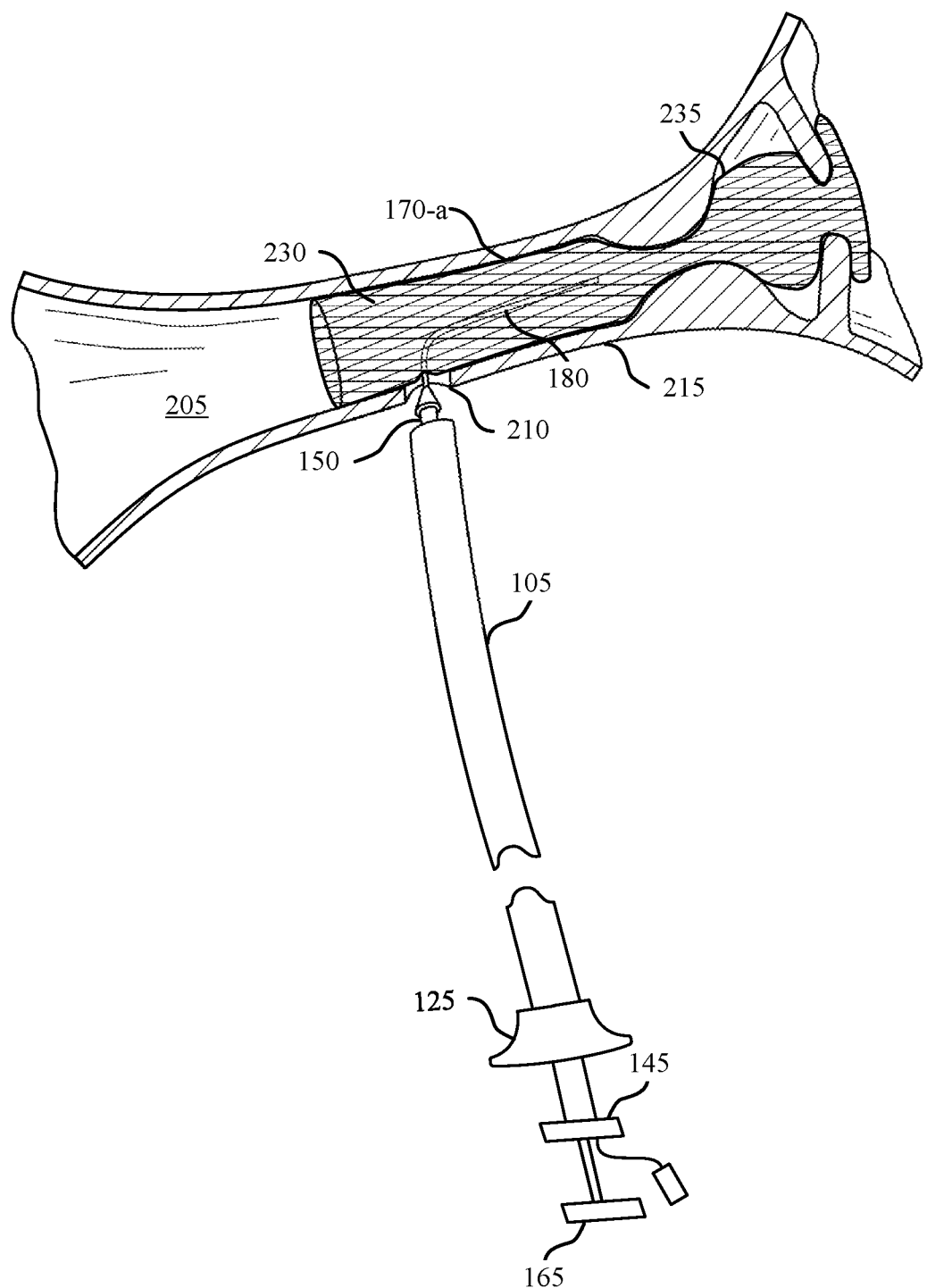
FIG. 3C illustrates a stent delivery system with the stent fully deployed in accordance with aspects of the present disclosure.

FIG. 3C illustrates a stent delivery system 300 with the stent 170-*a* fully deployed in accordance with aspects of the present disclosure. To deploy the stent 170-*a* within the body lumen 205, the primary constrainment member may be released. The stent 170-*a* may be deployed by pulling the primary constrainment member in a proximal direction. For example, the stent 170-*a* may be deployed by pulling the tether coupled with the primary constrainment member. In that case, the knot may unravel to deploy the stent 170-*a*. In some cases, the pulling force of the primary constrainment member may be directed along a longitudinal axis of the stent 170-*a* such that the loop anchored to the guidewire lumen 150 may unfasten. In the case of a self-expanding stent, the stent 170-*a* expands to contact the inner surface of the body lumen 205. Once the stent 170-*a* expands within the body lumen 205, the guidewire lumen 150, the guidewire 180, the primary constrainment member, and the tether are withdrawn through the access site 210.

Figure 4A:
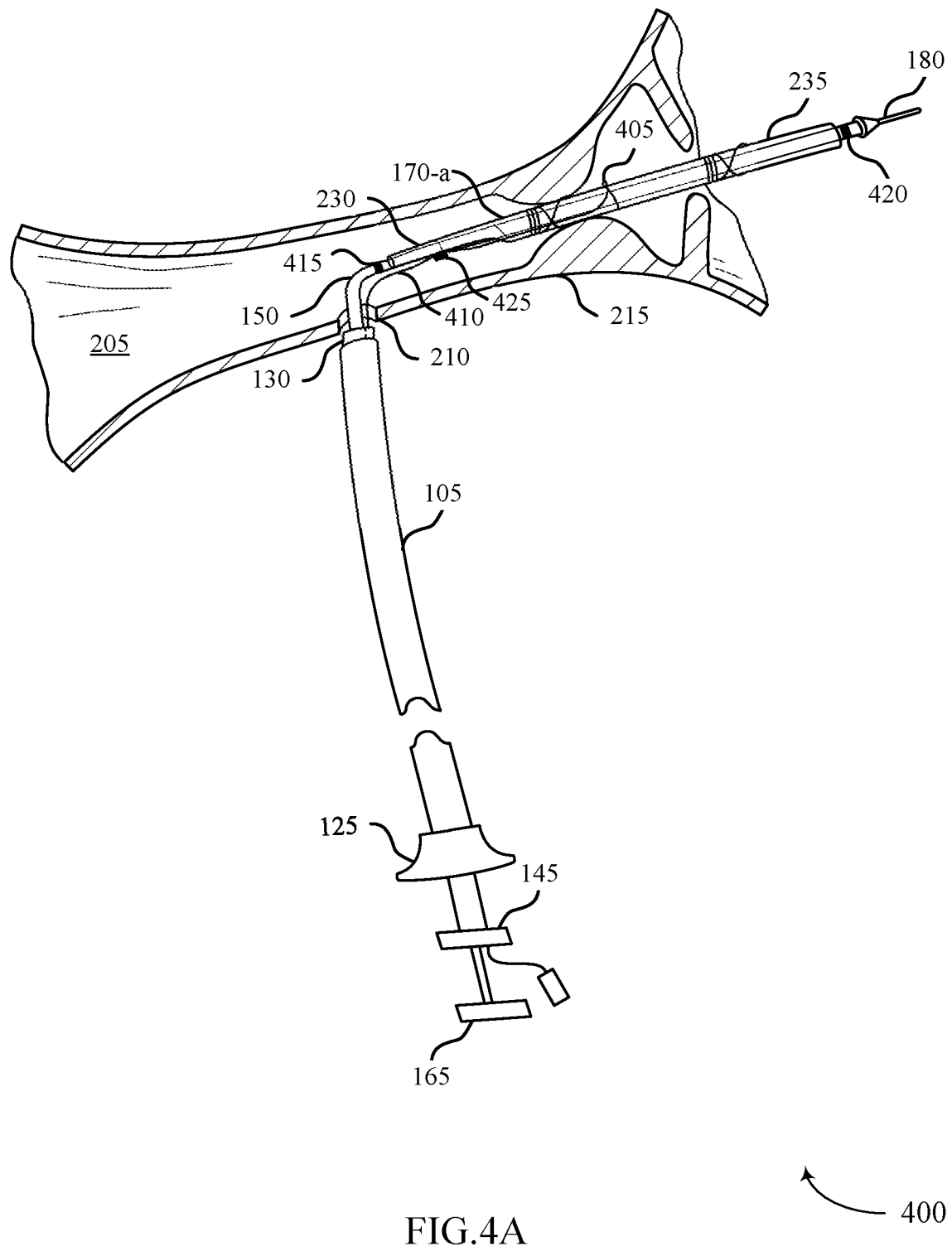
FIG. 4A illustrates a stent delivery system with one or more filaments tied around a stent in accordance with aspects of the present disclosure.

FIG. 4A illustrates a stent delivery system 400 with one or more knots tied around a stent 170-*a* in accordance with aspects of the present disclosure. As the outer sheath 105 is removed from the access site 210, the stent 170-*a* may be exposed within the body lumen 205. The stent 170-*a* may be disposed around the guidewire lumen 150 in the partial side-saddle configuration.

The stent 170-*a* may be releasably coupled with the guidewire lumen 150 by a primary constrainment member 405. In some examples, the primary constrainment member 405 may be an example of one or more knots tied around the stent 170-*a*. For example, the primary constrainment member 405 may comprise one or more wraps tied around the stent 170-*a* at spaced intervals along the distal portion 235 of the stent 170-*a*. In that case, the stent 170-*a* may be constrained to the guidewire lumen 150 by a series of circumferential wraps, windings, suture knots, or a combination thereof. In other examples, the primary constrainment member 405 may comprise one or more wraps tied around the stent 170-*a* at spaced intervals from the distal portion 235 to the proximal portion 230 of the stent 170-*a*.

In some examples, the primary constrainment member 405 may comprise a filament wrap around the proximal portion 230 of the stent 170-*a*. The filament wrap may be an example of a single wrap, winding, or suture knot. In that case, the proximal portion 230 of the stent 170-*a* may be tied such that the primary constrainment member 405 prevents the proximal portion 230 from catching on the wall 215 of the body lumen 205 as the stent 170-*a* is retracted. In some cases, once the outer sheath 105 is withdrawn proximally to expose the stent 170-*a*, the proximal portion 230 of the stent 170-*a* may expand. That is, the proximal portion 230 of the stent 170-*a* may be unconstrained by the primary constrainment member 405.

The primary constrainment member 405 may be knotted at spaced intervals around the stent 170-*a* and the guidewire lumen 150 such that the primary constrainment member 405 is releasable when pulled in a proximal direction. For example, the primary constrainment member 405 may include one or more loops anchored to the guidewire lumen 150 such that a pulling force of the primary constrainment member 405 is directed along a longitudinal axis of the stent 170-*a*. In that case, the primary constrainment member 405 may include an additional suture loop, plastic piece, or metal piece to create a center pull point. The center pull point may be anchored to the guidewire lumen 150 at a location between the one or more knots along the distal portion 235 of the stent 170-*a* and the single wrap at the proximal portion 230 of the stent 170-*a*.

The primary constrainment member 405 may be fabricated from a single filament or multi-filament material. Exemplary materials of the primary constrainment member 405 include, but are not limited to, polyamide, polyester, polypropylene, poly-vinylidene di-fluoride or derivatives thereof.

A tether 410 may be attached to the primary constrainment member 405 and extend through the access site 210. In some cases, the tether 410 may be an extension of the primary constrainment member 405 (e.g., comprising the same material as the primary constrainment member 405 and seamlessly connected to primary constrainment member 405). In other examples, the tether 410 may be attached to the primary constrainment member 405. In some cases, one or more tethers 410 may be attached to the primary constrainment member 405. For example, a first tether may be coupled to the distal portion 235 of the stent 170-*a*, and a second tether may be coupled to the proximal portion 230 of the stent 170-*a*. As discussed in more detail below, the first and second tether may be pulled separately to release the proximal portion 230 and the distal portion 235 of the stent 170-*a* at different times.

The stent delivery system 400 may include a proximal marker 415 and a distal marker 420. The proximal marker 415 and the distal marker 420 may be disposed around the guidewire lumen 150. For example, the proximal marker 415 may be positioned at a proximal edge of the stent 170-*a*, and the distal marker 420 may be positioned at the distal edge of the stent 170-*a*. The proximal marker 415 and the distal marker 420 may assist the clinician in stent placement under fluoroscopy, prior to deploying the stent 170-*a*.

The stent delivery system 400 may include a stent anchor 425. In the constrained state (e.g., before the outer sheath 105 is removed), a distal portion 235 of the stent 170-*a* may be constrained between the stent anchor 425 and the outer sheath 105. In some cases, the stent anchor 425 may route the tether 410 along the distal portion 235 of the stent 170-*a*. The stent anchor 425 may comprise a compressible polymer material configured to adhesively bond to the guidewire lumen 150. In some cases, the stent anchor 425 may be configured to provide a central angle of pull for the tether 410. In other examples, the stent anchor 425 be a strap for the stent 170-*a* when the tether 410 is pulled in a proximal direction.

Once the primary constrainment member 405 is knotted, the primary constrainment member 405 may be routed in a proximal direction into a first lumen of the lumen member 130. In some cases, the guidewire lumen 150 may be routed through a second lumen of the lumen member 130. In some examples, the multi lumen member may include a tri lumen extrusion. In that case, one or more filaments of the primary constrainment member 405 may be routed through a first lumen and a third lumen of the lumen member 130. For example, a first filament of the primary constrainment member 405 may be tied around the proximal portion 230 of the stent 170-*a* (e.g., proximal cuff portion) and routed through the first lumen of the lumen member 130, and a second filament of the primary constrainment member 405 may be tied around the distal portion 235 of the stent 170-*a* (e distal sock portion) and routed through the third lumen of the multi lumen member.

Figure 4B:
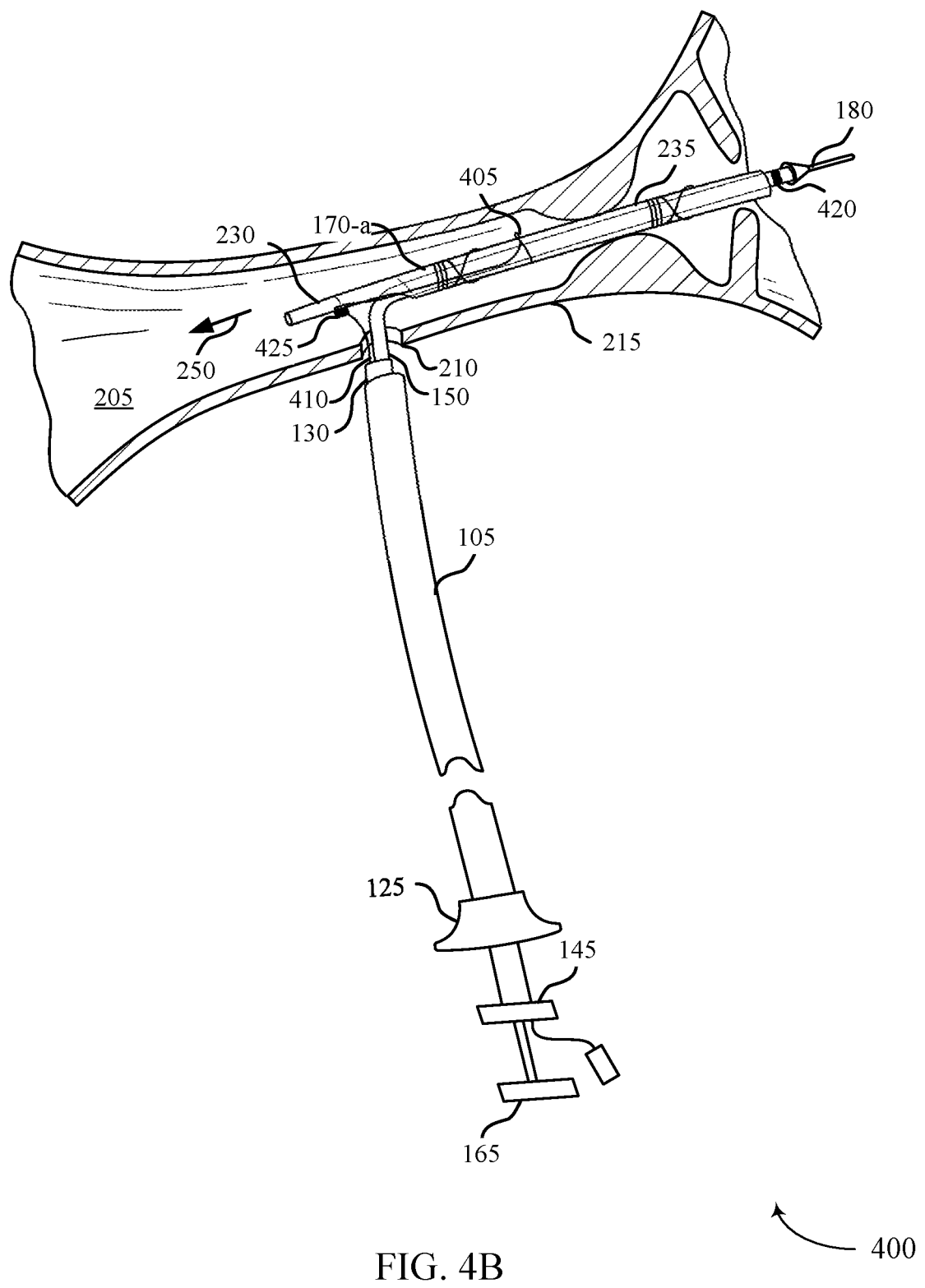
FIG. 4B illustrates a stent delivery system with the stent retracted towards the access hole in accordance with aspects of the present disclosure.

FIG. 4B illustrates a stem delivery system 400 with the stem 170-*a* retracted towards the access site 210 in accordance with aspects of the present disclosure. Once the outer sheath 105 is removed through the access site 210, the stent 170-*a* may be pulled toward the access site 210 in a proximal direction, as indicated by arrow 250. For example, the stent 170-*a* may be pulled towards the access site 210 until the proximal portion 230 of the stent 170-*a* at least partially covers the access site 210. The stent 170-*a* may be retracted towards the access site 210 by pulling the guidewire lumen 150 in a proximal direction. For example, the stent 170-*a* may be pulled towards the access site 210 by pulling the huh 165 of the guidewire lumen 150. The proximal portion 230 of the stent 170-*a* may be tied such that the primary constrainment member 1250 prevents the proximal portion 230 from catching on the wall 215 of the body lumen as the stent 170-*a* is retracted.

In some cases, a proximal portion 230 of the stent 170-*a* may be deployed prior to retracting the stent 170-*a* towards the access site 210. For example, one or more tethers 410 may be coupled with the primary constrainment member 405. For example, a first tether 410 may be coupled to a proximal portion 230 of the stent 170-*a*. In that case, the proximal portion 230 of the stent 170-*a* may be deployed by pulling the first tether 410 in a proximal direction. The stent 170-*a* may then be retracted towards the access site 210 by pulling the guidewire lumen 150 in the proximal direction. Furthermore, the stent 170-*a* may be repositioned within the body lumen 205 to at least partially cover the access site 210.

Figure 4C:
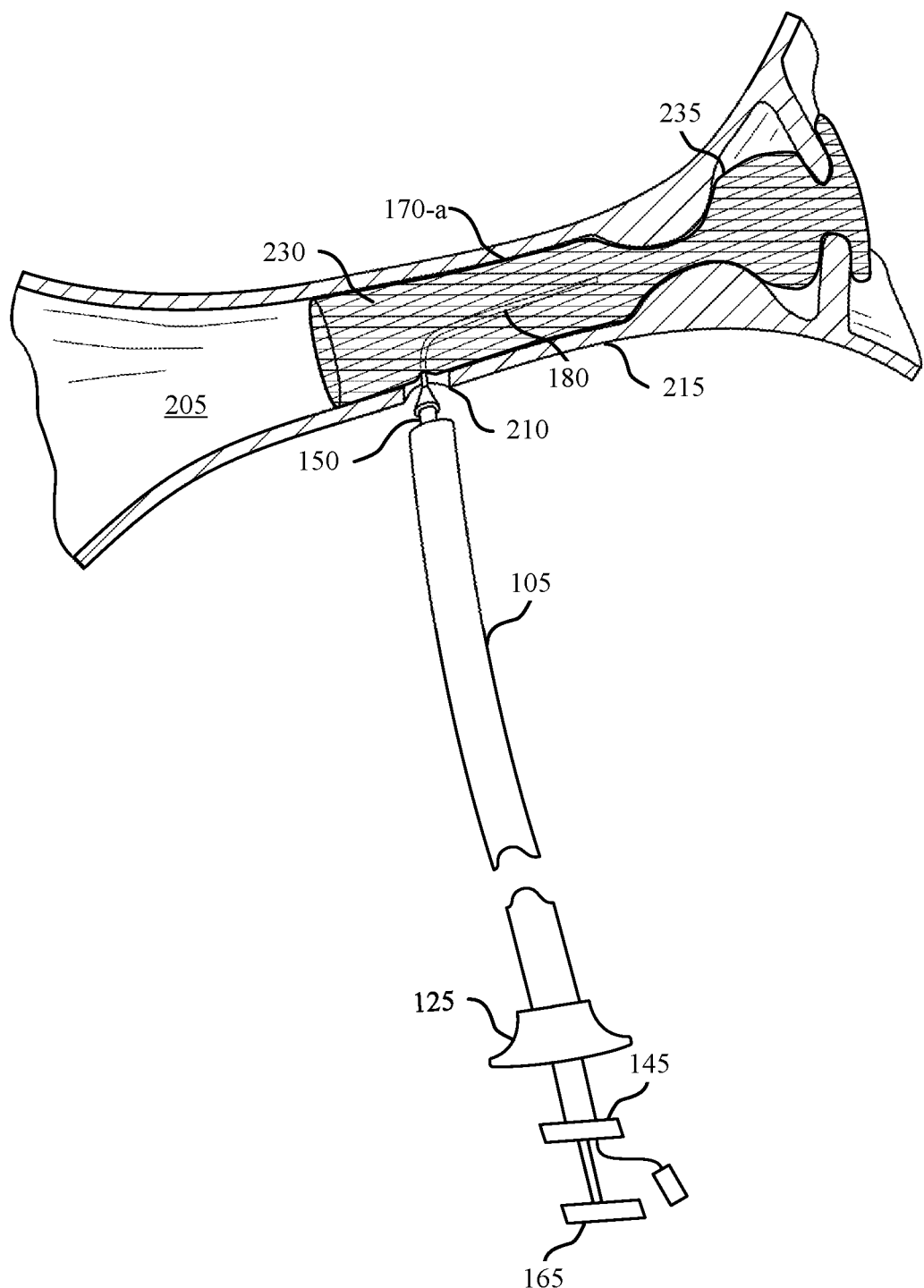
FIG. 4C illustrates a stent delivery system with the stent fully deployed in accordance with aspects of the present disclosure.

FIG. 4C illustrates a stent delivery system 400 with the stent 170-*a* fully deployed in accordance with aspects of the present disclosure. To deploy the stent 170-*a* within the body lumen 205, the primary constrainment member may be released. The stent 170-*a* may be deployed by pulling the primary constrainment member in a proximal direction. For example, the stent 170-*a* may be deployed by pulling the one or more tethers coupled with the primary constrainment member in the proximal direction. In that case, the one or more knots may unravel to deploy the stent 170-*a*. For example, the first tether may be coupled to a proximal portion 230 of the stent 170-*a* and be configured to deploy the proximal portion 230 of the stent 170-*a*. In other examples, a second tether may be coupled with the distal portion 235 of the stent 170-*a*. In that case, the distal portion 235 of the stent 170-*a* may be deployed by pulling the second tether in a proximal direction.

In some cases, the pulling force of the primary constrainment member may be directed along a longitudinal axis of the stent 170-*a* such that the one or more loops anchored to the guidewire lumen 150 may unfasten. In the case of a self-expanding stent, the stent 170-*a* expands to contact the inner surface of the body lumen 205. Once the stent 170-*a* expands within the body lumen 205, the guidewire lumen 150, the guidewire 180, the primary constrainment member, and one or more tethers are withdrawn through the access site 210.

Figure 5A:
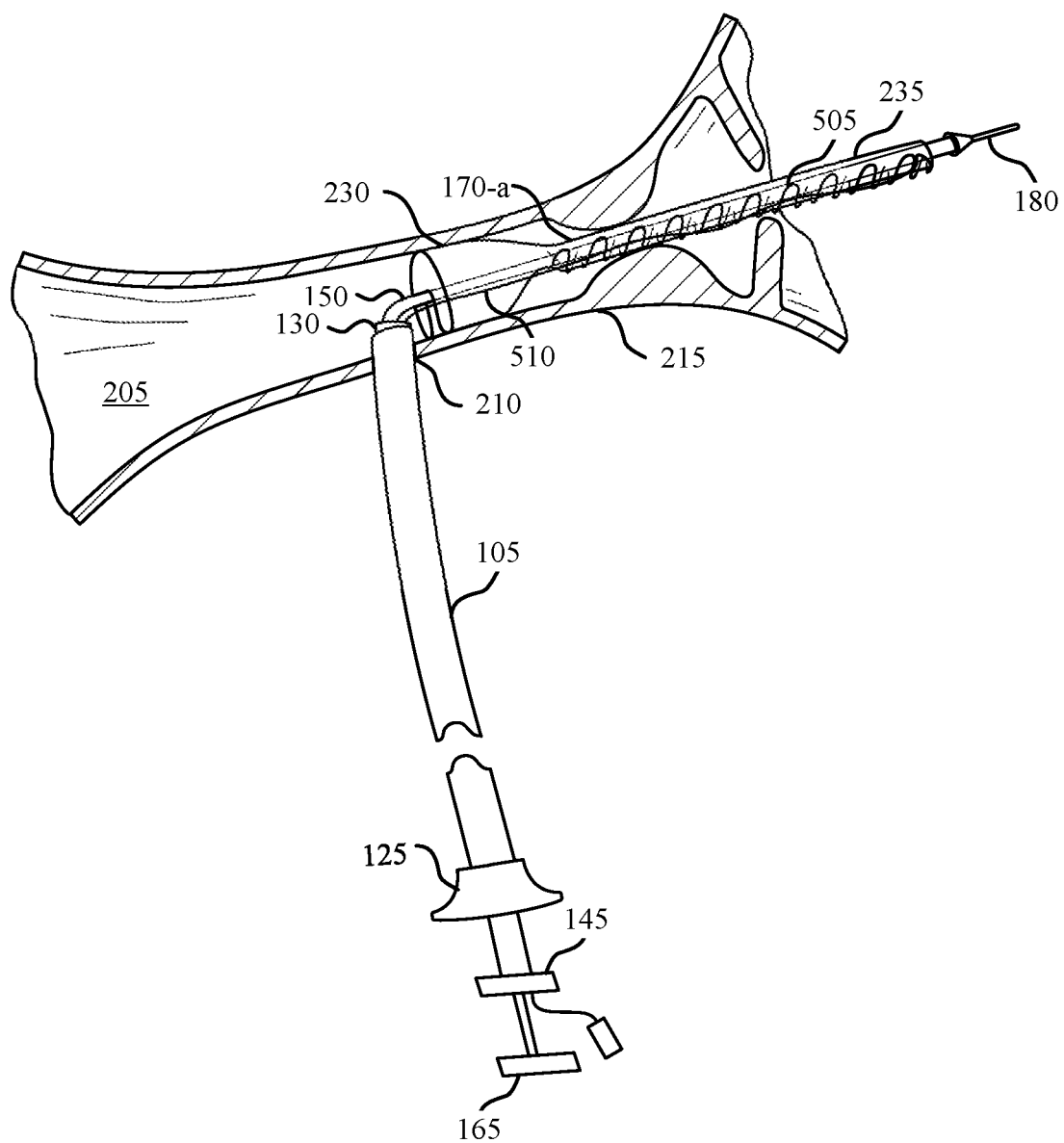
FIG. 5A illustrates a stent delivery system with a wire frame around a stent in accordance with aspects of the present disclosure.

FIG. 5A illustrates a stent delivery system 500 with a wire frame around a stent 170-*a* in accordance with aspects of the present disclosure. As the outer sheath 105 is removed from the access site 210, the stent 170-*a* may be exposed within the body lumen 205. The stent 170-*a* may be disposed around the guidewire lumen 150 in the partial side-saddle configuration.

The stent 170-*a* may be releasably coupled with the guidewire lumen 150 by a primary constrainment member 505. In some examples, the primary constrainment member 505 may be an example of a wire frame around the stent 170-*a*. The primary constrainment member 505 may wrap at least partially around the stent 170-*a*. For example, the primary constrainment member 505 may be formed by heat setting a Nitinol wire around a mandrel to form a series of S-shape rings or C-shape rings. The Nitinol wire may be coated with a lubricous material such as PTF, parylene-N or Silicone to reduce stent deployment force.

In some cases, the width of a single S-shape or C-shape ring may be within a range of 0.0050 to 0.0400 inches. In some examples, the width of a single S-shape or C-shape ring may be within a range of 0.0100 to 0.0175 inches. The outer diameter of the primary constrainment member 505 may be within a range of 0.004 to 0.015 inches. In some examples, the outer diameter of the primary constrainment member 505 within a range of 0.007 to 0.010 inches.

The primary constrainment member 505 may extend from the distal portion 235 of the stent 170-*a* to the proximal portion 230 of the stent 170-*a* and parallel to a longitudinal axis of the guidewire lumen 150. For example, the primary constrainment member 505 may be formed by wrapping a S-shape or C-shape ring around a distal portion 235 of the stent 170-*a*. Consecutive S-shape or C-shape rings may be wrapped from the distal portion 235 to the proximal portion 230 of the stent 170-*a*.

A tether 510 may be attached to the primary constrainment member 505 and extend through the access site 210. In some cases, the tether 510 may be an extension of the primary constrainment member 505 (e.g., comprising the same material as the primary constrainment member 505 and seamlessly connected to primary constrainment member 505). For example, the tether 510 may be a longitudinal wire comprising Nitinol. In other examples, the tether 510 may be attached to the primary constrainment member 505. For example, the tether 510 may be attached to a distal end of the primary constrainment member 505 and extend from the distal end of the primary constrainment member 505 in the proximal direction and into the outer sheath 105.

In some cases, the primary constrainment member 505 may be routed in a proximal direction into a first lumen of the lumen member 130. In some cases, the guidewire lumen 150 may be routed through a second lumen of the lumen member 130. In some examples, the lumen member 130 may include a slotted first lumen. In that case, the first lumen may be open to an outside surface of the lumen member 130 to reduce friction as the tether 510 is retracted to deploy the stent 170-a.

Figure 5B:
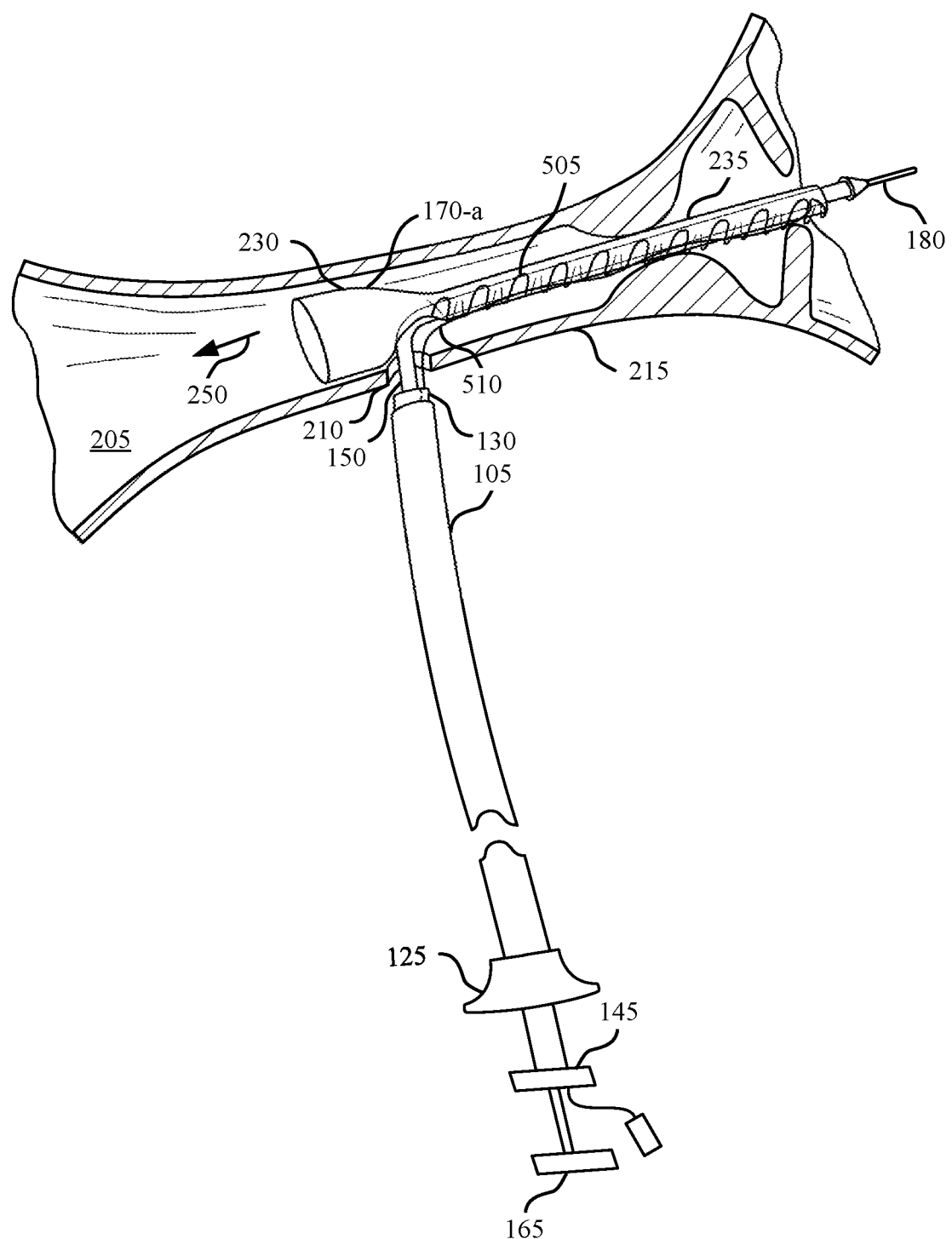
FIG. 5B illustrates a stent delivery system with the stent retracted towards the access site in accordance with aspects of the present disclosure.

FIG. 5B illustrates a stent delivery system 500 with the stent 170-a retracted towards the access site 210 in accordance with aspects of the present disclosure. Once the outer sheath 105 is removed through the access site 210, the stent 170-a may be pulled toward the access site 210 in a proximal direction, as indicated by arrow 250. For example, the stent 170-a may be pulled towards the access site 210 until the proximal portion 230 of the stent 170-a at least partially covers the access site 210. The stent 170-a may be retracted towards the access site 210 by pulling the guidewire lumen 150 in a proximal direction. For example, the stent 170-a may be retracted towards the access site 210 by pulling the huh 165 of the guidewire lumen 150. Furthermore, the stent 170-a may be repositioned within the body lumen 205 to at least partially cover the access site 210.

Figure 5C:
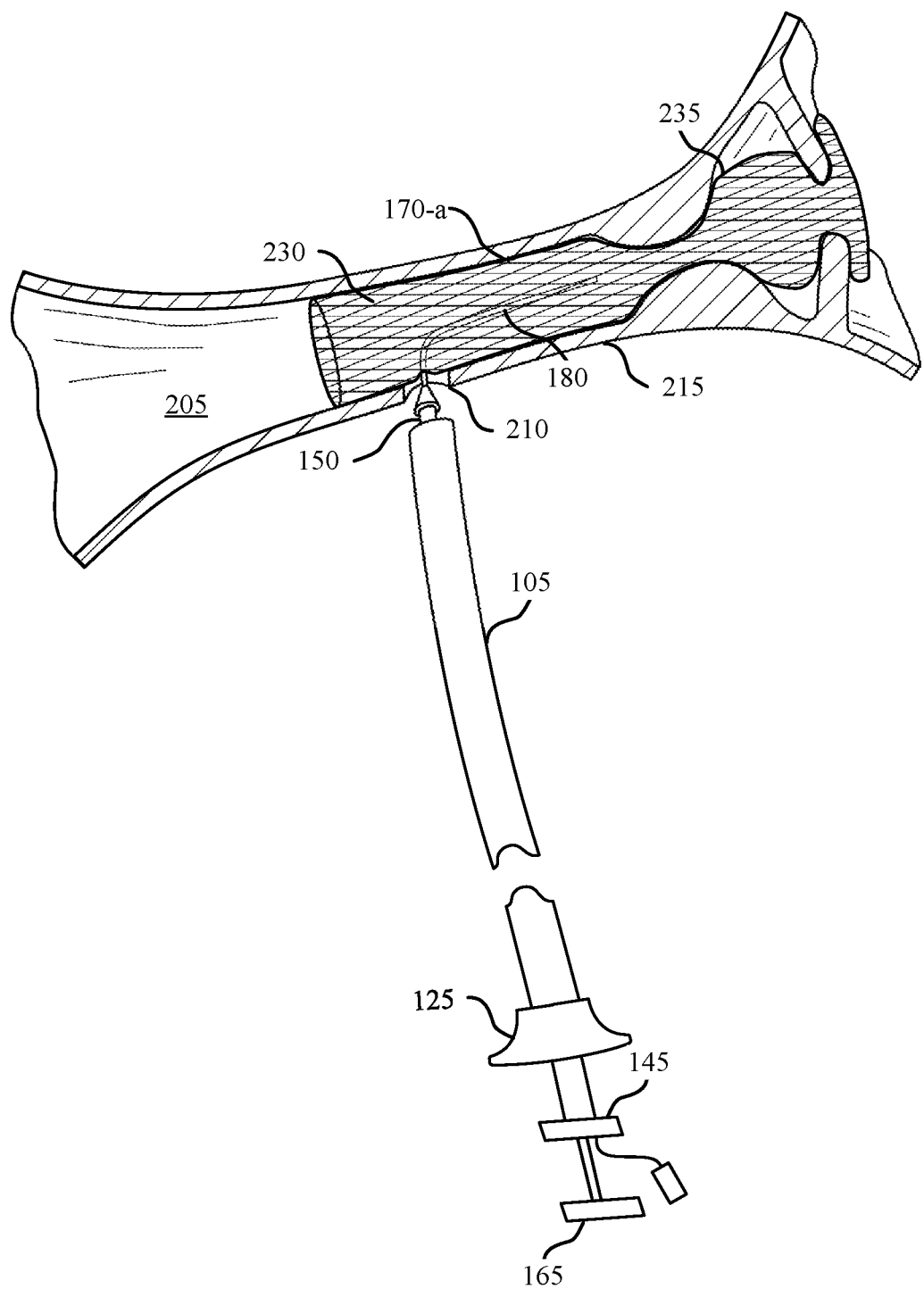
FIG. 5C illustrates a stent delivery system with the stent fully deployed in accordance with aspects of the present disclosure.

FIG. 5C illustrates a stent delivery system 500 with the stent 170-a fully deployed in accordance with aspects of the present disclosure. To deploy the stent 170-a within the body lumen 205, the primary constrainment member may be released. The stent 170-a may be deployed by pulling the primary constrainment member in a proximal direction. For example, the stent 170-a may be deployed by pulling the tether coupled with the primary constrainment member. The tether attached to the distal end of the primary constrainment member may be configured to deploy the stent 170-a from a distal direction to a proximal direction. For example, this deployment mechanism may allow the clinician to stop the distal stent deployment and reposition the stent 170-a relative to the access site 210.

In some cases, the primary constrainment member may be configured to deploy the stent 170-a from a proximal to a distal direction. In that case, a proximal portion of the primary constrainment member may extend into the outer sheath 105. That is, the proximal end of the primary constrainment member may unwind after the outer sheath 105 is retracted in a proximal direction. In other examples, the tether may be attached and extend from a proximal loop of the primary constrainment member. In that case, when the tether is pulled in a proximal direction, a proximal portion of the primary constrainment member unwinds to release the stent 170-a from a proximal direction to a distal direction.

In the case of a self-expanding stent, the stent 170-a expands to contact the inner surface of the body lumen 205. Once the stein 170-a expands within the body lumen 205, the guidewire lumen 150, the guidewire 180, the primary constrainment member, and the tether are withdrawn through the access site 210.

Figure 6A:
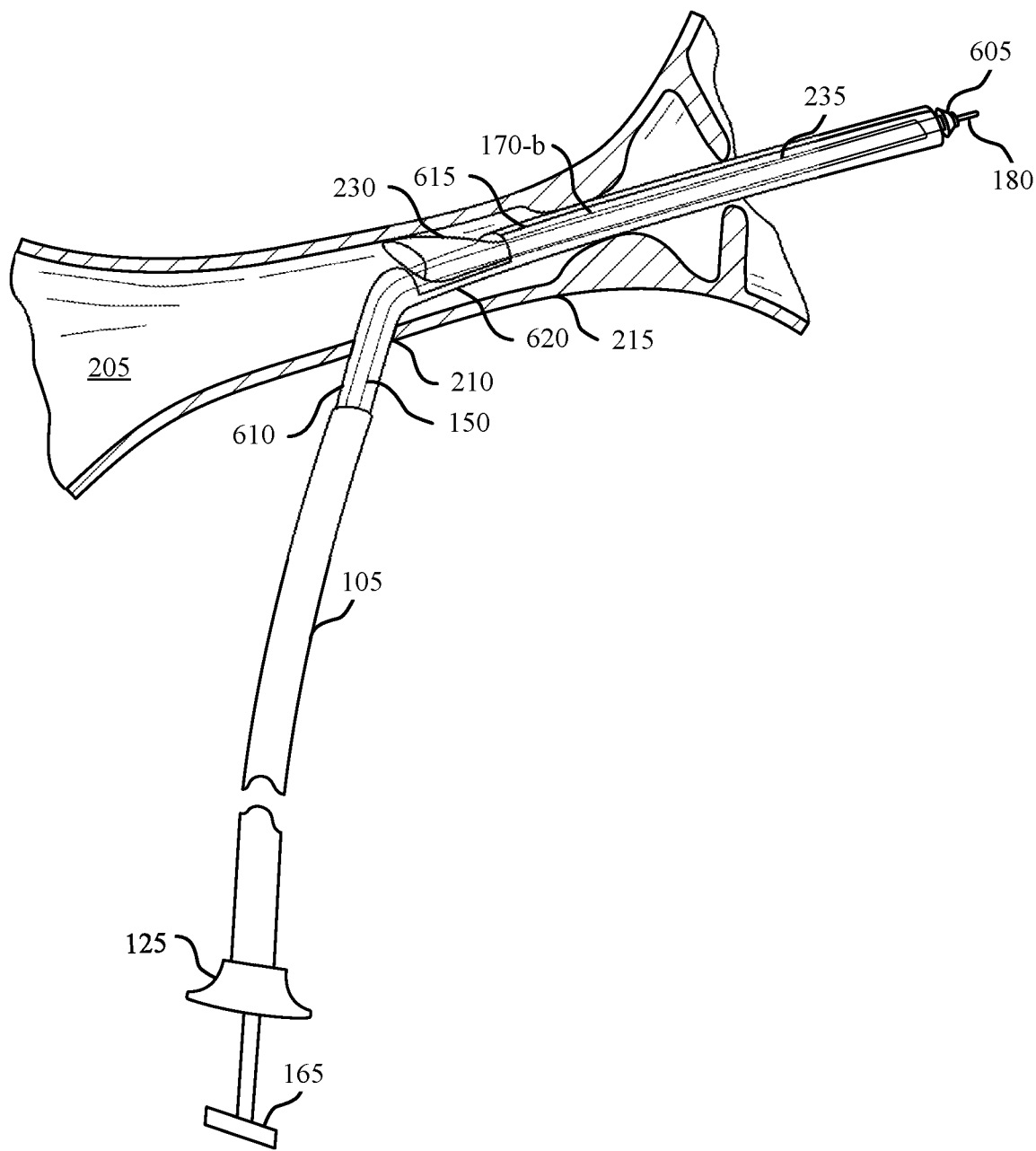
FIG. 6A illustrates a stent delivery system with a splittable sheath in accordance with aspects of the present disclosure.

FIG. 6A illustrates a stent delivery system 600 with a splittable sheath in accordance with aspects of the present disclosure. As the outer sheath 105 is removed from the access site 210, the stent 170-a may be enclosed within the body lumen 205. In some cases, the stent 170-b may be partially disposed around the guidewire lumen 150 such that the guidewire lumen 150 is outside the stent 170-b along the proximal portion 230 and the distal portion 235 of the stent 170-b, which may be referred to as the side-saddle configuration. That is, in the side-saddle configuration, the guidewire lumen 150 does not extend through the lumen of the stent 170-b. In some cases, the guidewire lumen 150 may include a distal tip 605.

The stent 170-b may be releasably coupled with the guidewire lumen 150 by a primary constrainment member. In some examples, the primary constrainment member may be an example of a splittable sheath 610. The splittable sheath 610 may refer to a partially-tubular portion between an inner surface of the outer sheath 105 and an outer surface of the stent 170-b. That is, the splittable sheath 610 may not be completely tubular itself. In some cases, the splittable sheath 610 may be sufficiently stiff to resist the radial expansion force of the stent 170-b within the splittable sheath 610. The splittable sheath 610 may be manufactured from a variety of materials such as thermoplastic elastomers. Exemplary thermoplastic elastomer materials include, but are not limited to, polyether block amide (PEBA). For example, the splittable sheath 610 may include a copolymer material with thermoplastic and elastomeric properties.

The splittable sheath 610 may include a longitudinal element 615. The longitudinal element 615 may be oriented along the longitudinal axis of the tubular body of the splittable sheath 610. The longitudinal element 615 may adhere to the splittable sheath 610 to form the tubular body of the splittable sheath 610. The longitudinal element 615 may be manufactured from a variety of materials such as polymers. Exemplary polymeric-based materials include, but are not limited to, high-density polyethylene (HDPE). For example, the longitudinal element 615 may consist of a material characterized by a chain of unbranched, linear polyethylene polymers. In that case, the splittable sheath 610 may be manufactured from a variety of materials such as thermoplastic elastomers. Exemplary thermoplastic elastomer materials include, but are not limited to, polyether block amide (PEBA). For example, the splittable sheath 610 may include a copolymer material with thermoplastic and elastomeric properties. In some examples, the longitudinal element 615 may be perforation along the longitudinal axis of the splittable sheath 610. In other examples, the longitudinal element 615 may be a string or wire.

In order to prevent premature splitting of the splittable sheath 610, the distal end of the splittable sheath 610 may include a braided reinforcement thermally fused around the splittable sheath 610. For example, the braided reinforcement may be coupled a portion of the splittable sheath 610, and the braided reinforcement may be comprised of a partially tubular body with a channel that aligns with the longitudinal element 615. The braided reinforcement may be made from a braided frame structure. For example, the braided reinforcement may be made from a braided tubing that has a channel cut along its longitudinal direction. In some examples, the braided reinforcement may be made from a plurality of wires joined together in a cross-hatch configuration.

In some cases, the proximal portion 230 of the stent 170-b may be deployed prior to retraction of the distal tip 605. In some examples, the outer sheath 105 may be located on the proximal end of the stent delivery system 600. The splittable sheath 610 may include an open pocket 620 (e.g., slit) at a proximal end of the split table sheath 610 where the stent 170-b may partially deploy. For example, the open pocket 620 may be configured to house the stent 170-b when the outer sheath 105 is located on the proximal end of the stent delivery system 600 and deploy the stent 170-a when the outer sheath 105 pulled from the proximal end of the stent delivery system 600 and through the access site 210.

Figure 6B:
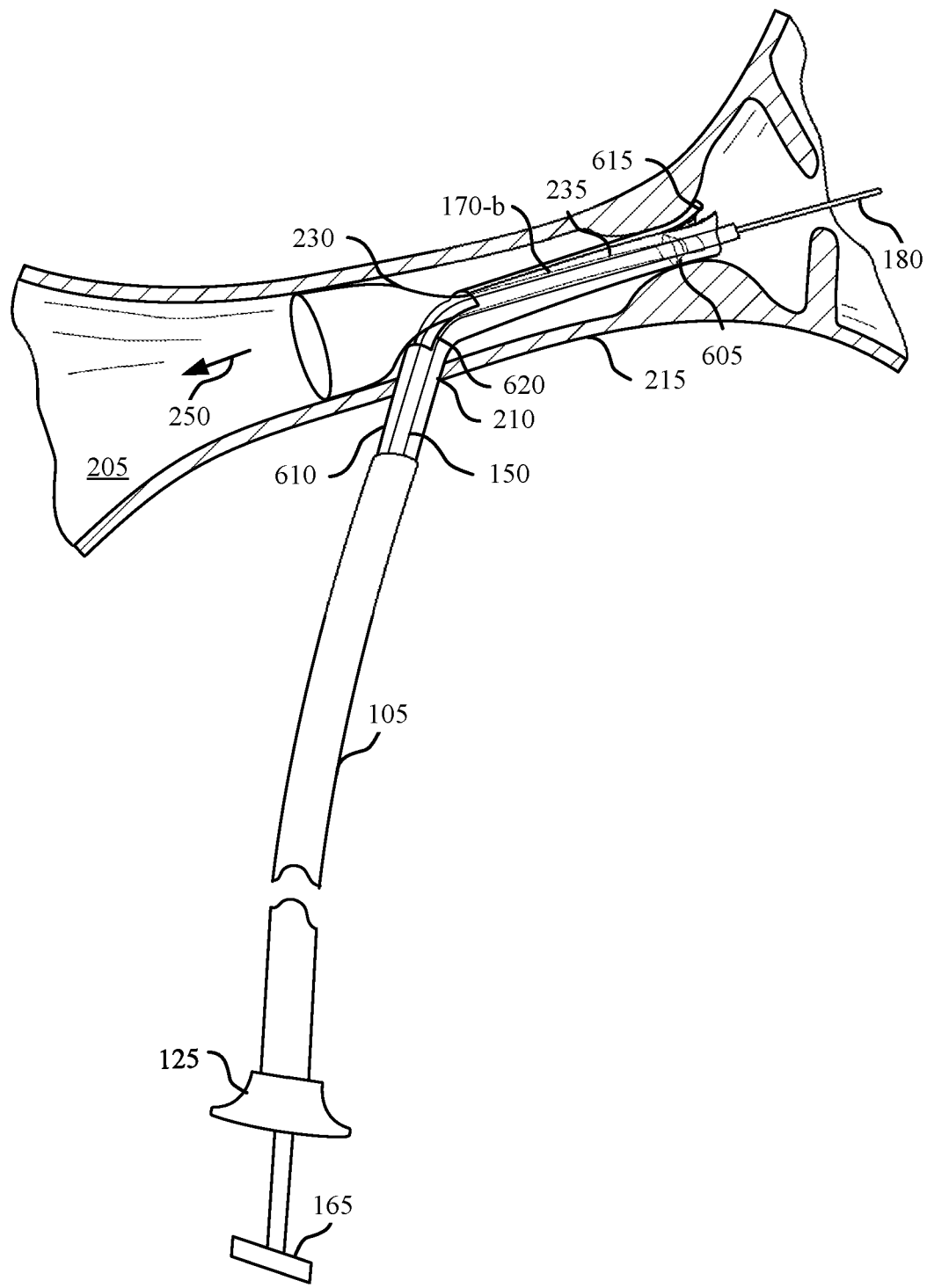
FIG. 6B illustrates a stent delivery system with the stent retracted towards the access site in accordance with aspects of the present disclosure.

FIG. 6B illustrates a stent delivery system 600 with the stent 170-*b* retracted towards the access site 210 in accordance with aspects of the present disclosure. Once the outer sheath 105 is removed through the access site 210, the stent 170-*b* may be pulled toward the access site 210 in a proximal direction, as indicated by arrow 250. For example, the stent 170-*b* may be pulled toward the access site 210 until the proximal portion 230 of the stent 170-*b* at least partially covers the access site 210. The stent 170-*b* may be retracted towards the access site 210 by pulling the splittable sheath 610 in a proximal direction, as indicated by arrow 250. Furthermore, the stent 170-*a* may be repositioned within the body lumen 205 to at least partially cover the access site 210.

To fully deploy the stent 170-*b*, the distal tip 605 of the guidewire lumen 150 may be configured to facilitate tearing of the splittable sheath 610 along the longitudinal element 615. For example, an outer diameter of the distal tip 605 may be greater than an inner diameter of the splittable sheath 610. As such, as the distal tip 605 is pulled proximally through the splittable sheath 610, the distal tip 605 may stretch the split/able sheath 610 and cause the splittable sheath 610 to tear along the longitudinal element 615. As the splittable sheath 610 tears, the stent 170-*b* may begin to deploy from the splittable sheath 610 and into the body lumen 205. Because the stent 170-*b* is located between the inside surface of the splittable sheath 610 and the guidewire lumen 150 in a side-saddle configuration, the stent 170-*b* will be pushed from the distal end of the splittable sheath 610 as the distal tip 605 is withdrawn proximally.

When the outer sheath 105 is retracted in the proximal direction, the proximal portion 230 of the stent 170-*a* may deploy through the open pocket 620 of the splittable sheath 610. That is, the stent 170-*b* may cover at least a portion of the access site 210 in the body lumen 205. In order to provide support for the open pocket 620, the open pocket 620 of the splittable sheath 610 may be reinforced with one or more axial wires. For example, one or more axial wires may be positioned within the splittable sheath 610 and 180 degrees opposite the open pocket 620. The one or more axial wires may be made from any number of metallic materials including, but not limited to, nitinol or stainless steel.

Figure 6C:
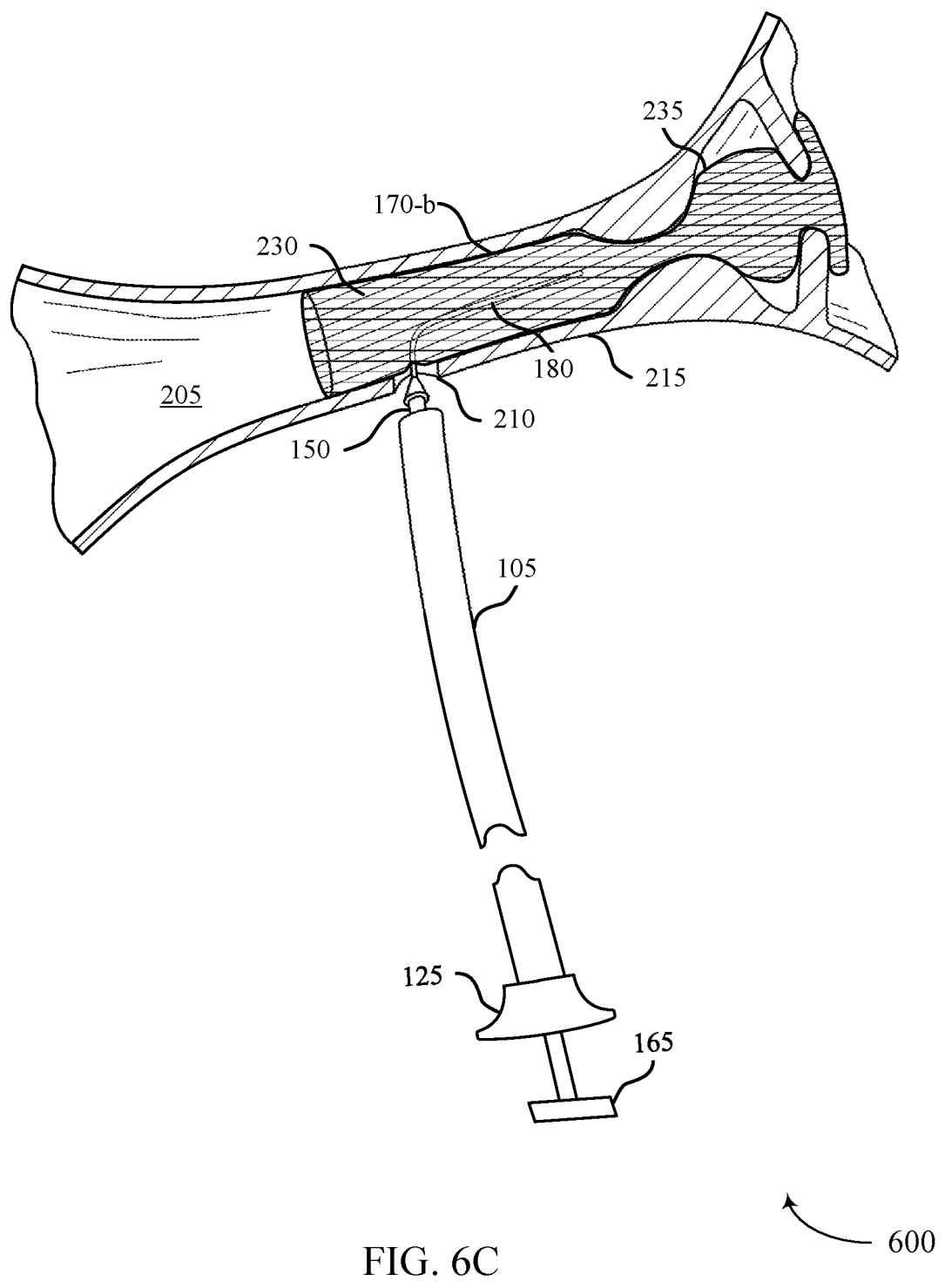
FIG. 6C illustrates a stent delivery system with the stent fully deployed in accordance with aspects of the present disclosure.

FIG. 6C illustrates a stent delivery system 600 with the stent 170-*b* fully deployed in accordance with aspects of the present disclosure. To deploy the stent 170-*b* within the body lumen 205, the primary constrainment member may release the stent 170-*b* from a constrained configuration. The stent 170-*b* may be deployed by withdrawing the distal tip of the guidewire lumen 150 in a proximal direction. In that case, the distal tip may tear the primary constrainment member along the longitudinal element, thereby deploying the stent 170-*b* within the body lumen 205. Once the stent 170-*b* expands within the body lumen 205, the guidewire lumen 150, the guidewire 180, and the primary constrainment member are withdrawn through the access site 210. In the case of a self-expanding stent, the stent 170-*b* expands to contact the inner surface of the body lumen 205.

Figure 7A:
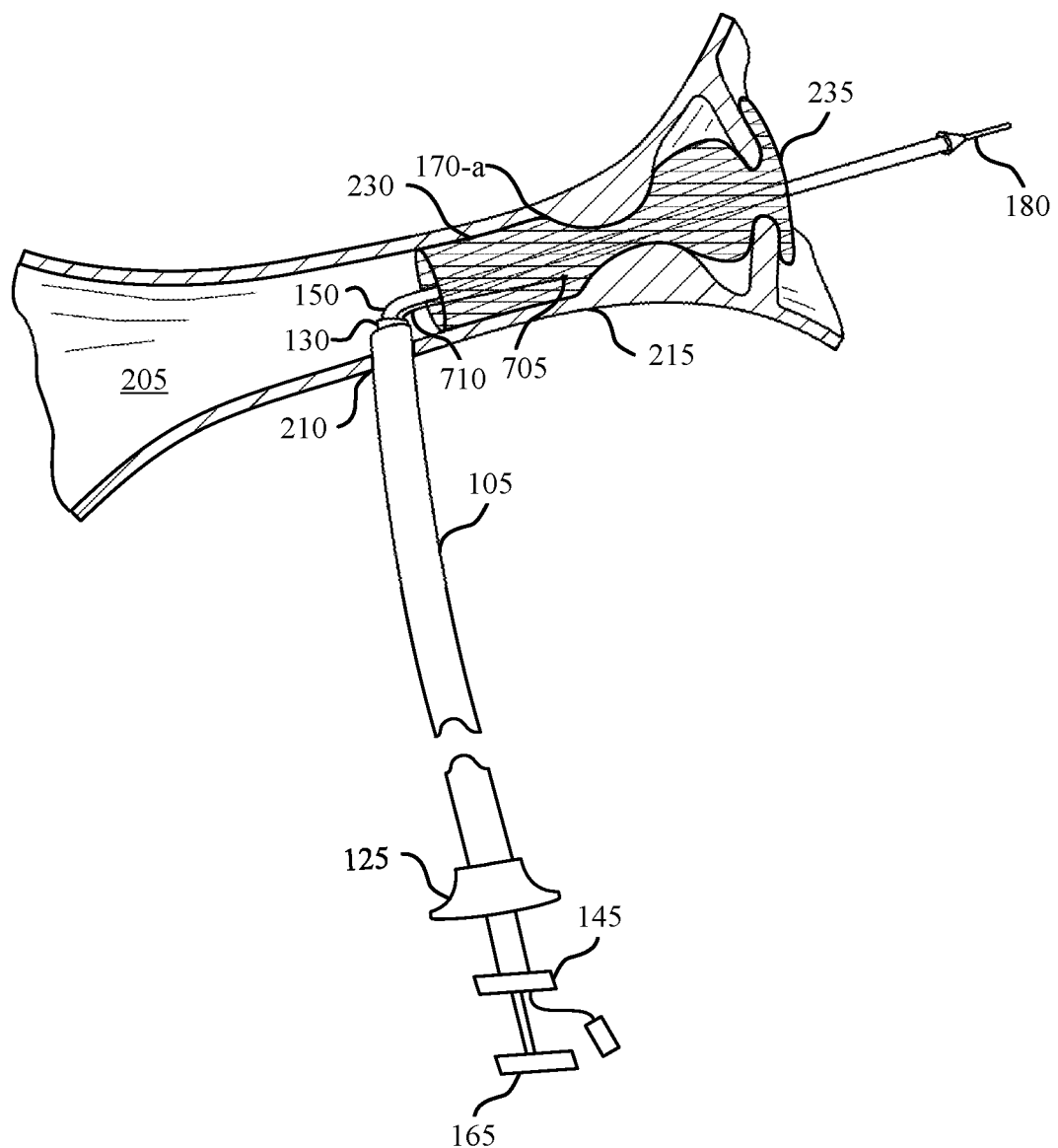
FIG. 7A illustrates a stent delivery system with a coupling ring in accordance with aspects of the present disclosure.

FIG. 7A illustrates a stent delivery system 700 with a coupling ring 705 in accordance with aspects of the present disclosure. As the outer sheath 105 is removed from the access site 210, the stent 170-*a* may be exposed within the body lumen 205. The stent 170-*a* may be disposed around the guidewire lumen 150 in the partial side-saddle configuration. In some cases, the stent 170-*a* may be disposed around the guidewire lumen 150 in concentric configuration. To deploy the stent 170-*a* within the body lumen 205, the outer sheath 105 may be removed. In the case of a self-expanding stent, the stent 170-*a* expands to contact the inner surface of the body lumen 205.

The stent delivery system 700 may include a coupling ring 705. The coupling ring 705 may be releasably coupled with the stent 170-*a*. In some cases, the coupling ring 705 may comprise an eyelet or ring that is attached to the stent 170-*a*. The coupling ring 705 may be circular or elliptical. In some examples, the coupling ring 705 may comprise a stainless-steel material which may be welded between wire filaments of the stent 170-*a*. For example, the coupling ring 705 may be attached to the struts or braided wire of the stent 170-*a*. In some examples, the shape of the coupling ring 705 may be a split-ring. In that case, the 'split-ring' may be attached to the coupling ring 705 welded to the stent 170-*a*. The split-ring may be configured such that the ends of the split-ring may separate and detached from the coupling ring 705. The coupling ring 705 may be attached to the stent 170-*a* at a distance of one quarter or one third of the length of the stent 170-*a* from the proximal end of the proximal portion 230.

The stent delivery system 700 may also include a tether 710. The tether 710 may be coupled with the coupling ring 705. In the case of the split-ring, the tether 710 may be laser welded to the split ring. In some examples, the tether 710 may be inserted through the eyelet of the coupling ring 705 and extend proximally through the outer sheath 105. In some cases, the tether 710 may be routed in a proximal direction into a first lumen of the lumen member 130. In some cases, the guidewire lumen 150 may be routed through a second lumen of the lumen member 130.

Figure 7B:
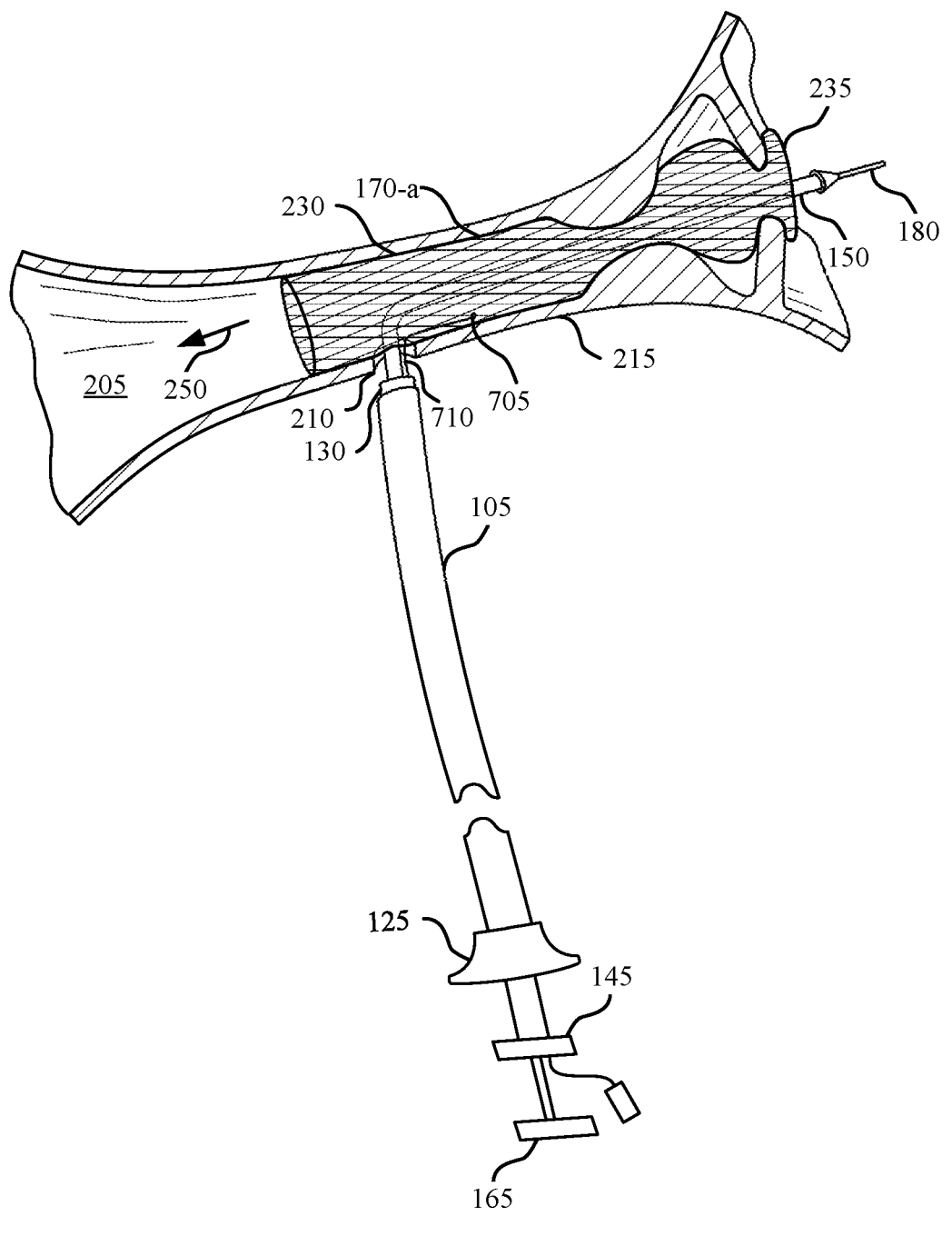
FIG. 7B illustrates a stent delivery system with the stent retracted towards the access site in accordance with aspects of the present disclosure.

FIG. 7B illustrates a stein delivery system 700 with the stent 170-*a* retracted towards the access site 210 in accordance with aspects of the present disclosure. Once the outer sheath 105 is removed through the access site 210, the guidewire lumen 150 may be removed through the access site 210, and the stent 170-*a* may be pulled toward the access site 210 in a proximal direction, as indicated by arrow 250. For example, the stent 170-*a* may be pulled toward the access site 210 until the proximal portion 230 of the stent 170-*a* at least partially covers the access site 210.

The stent 170-*a* may be retracted towards the access site 210 by pulling the tether 710 in a proximal direction. Once a predetermined force is exceeded, the tether 710 may detach from the coupling ring 705. In some examples, the tether 710 may exit the eyelet of the coupling ring 705 through which the tether 710 was inserted through. In other examples, the coupling ring 705 may separate and open to detach the tether 710 from the coupling ring 705. Furthermore, the stent 170-*a* may be repositioned within the body lumen 205 to at least partially cover the access site 210.

Figure 7C:
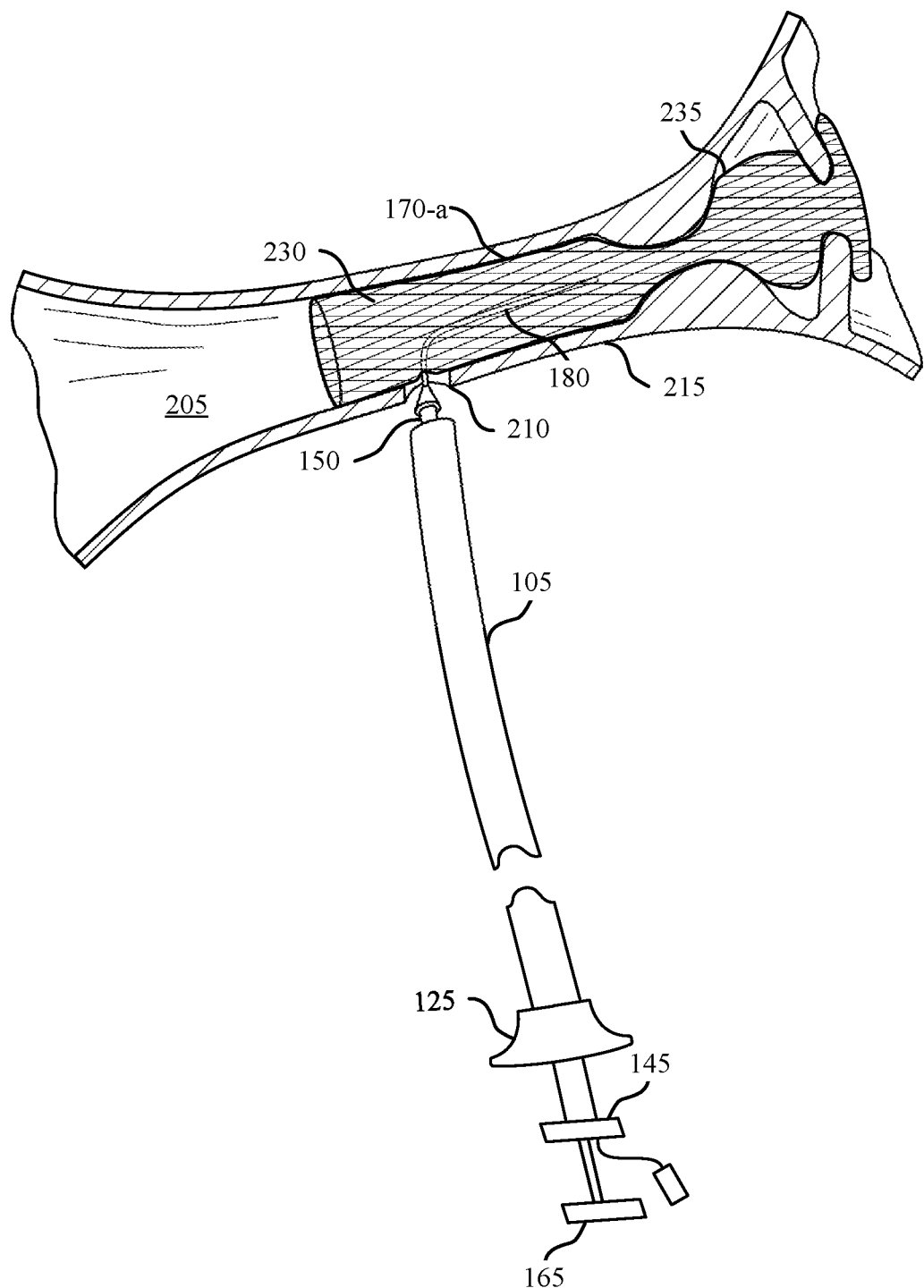
FIG. 7C illustrates a stent delivery system with the stent fully deployed in accordance with aspects of the present disclosure.

FIG. 7C illustrates a stent delivery system 700 with the stent 170-*a* fully deployed in accordance with aspects of the present disclosure. Once the stem 170-*a* expands within the body lumen 205, the guidewire lumen 150, the guidewire 180, the tether coupled with the primary constrainment member, and the tether coupled with the coupling ring are withdrawn through the access site 210.

Figure 8:
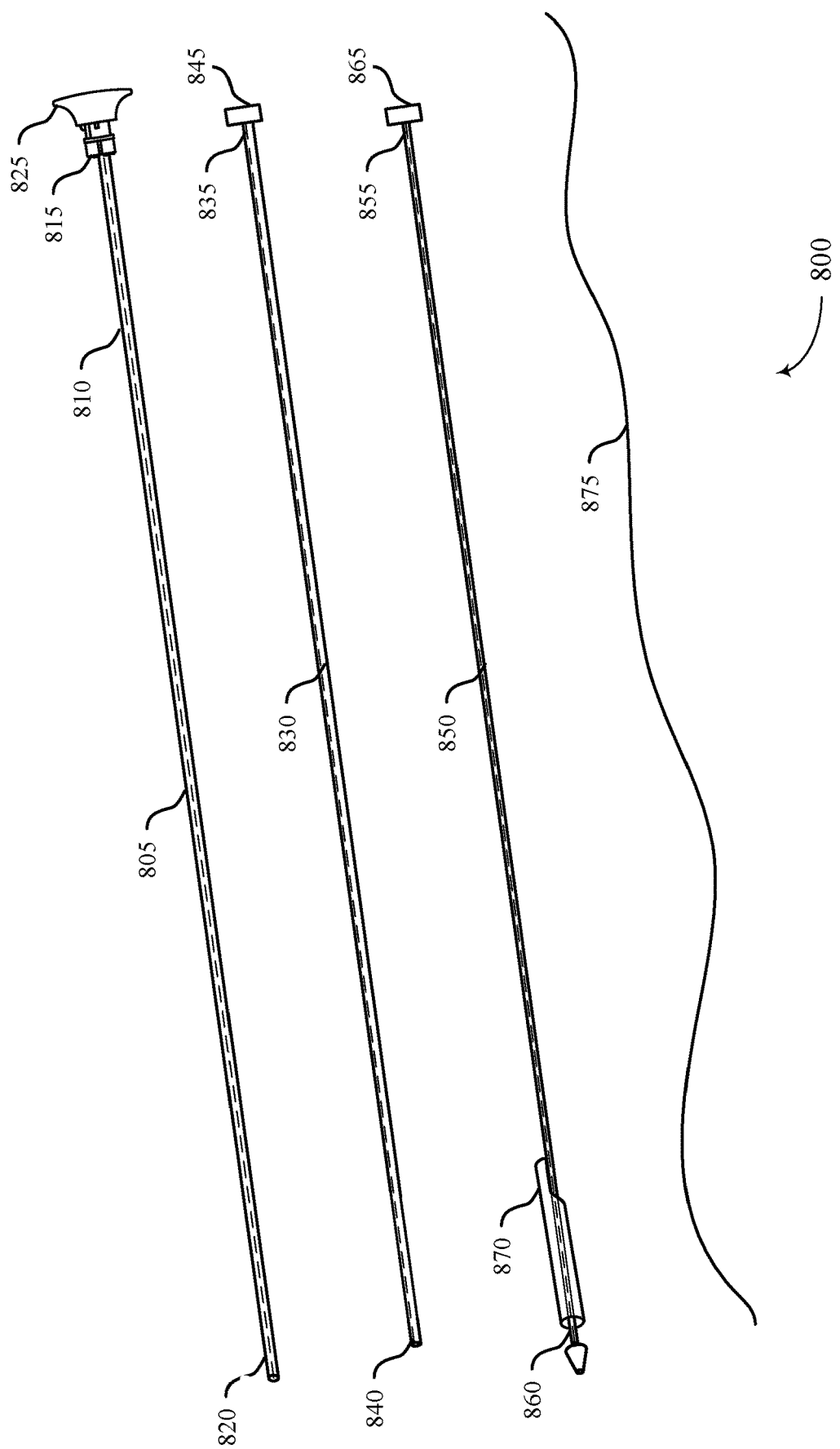
FIG. 8 illustrates an exploded view of a system for providing access to a body lumen with an inner pusher in accordance with aspects of the present disclosure.

FIG. 8 illustrates an exploded view of a system 800 for providing access to a body lumen with an inner pusher in accordance with aspects of the present disclosure. The system 800 generally includes an outer sheath 805, an inner pusher 830, a guidewire lumen 850, a stent 870, and a guidewire 875. The system 800 can be provided as individual components, selectively combined components, or all together as a kit of components. The outer sheath 805 may be inserted into a handle assembly (not pictured) until the outer sheath handle 825 abuts against the proximal end of the handle assembly. Once assembled, the outer sheath 805 extends through the handle assembly to the target body lumen.

During a luminal access procedure, the outer sheath 805 may access the target lumen by piercing a wall of the lumen, for example. In some examples, a sharpened stylet may be used in conjunction with the outer sheath 805 to facilitate piercing the luminal wall. For example, the sharpened stylet may be advanced through the outer sheath 805 until it protrudes from the outer sheath 805 to pierce tissue. Once the outer sheath 805 has accessed the lumen, the guidewire 875 may be advanced through the outer sheath 805 and into the lumen. After correct placement of the guidewire 875 inside the body lumen, the guidewire lumen 850 may be advanced over the guidewire 875 and into the body lumen. The guidewire lumen 850 may generally be a tubular structure that is sized to deploy the stent 870 within the body lumen. As such, the guidewire lumen 850 and stent 870 may be advanced over the guidewire 875 and into the body lumen. The guidewire lumen 850 may be retracted to position the stent 870 to cover the access site of the body lumen.

The system 800 may be used to access and provide treatment to one or more body lumens within the gastrointestinal system or pancreaticobiliary system, for example. It may be appreciated that the system 800 may also be used to provide access or treatment to other organs or luminal systems within the body such as the arterial system, the bronchial system, the urinary system, or any other luminal system were maneuverability and accuracy is desirable.

The outer sheath 805 of the system 800 has an elongate tubular body and an internal lumen 810 extending from its proximal end 815 to the distal end 820. In general, the outer sheath 805 is configured to access a body lumen (e.g., by piercing a luminal wall) and to provide a conduit through which one or more devices (e.g., a guidewire 875) may pass to facilitate subsequent treatment of the body lumen or associate organs. As described with reference to several embodiments, the outer sheath 805 may include features that facilitate the direction-controlled delivery of a guidewire 875 within the body lumen for subsequent delivery of a stent 870, a biopsy device, a medicinal delivery element, or any number of other treatment or diagnostic devices.

The inner pusher 830 is generally an elongate, tubular member with proximal end 835 and distal end 840 and is dimensioned to be advanced through the internal lumen 810 of the outer sheath 805. The inner pusher 830 may also include a middle handle 845 coupled with the proximal end 835 of the inner pusher 830 to facilitate longitudinal manipulation of the inner pusher 830 with respect to the outer sheath 805. In certain embodiments, the inner pusher 830 may abut a proximal portion of the stent 870 when the proximal portion of the stent 870 is constrained within the outer sheath 805. As described below, the inner pusher 830 is configured to advance through the outer sheath 805 and deploy the proximal portion of the stent 870 from the outer sheath 805.

The guidewire lumen 850 is generally an elongate, tubular member with proximal end 855 and distal end 860 and is dimensioned to slidably advance through the internal lumen of the internal pusher 830 and over the guidewire 875. The guidewire lumen 850 may also include a proximal handle 865 coupled with the proximal end 855 of the guidewire lumen 850 to facilitate longitudinal or rotational manipulation of the guidewire lumen 850 with respect to the outer sheath 805. In certain embodiments, the distal end 860 of the guidewire lumen 850 includes a tip or bulged portion. As described below, the stent 870 may be coupled to the guidewire lumen 850. For example, the stent 870 may be in a side-saddle configuration, where the guide wire lumen 850 does not extend through the lumen of the stent 870. In some examples, the stent 870 may be concentric with the guidewire lumen 850. This configuration may be referred to as concentric, where the guidewire lumen 850 may extend through the lumen of the stent 870. The stent 870 may be coupled to the guidewire lumen 850 in a combination of the complete side-saddle, partial side-saddle, or concentric configurations.

The guidewire 875 is generally a flexible elongate member configured to slidably advance through the internal lumen 810 of the outer sheath 805. The guidewire 875 may be uniform in size and stiffness along its entire length, or alternatively, may include sections of differing stiffness.

Figure 9A:
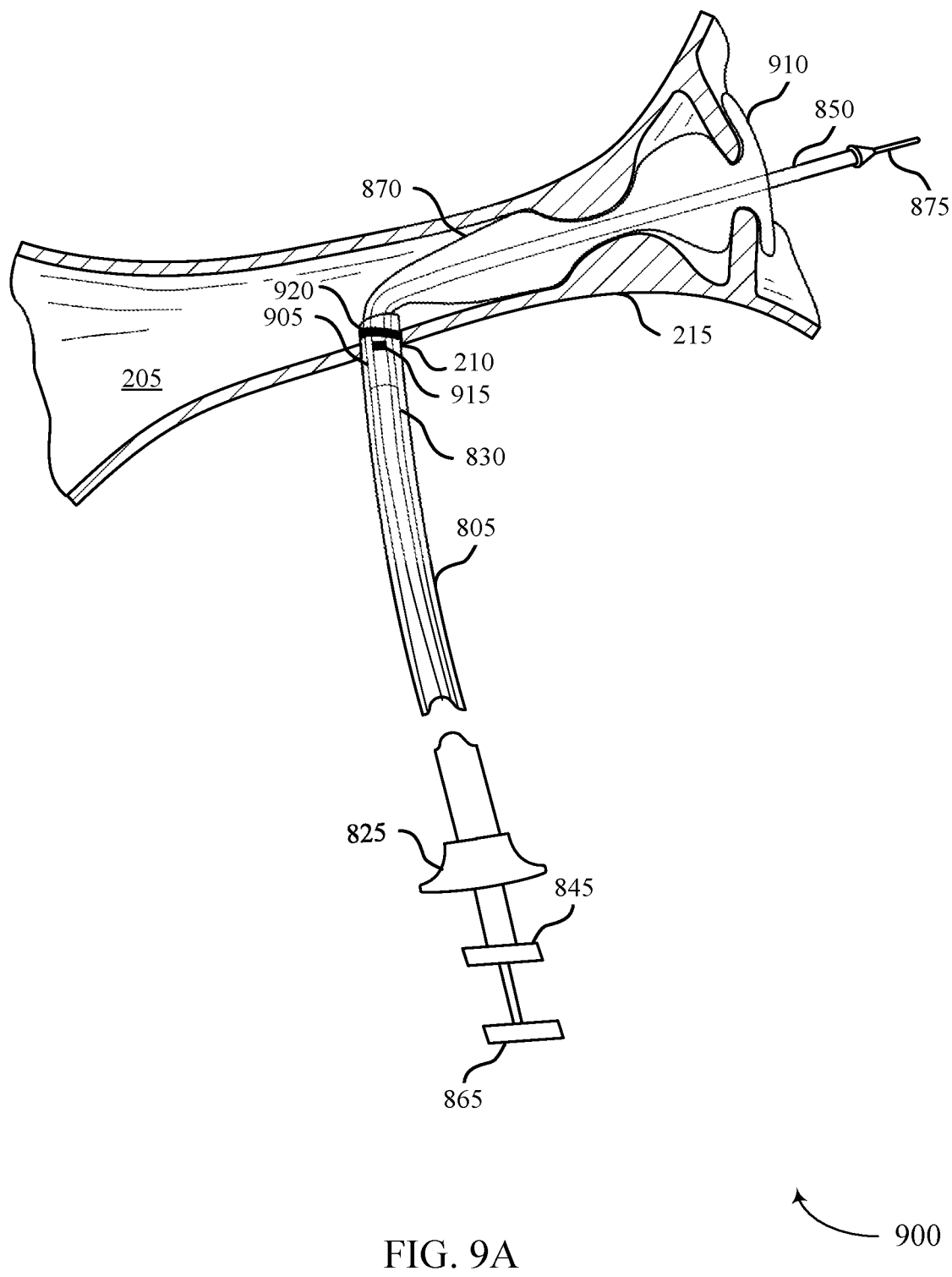
FIG. 9A illustrates a stent delivery system with the outer sheath removed in accordance with aspects of the present disclosure.

FIG. 9A illustrates a stent delivery system 900 with the outer sheath removed in accordance with aspects of the present disclosure. As the outer sheath 805 is withdrawn proximally through the access site 210, the stent 870 may be exposed within the body lumen 205. For example, as the outer sheath 805 is retracted towards the access site 210, the distal portion 910 of the stent 870 may be deployed. The distal portion 910 of the stent 870 may then be in a fixed position against a stricture within the body lumen 205. In some examples, the stent 870 may be fully disposed around the guidewire lumen 850. In that case, the guidewire lumen 850 may be inside the stent 870 along the distal portion 910 of the stent 870 and outside the stent 870 along the proximal portion 905.

In some cases, the proximal portion 905 of the stent 870 may remain inside the outer sheath 805. For example, as the outer sheath 805 is retracted towards the access site 210, the proximal portion 905 of the stent 870 may remain within an inside surface of the outer sheath 805. The outer sheath 805 may be retracted until a distal end of the outer sheath 805 aligns (or approximately aligns) with an inside surface of the access site 210.

The stent delivery system may include an inner pusher 830. The inner pusher 830 may extend through an inner surface the outer sheath 805. In some cases, the inner pusher may be slidably disposed on the guidewire lumen 850. Prior to deployment of the proximal portion 905 of the stent 870, the proximal portion 905 of the stent 870 may abut a proximal end of the inner pusher 830 within the outer sheath 805.

The guidewire lumen 850 may include a stent anchor 915. The stent anchor 915 may be located 1 to 2 cm distal to a location where the stent 870 is outside the guidewire lumen 850 (e.g., 1 to 2 cm distal to where the proximal portion 905 begins). The stent anchor 915 may be configured to allow the clinician to reconstrain the stent 870 (i.e., advance the outer sheath 805 in a distal direction to reconstrain the distal portion 910 of the stent 870) prior to repositioning.

In some examples, the guidewire lumen 850 may include a distal tip. The distal tip may taper at a proximal portion and a distal portion of the distal tip. In some cases, the distal tip may be configured to facilitate retraction of the guidewire lumen 850 through the portion of stent 870 that may be concentric with the guidewire lumen 850 without displacing the stent 870 post-deployment.

The outer sheath 805 may include a distal marker 920. For example, the distal marker 920 may be positioned around the distal end of the outer sheath 805. For example, the outer sheath 805 may be retracted until the distal marker 920 is proximal to the stent anchor 915. As described below in further detail, once the outer sheath 805 is retracted past the stent anchor 915, the inner pusher 830 may be advanced to push the proximal portion 905 of the stent 870 into the body lumen 205. However, once the outer sheath 805 is retracted past the stent anchor 915, the outer sheath 805 may not be advanced in a distal direction to reconstrain the distal portion 910 of the stent 870.

In some cases, the outer sheath 805 may include an inner jacket of etched PTFE liner with a wall thickness in a range of 0.0010 to 0.0020 inches and an outer jacket of polyether block amide (Pebax) material with a wall thickness in a range of 0.0040 to 0.0080 inches. The proximal portion of the outer sheath 805 may also include a braided reinforcement thermally fused between the inner PTFE liner and the outer Pebax jacket.

Figure 9B:
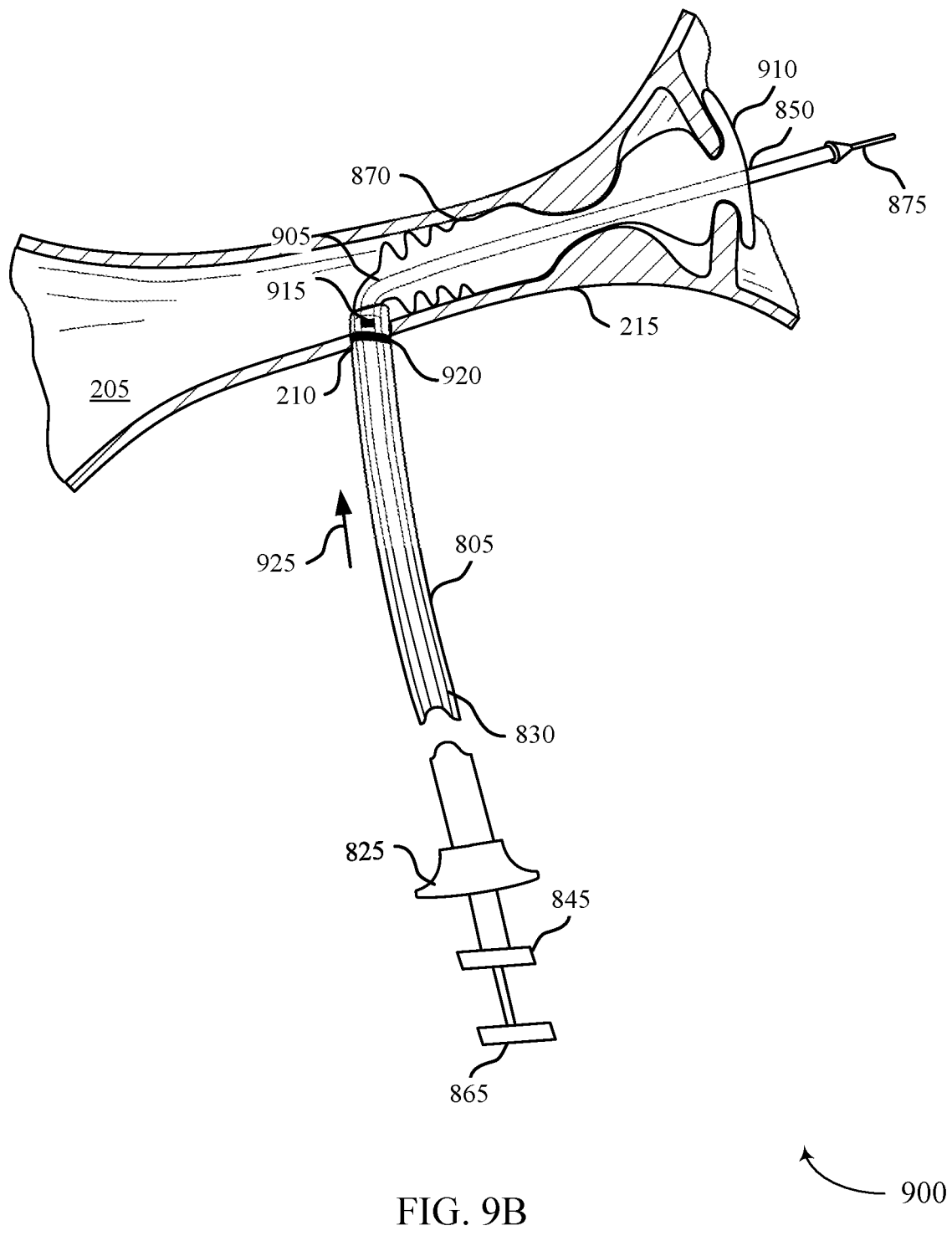
FIG. 9B illustrates a stent delivery system with the proximal portion of the stent compressed in the body lumen in accordance with aspects of the present disclosure.

FIG. 9B illustrates a stent delivery system 900 with the proximal portion 905 of the stent 870 compressed within the body lumen 205 in accordance with aspects of the present disclosure. Once the outer sheath 805 is retracted towards the access site 210, the inner pusher 830 may be advanced in the distal direction, as indicated by arrow 925, to push the proximal portion 905 from the distal end of the outer sheath 805. For example, the middle handle 845 may be advanced in a distal direction to advance the inner pusher 830. As the inner pusher 830 is advanced, the proximal portion 905 of the stent 870 may begin to exit the outer sheath 805 and be compressed against the distal portion 910 of the stent 870. As shown, the stent 870 may be compressed like an accordion as the proximal portion 905 is advanced towards the fixed distal portion 910. The inner pusher 830 may be advanced until the proximal portion 905 of the stent 870 fully exits the outer sheath 805. In some cases, the inner pusher 830 may be advanced until a distal end of the inner pusher 830 aligns with the distal end of the outer sheath 805.

As the inner pusher 830 is advanced, the outer sheath 805 may remain in a fixed position. That is, the outer sheath handle 825 coupled with the outer sheath 805 may be locked in a stationary position while the middle handle 845 coupled with the inner pusher 830 may be advanced distally. For example, the outer sheath 805 may be locked to an endoscope via a clamping mechanism or a locking mechanism (e.g., Touhy boost). In some cases, the proximal handle 865 of the guidewire lumen 850 may remain in a locked position as the inner pusher 830 is advanced in a distal direction.

Figure 9C:
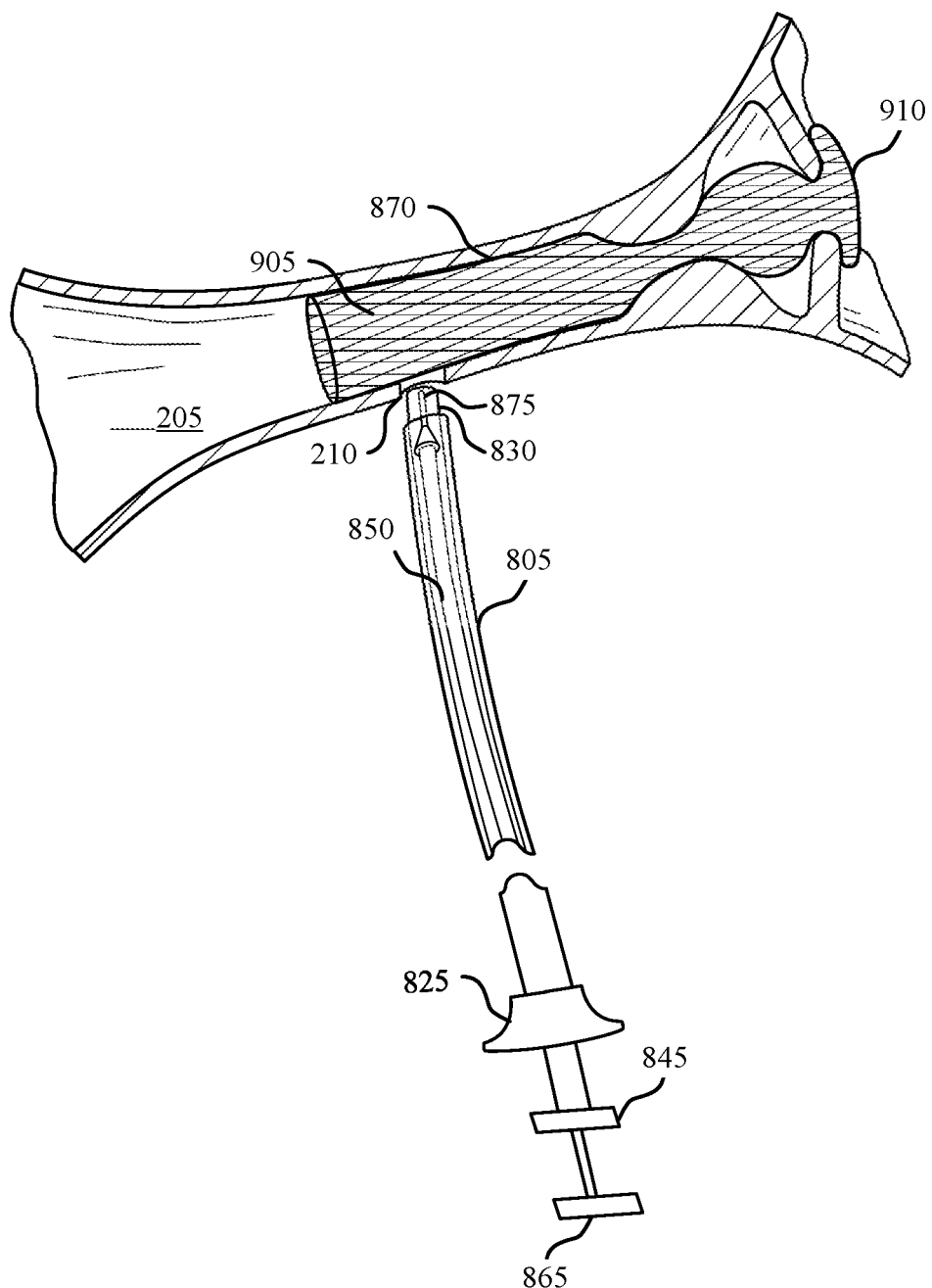
FIG. 9C illustrates a stent delivery system with the stent fully deployed in accordance with aspects of the present disclosure.

FIG. 9C illustrates a stent delivery system 900 with the stent 870 fully deployed in accordance with aspects of the present disclosure. To deploy the stent 870 within the body lumen 205, the inner pusher 830 may be advanced until the entire stent 870 is pushed into the body lumen 205. Once the guidewire lumen 850 and guidewire 875 are withdrawn through the access site 210, the stent 870 may fully deployed such that the proximal portion 905 of the stent 870 may expand to at least partially cover the access site 210. In that case, the proximal portion 905 may "bounce-back" or recoil to cover the access site 210, due to the fact that the stent 870 was compressed like an accordion. In the case of a self-expanding stent, the stent 870 expands to contact the inner surface of the body lumen 205.

Figure 10A:
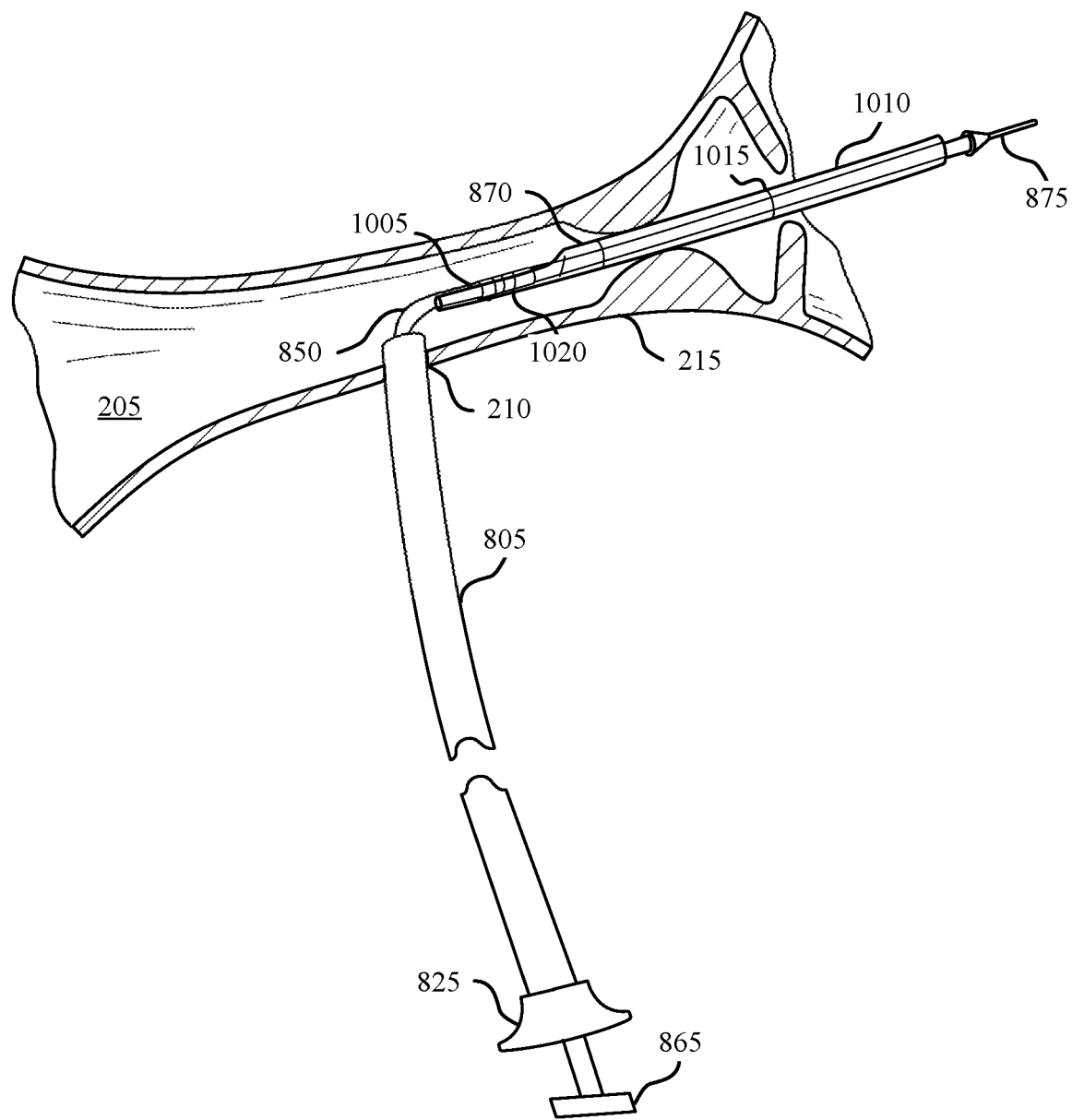
FIG. 10A illustrates a stent delivery system with a coupler in accordance with aspects of the present disclosure.

FIG. 10A illustrates a stent delivery system 1000 with a coupler 1020 in accordance with aspects of the present disclosure. As the outer sheath 805 is withdrawn proximally, the stent 870 may be exposed within the body lumen 205. In some cases, the outer sheath 805 may be advanced distally to cover the stent 870 if repositioning is required. Once the desired anatomical position of the stent 870 is achieved within the body lumen 205, the outer sheath 805 may be retracted.

In some cases, the stent 870 may be releasably coupled with the guidewire lumen 850 by a primary constrainment member 1015. For example, the primary constrainment member 1015 may couple a distal portion 1010 of the stent 870 to a distal section of the guidewire lumen 850. In some cases, the primary constrainment member 1015 may be tied around a proximal portion 1005 of the stent 870 without coupling the proximal portion 1005 to the guidewire lumen 850. In some examples, the primary constrainment member 1015 may be an example of a filament tied around the stent 870, a wire wrapped around the stent 870, a wire frame at least partially wrapped around the stent 870, a splittable sheath, or a combination thereof, as described in reference to FIGS. 3-5. In some cases, the stent 870 may be partially disposed around the guidewire lumen 850. For example, the guidewire lumen 850 may be outside the stent 870 along a proximal portion 1005 of the stent 870, and the guidewire lumen 850 may be inside the stent 870 along a distal portion 1010 of the stent 870.

The stent delivery system 1000 may include a coupler 1020. The coupler 1020 may join a distal section of the guidewire lumen 850 to a proximal section of the guidewire lumen 850. For example, the guidewire lumen 850 may include separate concentric shaft components (e.g., distal and proximal sections), where the distal section and the proximal sections of the guidewire lumen 850 may each be joined to each other via the coupler 1020. In some cases, the coupler 1020 may be located below the proximal portion 1005 of the stent 870. In other examples, the coupler 1020 may be located at a junction between the proximal section of the guidewire lumen 850 and the proximal handle 866 of the guidewire lumen 850.

The coupler 1020 may be made of a number of materials including, but not limited to, metals, plastics, or both. In some cases, the proximal section and distal section of the guidewire lumen 850 may be attached to the coupler 1020 by adhesives, welding, or both. The diameter of the coupler 1020 may vary according to the diameter of the guidewire lumen 850.

In some examples, the proximal portion 1005 of the stent 870 may be aligned on the bottom of the guidewire lumen 850 (e.g., facing towards the access site 210). In that case, the proximal portion 1005 of the stent 870 may catch on the wall 215 or the access site 210 as the stent 870 is retracted towards the access site 210. As discussed in more detail below, to prevent the stent 870 from catching on the wall 215 or the access site 210, the stent 870 may be rotated to align the proximal portion 1005 of the stent 870 on the top of the guidewire lumen 850 (e.g., facing away from the access site 210).

Figure 10B:
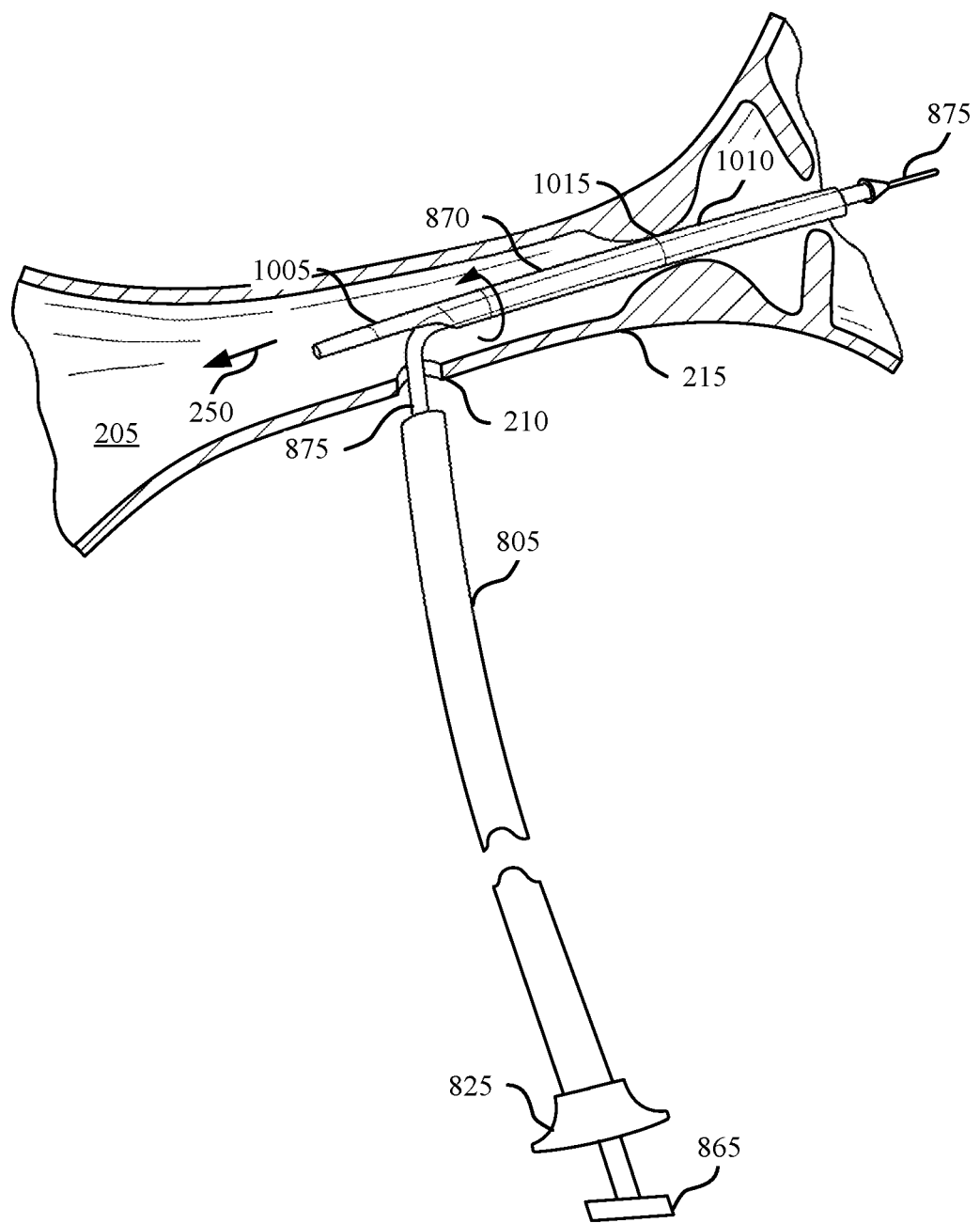
FIG. 10B illustrates a stent delivery system with the stent and a coupler retracted towards the access site in accordance with aspects of the present disclosure.

FIG. 10B illustrates a stent delivery system 1000 with the stent 870 and the coupler 1020 retracted towards the access site 210 in accordance with aspects of the present disclosure. Once the outer sheath 805 is withdrawn through the access site 210, the stent 870 may be pulled toward the access site 210 in a proximal direction, as indicated by arrow 250. The stent 870 may be retracted towards the access site 210 by pulling the guidewire lumen 850 in a proximal direction. For example, the stent 870 may be pulled toward the access site 210 until the proximal portion 1005 of the stent 870 at least partially covers the access site 210. Furthermore, the stent 870 may be repositioned within the body lumen 205 to at least partially cover the access site 210. In some cases, the proximal portion 1005 of the stent 870 may be tied such that the primary constrainment member 1015 prevents the proximal portion 1005 from catching on the wall 215 of the body lumen as the stent 870 is retracted.

In some cases, the stent 870 may be rotated to align the proximal portion 1005 of the stent 870 on top of the guidewire lumen 850 (e.g., facing away from the access site 210). To rotate the proximal portion 1005 of the stent 870, the proximal section of the guidewire lumen 850 may rotate via the coupler 1020. For example, the proximal portion 1005 of the stent 870 may rotate away from the access site 210 by withdrawing the guidewire lumen 850 including the coupler 1020) proximally and back through the access site 210. In this case, the guidewire lumen 850 may be under tension and be configured to align with an inside curve of the body lumen 205. For example, the guidewire lumen 850 may be pulled to the inside curve of the body lumen 205, and the coupler 1020 may rotate the proximal portion 1005 of the stent 870 towards the outside curve of the body lumen 205. In some case, the proximal section of the guidewire lumen 850 may be rotated away from the access site 210 such that the coupler 1020 prevents the proximal portion 1005 of the stent 870 from catching on the wall 215 of the body lumen 205 as the stent 870 is retracted. In this case, the distal section of the guidewire lumen 850 may remain in a stationary position while the proximal section of the guidewire lumen 850 rotates.

Figure 10C:
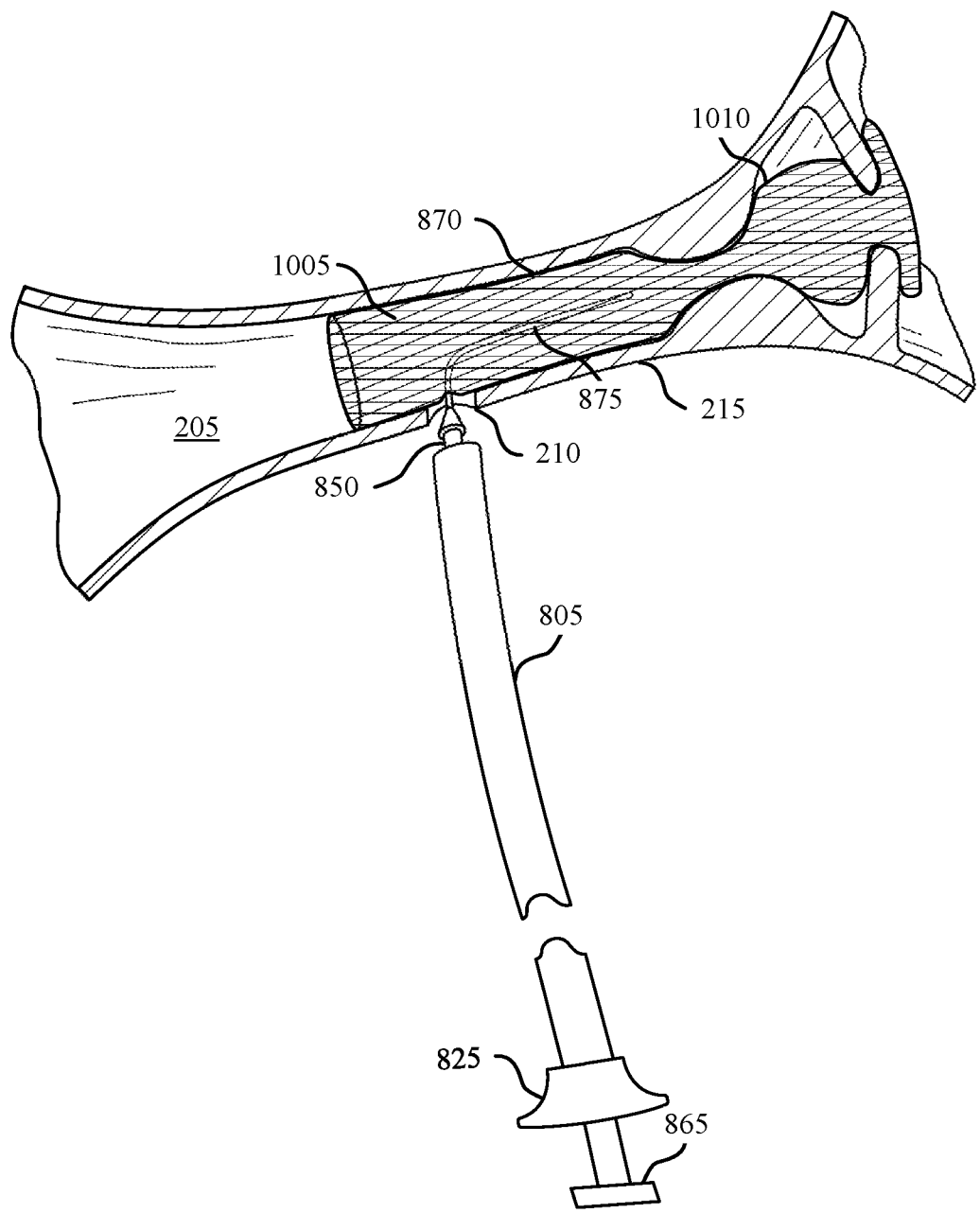
FIG. 10C illustrates a stent delivery system with the stent fully deployed in accordance with aspects of the present disclosure.

FIG. 10C illustrates a stent delivery system 1000 with the stent 870 fully deployed in accordance with aspects of the present disclosure. To deploy the stent 870 within the body lumen 205, the primary constraint member may be released. In some cases, the stent 870 may be deployed by pulling the primary constraint member in a proximal direction, pulling one or more tethers coupled with the primary constraint member, or both. In the case of a self-expanding stent, the stent 870 expands to contact the inner surface of the body lumen 205. Once the stent 870 expands within the body lumen 205, the guidewire lumen 850 and the guidewire 875 are withdrawn through the access site 210.

Figure 11:
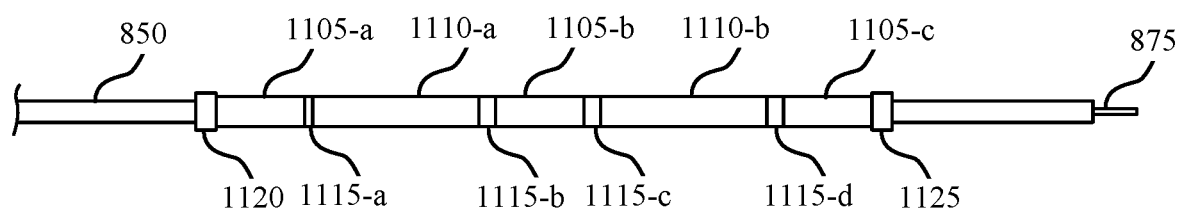
FIG. 11 illustrates a stent delivery system with a positioning member in accordance with aspects of the present disclosure.

FIG. 11 illustrates a stent delivery system 1100 with a positioning member in accordance with aspects of the present disclosure. The positioning member may include extrusions 1105-a, 1105-b, and 1105-c and rotating rings 1110-a and 1110-b. The extrusions 1105-a, 1105-b, and 1105-c and rotating rings 1110-a and 1110-b may be concentrically loaded to the guidewire lumen 850.

The extrusions 1105-a, 1105-b, and 1105-c may be made of a number of materials including, but not limited to polyimide. The extrusions 1105-a, 1105-b, and 1105-c may be bonded to the guidewire lumen 850 such that the rotating rings 1110-a and 1110-b may be separated by a distance equal or greater than the length of the extrusions 1105-a, 1105-b, and 1105-c.

The rotating rings 1110-a and 1110-b may be made of a number of materials including, but not limited to stainless steel, polyether ether ketone (PEEK), a family of polyetherimide products (i.e., Ultem), other metals, or a combination thereof. The rotating rings 1110-a and 1110-b may be releasably coupled to the guidewire lumen 850 such that the rotating rings 1110-a and 1110-b may freely spin around the guidewire lumen 850. As described below in further detail, the rotating rings 1110-a and 1110-b may rotate a stent to align the proximal portion of the stent away from the access site.

In some cases, extrusions 1105-a, 1105-b, and 1105-c may be spaced apart from rotating rings 1110-a and 1110-b by spacers 1115-a, 1115-b, 1115-c, and 1115-d. For example, the extrusion 1105-a may be separated from the rotating ring 1110-a by the spacer 1115-a. The spacers 1115-a, 1115-b, 1115-c, and 1115-d may be made of a number of materials including, but not limited to nylon.

In some examples, a proximal positioning member 1120 may abut an edge of the extrusion 1105-a and a distal positioning member 1125 may abut an edge of the extrusion 1105-c. The proximal positioning member 1120 and the distal positioning member 1125 may be made of a number of materials, including, but not limited to Pebax. As described below in further detail, the proximal positioning member 1120 and distal positioning member 1125 may serve as a stopper for the primary constraint member attached to the stent.

In some cases, the rotating rings 1110-a and 1110-b may be an example of a single rotating ring. In other examples, the rotating ring 1110-a may abut the proximal positioning member 1120 and the rotating ring 1110-b may abut the distal positioning member 1125.

Figure 12A:
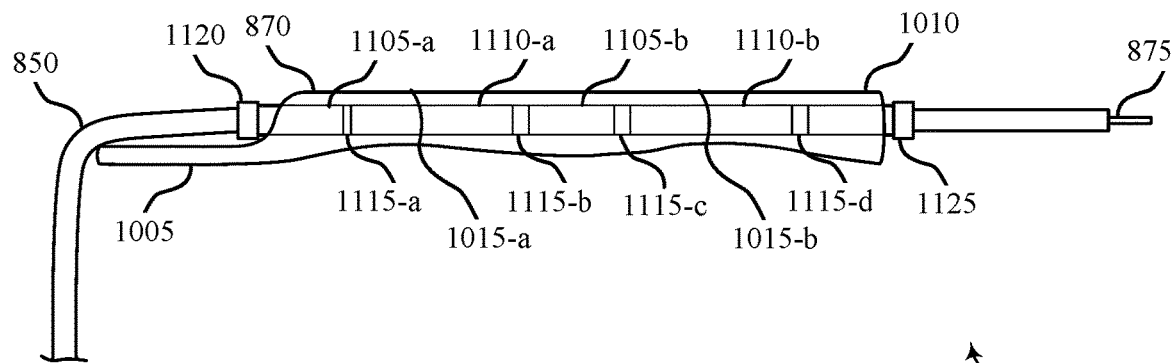
FIGS. 12A-C illustrate stent delivery systems with a stent disposed on a positioning member in accordance with aspects of the present disclosure.
Figure 12B:
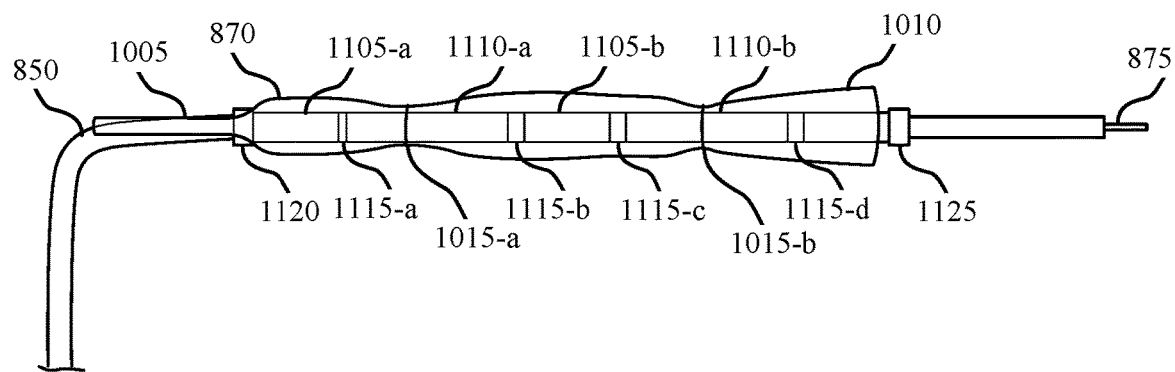
Figure 12C:
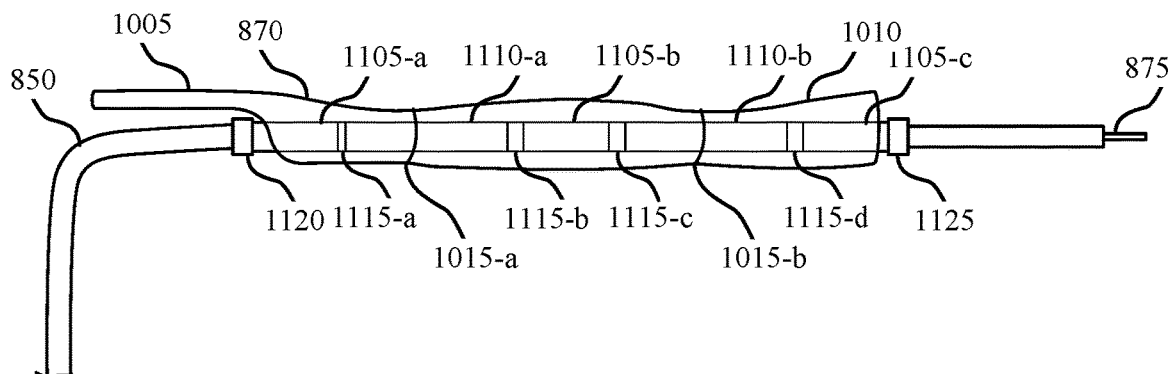

FIGS. 12A-C illustrate stent delivery systems 1200 with a stent disposed on a positioning member in accordance with aspects of the present disclosure. As described in reference to FIGS. 10A-C, the positioning member (e.g., including extrusions 1105-a, 1105-b, and 1105-c and rotating rings 1110-a and 1110-b) may be used to rotate the proximal portion 1005 of the stent 870 on top of the guidewire lumen 850 (e.g., facing away from the access site).

In some cases, the stent 870 may be partially disposed around the guidewire lumen 850. For example, the guidewire lumen 850 may be outside the stent 870 along a proximal portion 1005 of the stent 870, and the guidewire lumen 850 may be inside the stent 870 along a distal portion 1010 of the stent 870. In some cases, the stent 870 may be releasably coupled with the guidewire lumen 850 by a primary constraint member 1015-a and 1015-b. For example, the primary constraint member 1015-a may couple a distal portion 1010 of the stent 870 to rotating ring 1110-a and the primary constraint member 1015-b may couple a distal portion 1010 of the stent 870 to rotating ring 1110-b. In some examples, the primary constraint member 1015-a and 1015-b may be examples of a filament tied around the stent 870, a wire wrapped around the stent 870, a wire frame at least partially wrapped around the stent 870, a splittable sheath, or a combination thereof, as described in reference to FIGS. 3-5.

As described in reference to FIG. 12A, the proximal portion 1005 of the stent 870 may be aligned on the bottom of the guidewire lumen 850 facing towards the access site). In that case, the proximal portion 1005 of the stent 870 may catch on the wall or the access site as the stent 870 is retracted towards the access site, as discussed in reference to FIGS. 10A-C. To prevent the stent 870 from catching on the wall or the access site, the stent 870 may be rotated to align the proximal portion 1005 of the stent 870 on the top of the guidewire lumen 850 (e.g., facing away from the access site).

As described in reference to FIG. 12B, the stent 870 may be rotated to align the proximal portion 1005 of the stent 870 on top of the guidewire lumen 850 (e.g., facing away from the access site). To rotate the proximal portion 1005 of the stent 870, the distal portion 1010 of the stent 870 may rotate via the rotating rings 1110-a and 1110-b. For example, the proximal portion 1005 and the distal portion 1010 of the stent 870 may rotate away from the access site by withdrawing the guidewire lumen 850 proximally and back through the access site. In that case, the distal portion 1010 of the stent 870 coupled to the rotating rings 1110-a and 1110-b via primary constraint members 1015-a and 1015-*b*, respectively, may rotate. That is, the rotating rings 1110-*a* and 1110-*b* may rotate with respect to the guidewire lumen 850.

As described in reference to FIG. 12C, the proximal portion 1005 of the stent 870 may be rotated to align the proximal portion 1005 of the stent 870 on the top of the guidewire lumen 850 (e.g., away from the access site). In this case, the rotating rings 1110-*a* and 110-*b* may prevent the proximal portion 1005 of the stent 870 from catching on the wall of the body lumen 205 as the stent 870 is retracted, as discussed in reference to FIGS. 10A-C. In this case, the extrusions 1105-*a*, 1105-*b*, and 1105-*c* bonded to the guidewire lumen 850 may remain in a stationary position while the rotating rings 1110-*a* and 1110-*b* rotate around the guidewire lumen 850.

Figure 13:
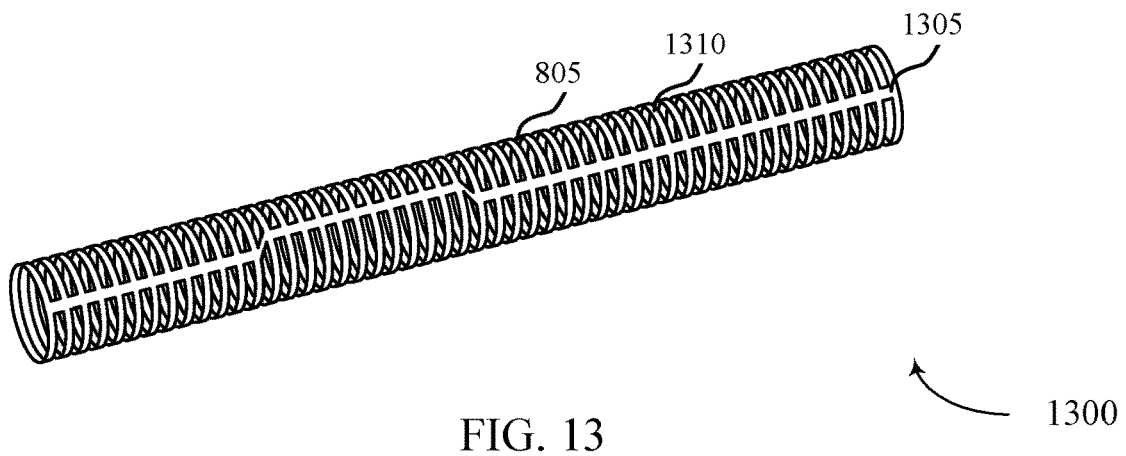
FIG. 13 illustrates a stent delivery system with a laser cut outer sheath in accordance with aspects of the present disclosure.

FIG. 13 illustrates a stent delivery system 1300 with a laser cut outer sheath 805 in accordance with aspects of the present disclosure. In some cases, the outer sheath 805 may include one or laser cuts 1310. For example, the laser cuts 1310 may circumscribe the outer sheath 805 to form a spline 1305. In that case, the laser cuts 1310 may extend around a partial circumference of the outer sheath 805 and abut the spline 1305. The spline 1305 may extend from a proximal end of the outer sheath 805 to a distal end of the outer sheath 805. In some cases, the laser cuts 1310 may be imparted into to outer sheath 805 in more than one pattern. For example, the laser cuts 1310 may be cut to form a helical spline. In some examples, the helical spline may extend along a distal portion of the outer sheath 805 and a longitudinal spline may extend along a proximal portion of the outer sheath 805.

In some cases, the stent may be loaded within the outer sheath 805 relative to the laser cuts 1310. For example, to align the stent in the body lumen such that the proximal portion of the stent is orientated away from the inner wall of the body lumen, the proximal portion of the stent may be positioned 180 degrees opposite of the spline 1305. In some cases, the spline 1305 may include a higher stiffness than the laser cuts 1310 imparted into the outer sheath 805. For example, the spline 1305 may align to the lesser curvature of the duct (e.g., will adopt the path of least resistance in bending) and align to the inner radius of curvature of the duct. In such cases, the outer sheath 805 may align to the inner radius of curvature of the duct, thereby causing the stent to align with the inner radius curvature of the duct. In some cases, the guidewire lumen may rotate within the stent.

If the proximal portion of the stent is positioned opposite of the spline 1305, the proximal portion of the stent may expand along the outer radius of the curvature of the duct after the outer sheath 805 is retracted. That is, the proximal portion of the stent may deploy away from the inner wall of the body lumen when the outer sheath 805 is retracted. This may prevent the proximal portion of the stent from catching on the inner wall of the body lumen or the access site as the stent is retracted to cover the access site. The outer sheath 805 may be made of a number of metallic materials including, but not limited to, nitinol.

Figure 14:
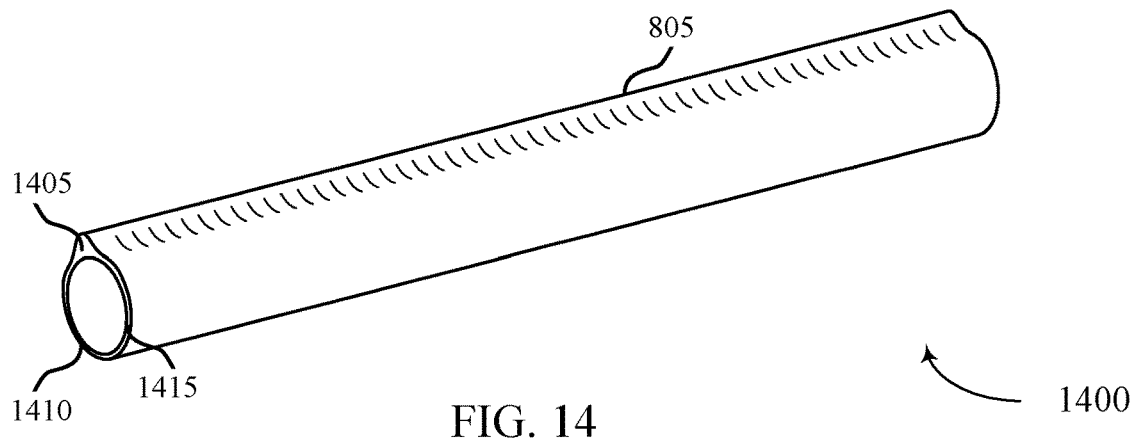
FIG. 14 illustrates a stent delivery system with a bumped extrusion outer sheath in accordance with aspects of the present disclosure.

FIG. 14 illustrates a stent delivery system 1400 with a bumped extrusion outer sheath in accordance with aspects of the present disclosure. In some cases, the outer sheath 805 may contain a bumped extrusion 1405. For example, the bumped extrusion 1405 may extend form a distal end to a proximal end of the outer sheath 805. The bumped extrusion 1405 may be disposed between an outer surface 1410 of the outer sheath 805 and an inner surface 1415 of the outer sheath 805. In some examples, the inner surface 1415 of the outer sheath 805 may be an example of a PTFE liner. In other examples, the outer surface 1410 of the outer sheath 805 may be made of a low durometer material. In some cases, the bumped extrusion 1405 may be made of a high durometer material. The bumped extrusion 1405 may approximately 1 to 3 mm wide.

In some cases, the stent may be loaded within the outer sheath 805 relative to the bumped extrusion 1405. For example, to align the stent in the body lumen so that the proximal portion of the stent is orientated away from the inner wall of the body lumen, the proximal portion of the stent may be positioned 180 degrees opposite of the bumped extrusion 1405. The bumped extrusion 1405 may include a higher stiffness than the portions of the outer sheath 805 without the bumped extrusion 1405. For example, the bumped extrusion 1405 may align to the lesser curvature of the duct (e.g., will adopt the path of least resistance in bending) and align to the inner radius of curvature of the duct. In such cases, the outer sheath 805 may align to the inner radius of curvature of the duct, thereby causing the stent to align with the inner radius curvature of the duct. In some cases, the guidewire lumen may rotate within the stent.

If the proximal portion of the stent is positioned opposite of the bumped extrusion 1405, the proximal portion of the stent may expand along the outer radius of the curvature of the duct after the outer sheath 805 is retracted. For example, the outer sheath 805 may be retracted to deploy the stent, and the proximal portion of the stent may deploy away from the inner wall of the body lumen. This may prevent the proximal portion of the stent from catching on the inner wall of the body lumen or the access site as the stent is retracted to cover the access site.

Figure 15:
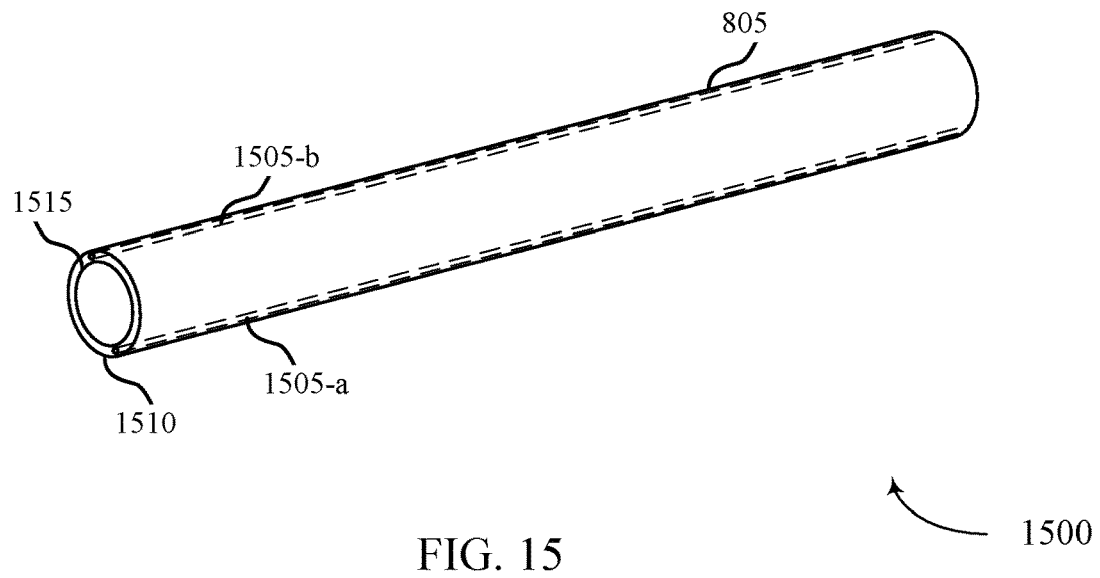
FIG. 15 illustrates a stent delivery system with a wired outer sheath in accordance with aspects of the present disclosure.

FIG. 15 illustrates a stent delivery system 1500 with a wired outer sheath in accordance with aspects of the present disclosure. In some cases, the outer sheath 805 may contain a first wire 1505-*a* and a second wire 1505-*b*. For example, the first wire 1505-*a* and the second wire 1505-*b* may extend from a distal end to a proximal end of the outer sheath 805. The first wire 1505-*a* and second wire 1505-*h* may be disposed between an outer surface 1510 of the outer sheath 805 and an inner surface 1515 of the outer sheath 805. In some examples, the inner surface 1515 of the outer sheath 805 may be an example of a PTFE liner. In some cases, a helical braided jacket may be disposed on the inner surface 1515 of the outer sheath 805. The outer surface 1510 of the outer sheath 805 may be made of a polymer material. The first wire 1505-*a* and the second wire 1505-*b* may be made of a number of metallic materials including, but not limited to, stainless-steel. In some cases, the first wire 1505-*a* and the second wire 1505-*b* may be positioned 180 degrees opposite of each other.

In some cases, the stent may be loaded within the outer sheath 805 relative to the first wire 1505-*a* and the second wire 1505-*b*. For example, to align the stent in the body lumen such that the proximal portion of the stent is orientated away from the inner wall of the body lumen, the proximal portion of the stent may be positioned 90 degrees opposite of the first wire 1505-*a* and the second wire 1505-*b*. For example, the stent may deploy outwards in a direction 90 degrees opposite the first wire 1505-*a* and the second wire 1505-*b*. In some cases, the first wire 1505-*a* and second wire 1505-*b* may include a higher stiffness than the portions of the outer sheath 805 without the first wire 1505-*a* and the second wire 1505-*b*. For example, the first wire 1505-*a* and second wire 1505-*b* may align to the lesser curvature of the duct (e.g., will adopt the path of least resistance in bending) and align to the inner radius of curvature of the duct. In this case, the portion of the outer sheath 805 without the first wire 1505-*a* and the second wire 1505-*b* may align the inner radius of curvature of the duct.

If the proximal portion of the stent is positioned 90 degrees opposite the first wire 1505-*a* and second wire 1505-*b*, the proximal portion of the stent may expand along the outer radius of the curvature of the duct after the outer sheath 805 is retracted. For example, the outer sheath 805 may be retracted, and the proximal portion of the stent may deploy away from the inner wall of the body lumen. This may prevent the proximal portion of the stent from catching on the inner wall of the body lumen or the access site as the stent is retracted to cover at least a portion of the access site.

In some cases, the outer sheath 805 may contain a third wire (not shown). In that case, the first wire 1505-*a*, the second wire 1505-*b*, and the third wire may be positioned 90 degrees apart around the circumference of the outer sheath 805. The second wire 1505-*b* may align to the lesser curvature of the duct and align to the inner radius of curvature of the duct. The first wire 1505-*a* and the third wire may align 90 degrees opposite the second wire 1505-*b*. That is, the stent may deploy outwards from between the first wire 1505-*a* and the third wire (e.g., 180 degrees opposite the second wire 1505-*b*). In some cases, the outer sheath 805 may contain a bumped extrusion, as described in reference to FIG. 14. In that case, the first 1505-*a*, the second wire 1505-*b*, and the bumped extrusion may be positioned 120 degrees apart around the circumference of the outer sheath 805.

Figure 16:
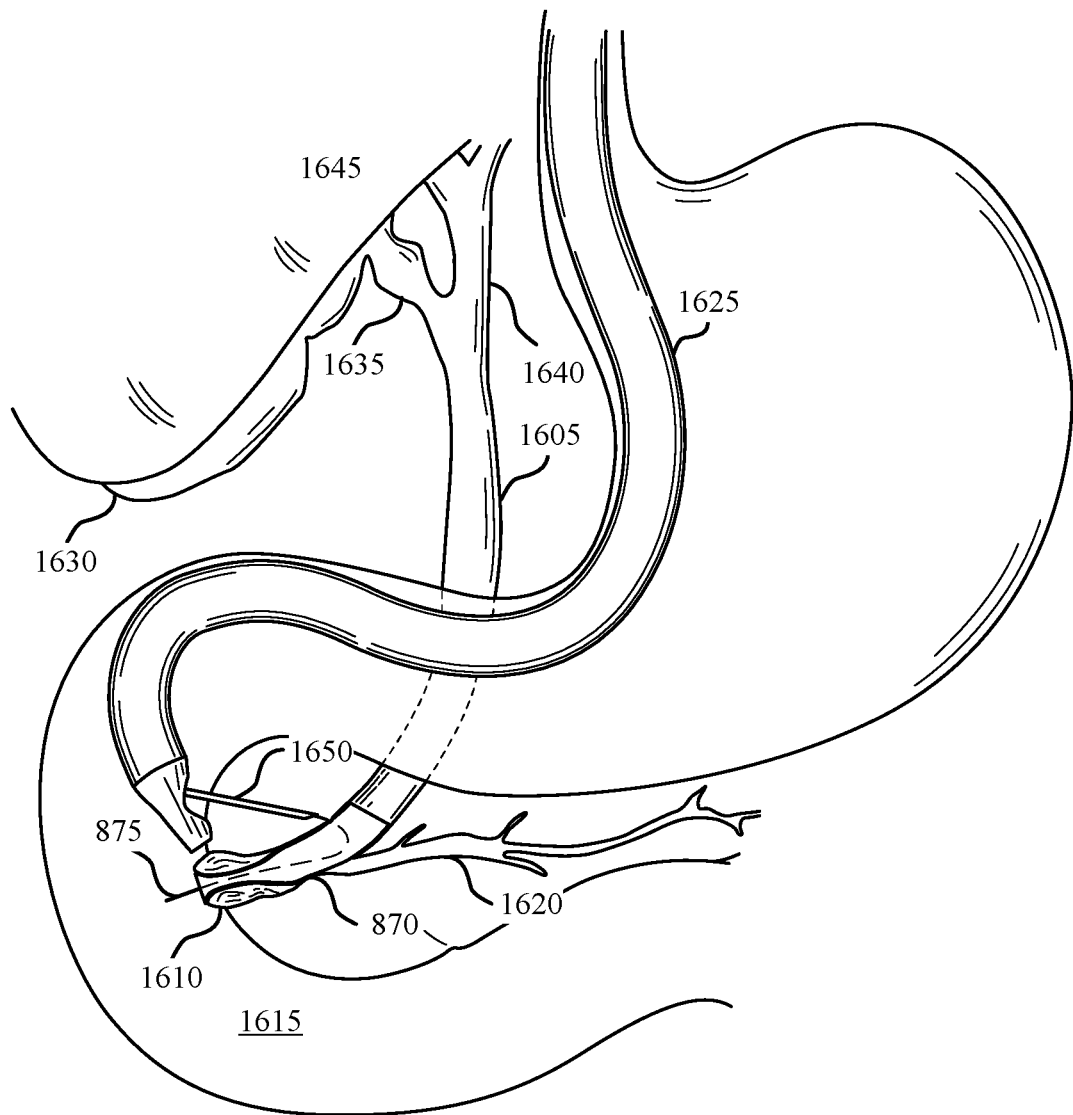
FIG. 16 illustrates a system for providing access to a body lumen within the pancreaticobiliary system is illustrated in accordance with aspects of the present disclosure.

With reference to FIG. 16, a system 1600 for providing access to a body lumen within the pancreaticobiliary system is illustrated in accordance with aspects of the present disclosure. The system 1600 may be examples of or include functionality of the systems or components described with reference to any of FIGS. 1-15. The illustrated portions of the pancreaticobiliary system include the common bile duct 1605, which drains bile from both the cystic duct 1635 (which drains from the gallbladder 1630) and the common hepatic duct 1640 (which drains from the liver 1645) into the duodenum 1615, where, the bile mixes and reacts with digesting food. As shown, the common bile duct 1605 joins with the pancreatic duct 1620 at the ampulla of Vater 1610 (shown obstructed) before draining through the major duodenal papilla into the duodenum 1615.

A clinician may advance an endoscope 1625 (e.g., an EUS endoscope) into the lumen of a patient's duodenum 1615 to a position in which the bile ducts may be visualized (e.g., via endosonography). The clinician may then access the common bile duct 1605 by advancing a separate access device from a working channel of the endoscope 1625, through the wall of the duodenum 1615 (i.e., trans-duodenally), and then through the wall of the common bile duct 1605.

The clinician may then insert a guidewire 875 via the separate access device, thereby allowing the stent delivery system 1650 to be tracked over the guidewire 875. After the stent delivery system 1650 is advanced into the common bile duct 1605, the stent delivery system 1650 may be pulled back to position the stein over the access site, as described in reference to FIGS. 2-9. In some cases, the stent delivery system 1650 may be repositioned to place the stent over the access site, as described in reference to FIGS. 10-15. Stent delivery system 1650 may be an example of the systems or components described with reference to any of FIGS. 1-15.

Figure 17:
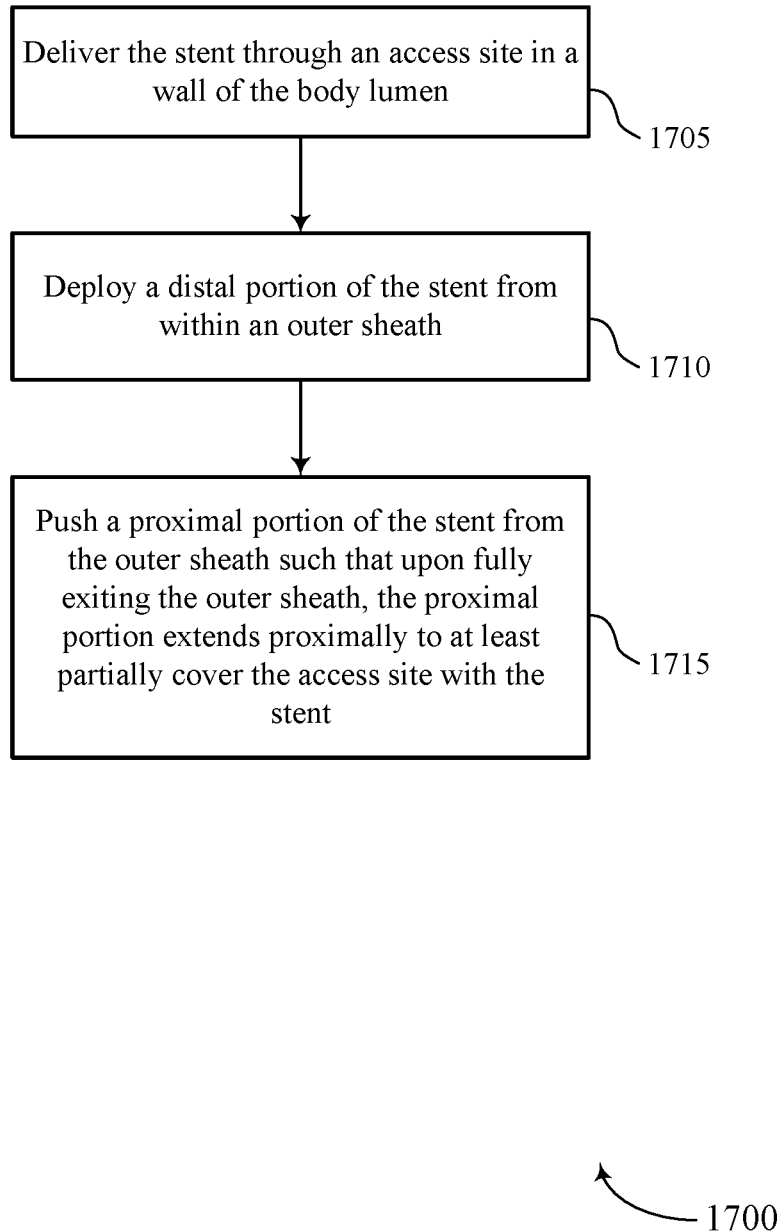
FIGS. 17-19 illustrate flow diagrams of methods in accordance with aspects of the present disclosure.

FIG. 17 illustrates a flowchart of a method 1700 for expandable stent delivery apparatus to cover an access site with aspects of the present disclosure. At block 1705, the method may include delivering the stent through an access site in a wall of the body lumen described in reference to FIGS. 8 and 9.

At block 1710, the method may include deploying a distal portion of the stent from within an outer sheath described in reference to FIGS. 8 and 9. In some examples, the process of deploying the distal portion may include retracting the outer sheath toward the access site such that the distal portion of the stent expands within the body lumen.

At block 1715, the method may include pushing a proximal portion of the stent from the outer sheath such that upon fully exiting the outer sheath, the proximal portion extends proximally to at least partially cover the access site with the stent described in reference to FIGS. 8 and 9. In some examples, the process of pushing the proximal portion of the stent from the outer sheath includes advancing an internal pusher in a distal direction, where the internal pusher is at least partially disposed within the outer sheath and coupled with the proximal portion of the stent. In some examples, the process of pushing the proximal portion of the stent from the outer sheath includes advancing the internal pusher until the proximal portion of the stent fully exits the outer sheath.

Figure 18:
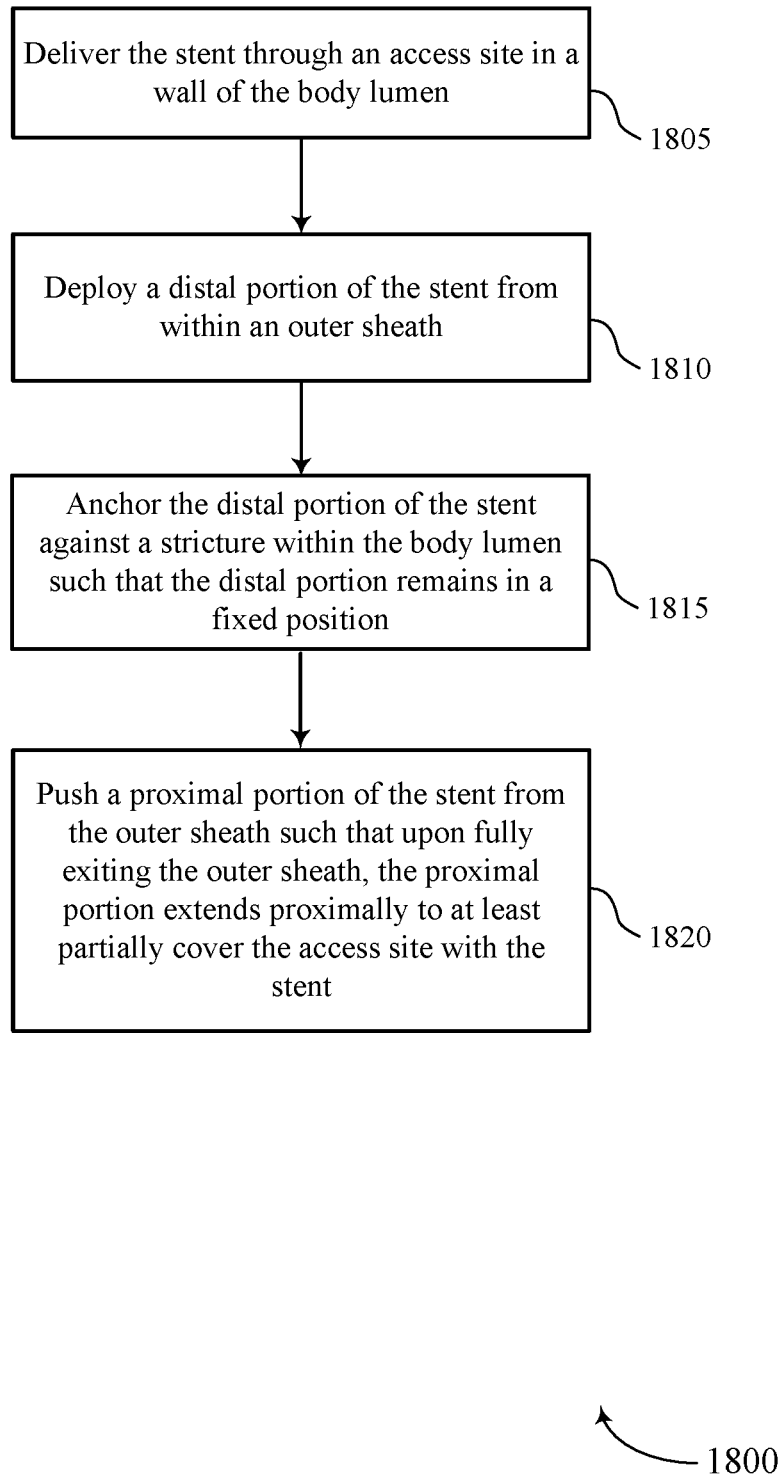

FIG. 18 illustrates a flowchart of a method 1800 for expandable stent delivery apparatus to cover an access site with aspects of the present disclosure. At block 1805, the method may include delivering the stent through an access site in a wall of the body lumen described in reference to FIGS. 8 and 9.

At block 1810, the method may include deploying a distal portion of the stent from within an outer sheath described in reference to FIGS. 8 and 9. In some examples, the process of deploying the distal portion may include retracting the outer sheath toward the access site such that the distal portion of the stent expands within the body lumen.

At block 1815, the method may include anchoring the distal portion of the stent against a stricture within the body lumen such that the distal portion remains in a fixed position described in reference to FIGS. 8 and 9.

At block 1820, the method may include pushing a proximal portion of the stent from the outer sheath such that upon fully exiting the outer sheath, the proximal portion extends proximally to at least partially cover the access site with the stent described in reference to FIGS. 8 and 9. In some examples, the process of pushing the proximal portion of the stent from the outer sheath includes advancing an internal pusher in a distal direction, where the internal pusher is at least partially disposed within the outer sheath and coupled with the proximal portion of the stent. In some examples, the process of pushing the proximal portion of the stent from the outer sheath includes advancing the internal pusher until the proximal portion of the stent fully exits the outer sheath.

Figure 19:
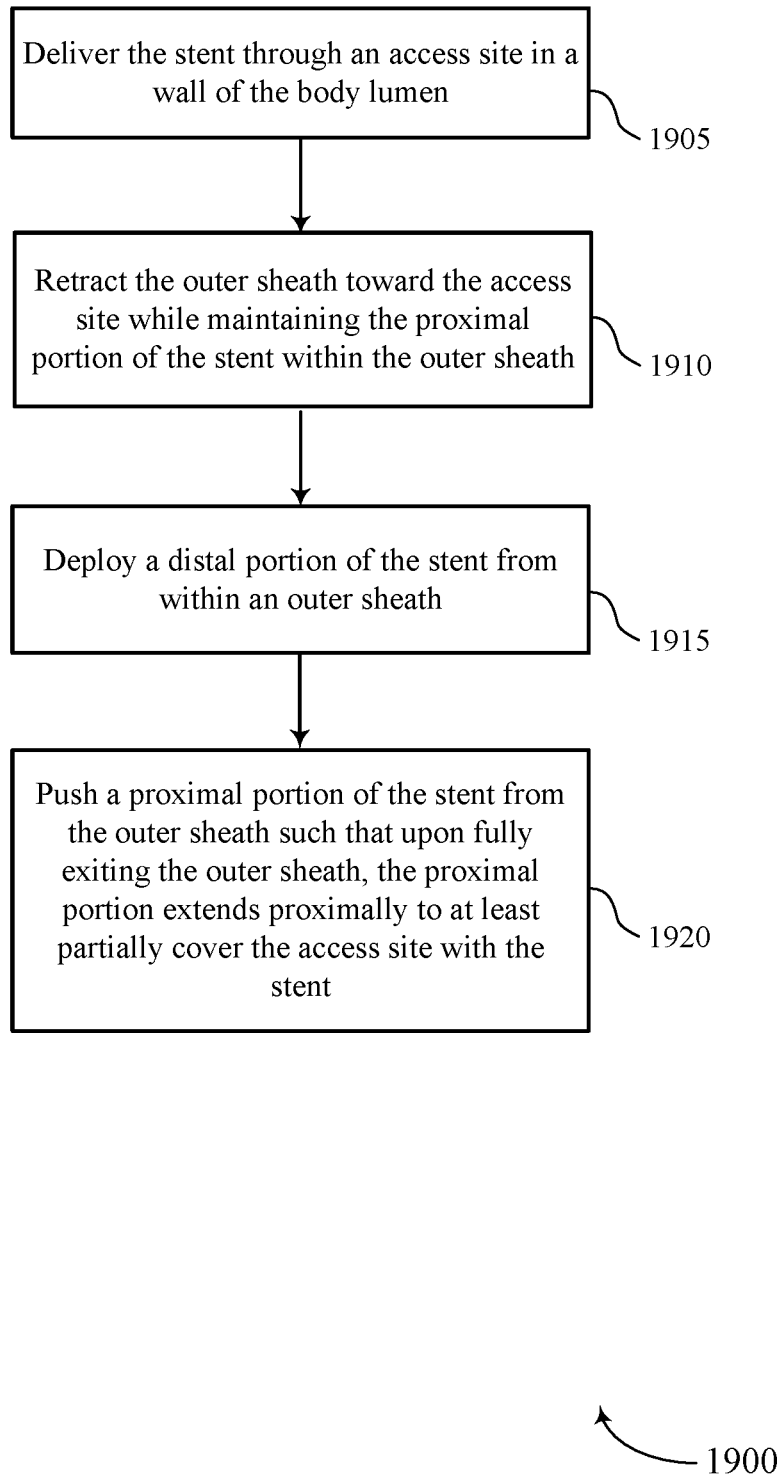

FIG. 19 illustrates a flowchart of a method 1900 for expandable stent delivery apparatus to cover an access site with aspects of the present disclosure. At block 1905, the method may include delivering the stent through an access site in a wall of the body lumen described in reference to FIGS. 8 and 9.

At block 1910, the method may include retracting the outer sheath toward the access site while maintaining the proximal portion of the stent within the outer sheath described in reference to FIGS. 8 and 9. In some examples, the process of retracting the outer sheath may include aligning a distal end of the outer sheath with the wall of the body lumen of the access site.

At block 1915, the method may include deploying a distal portion of the stent from within an outer sheath described in reference to FIGS. 8 and 9. In some examples, the process of deploying the distal portion may include retracting the outer sheath toward the access site such that the distal portion of the stent expands within the body lumen.

At block 1920, the method may include pushing a proximal portion of the stent from the outer sheath such that upon fully exiting the outer sheath, the proximal portion extends proximally to at least partially cover the access site with the stent described in reference to FIGS. 8 and 9. In some examples, the process of pushing the proximal portion of the stent from the outer sheath includes advancing an internal pusher in a distal direction, where the internal pusher is at least partially disposed within the outer sheath and coupled with the proximal portion of the stent. In some examples, the process of pushing the proximal portion of the stent from the outer sheath includes advancing the internal pusher until the proximal portion of the stent fully exits the outer sheath.

It should be noted that these methods describe possible implementation, and that the operations and the steps may be rearranged or otherwise modified such that other implementations are possible. In some examples, aspects from two or more of the methods may be combined. For example, aspects of each of the methods may include steps or aspects of the other methods, or other steps or techniques described herein.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed herein.

While several embodiments of the present disclosure have been described and illustrated herein, those of ordinary skill in the art will readily envision a variety of other means or structures for performing the functions or obtaining the results or one or more of the advantages described herein, and each of such variations or modifications is deemed to be within the scope of the present disclosure. More generally, those skilled in the art will readily appreciate that all parameters, dimensions, materials, and configurations described herein are meant to be exemplary and that the actual parameters, dimensions, materials, or configurations will depend upon the specific application or applications for which the teachings of the present disclosure is/are used.

Those skilled in the art will recognize or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, or method described herein. In addition, any combination of two or more such features, systems, articles, materials, kits, or methods, if such features, systems, articles, materials, kits, or methods are not mutually inconsistent, is included within the scope of the present disclosure.

All definitions, as defined and used herein, should be understood to control over dictionary definitions, definitions in documents incorporated by reference, or ordinary meanings of the defined terms.

The indefinite articles "a" and "an," as used herein in the specification and in the claims, unless clearly indicated to the contrary, should be understood to mean "at least one." Also, as used herein, including in the claims, "or" as used in a list of items (for example, a list of items prefaced by a phrase such as "at least one of" or "one or more") indicates an inclusive list such that, for example, a list of at least one of A, B, or C means A or B or C or AB or AC or BC or ABC (i.e., A and B and C).

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

What is claimed is:

1. A method for delivering a stent into a body lumen, comprising:
    delivering a stent through an access site in a wall of the body lumen;
    deploying a distal portion of the stent from within an outer sheath;
    retracting the outer sheath toward the access site while maintaining a proximal portion of the stent within the outer sheath, wherein retracting the outer sheath toward the access site comprises aligning a distal end of the outer sheath with the wall of the body lumen of the access site; and
    pushing the proximal portion of the stent from the outer sheath such that upon fully exiting the outer sheath, the proximal portion remains within the body lumen and extends proximally to fully cover the access site with the stent.

2. The method of claim 1, wherein deploying the distal portion of the stent from the outer sheath comprises:
    retracting the outer sheath toward the access site such that the distal portion of the stent expands within the body lumen.

3. The method of claim 1, wherein pushing the proximal portion of the stent from the outer sheath comprises:
    advancing an internal pusher in a distal direction, wherein the internal pusher is at least partially disposed within the outer sheath and coupled with the proximal portion of the stent.

4. The method of claim 3, wherein pushing the proximal portion of the stent from the outer sheath comprises:
    advancing the internal pusher until the proximal portion of the stent fully exits the outer sheath.

5. The method of claim 3, wherein advancing the internal pusher in the distal direction comprises:
    aligning a distal end of the internal pusher with the distal end of the outer sheath.

6. The method of claim 3, further comprising:
    maintaining the outer sheath in a locked position while advancing the internal pusher.

7. The method of claim 1, further comprising:
    anchoring the distal portion of the stent against a stricture within the body lumen such that the distal portion remains in a fixed position.

8. The method of claim 7, further comprising:
    compressing the stent to a compressed state by advancing the proximal portion of the stent towards the distal portion of the stent.

9. The method of claim 8, further comprising:
expanding the proximal portion of the stent from the compressed state to an expanded state.

10. The method of claim 1, further comprising:
retracting the outer sheath past a stent anchor before pushing the proximal portion of the stent from the outer sheath.

11. The method of claim 1, further comprising:
compressing the distal portion of the stent against a stricture within the body lumen based at least in part on deploying the distal portion of the stent from the outer sheath.

12. The method of claim 1, further comprising:
removing the outer sheath from the body lumen through the access site.

13. The method of claim 1, further comprising:
expanding the stent within the body lumen.

14. The method of claim 1, further comprising:
advancing a stent delivery apparatus through the access site before delivering the stent; and
removing the stent delivery apparatus through the access site after expanding the stent.

15. The method of claim 14, wherein the stent delivery apparatus comprises a guidewire, wherein a tubular member is disposed around the guidewire, and wherein the method further comprises:
advancing the guidewire through the access site before delivering the stent.

* * * * *